(12) United States Patent
Nan et al.

(10) Patent No.: US 8,183,383 B2
(45) Date of Patent: May 22, 2012

(54) PROTEIN TYROSINE PHOSPHATASE 1B INHIBITOR, PREPARATION METHODS AND USES THEREOF

(75) Inventors: Fajun Nan, Shanghai (CN); Jia Li, Shanghai (CN); Yi Wei, Shanghai (CN); Wei Zhang, Shanghai (CN); Jingya Li, Shanghai (CN); Lei Shi, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 12/530,281

(22) PCT Filed: Feb. 26, 2008

(86) PCT No.: PCT/CN2008/000400
§ 371 (c)(1),
(2), (4) Date: Mar. 22, 2010

(87) PCT Pub. No.: WO2008/106860
PCT Pub. Date: Sep. 12, 2008

(65) Prior Publication Data
US 2010/0197927 A1    Aug. 5, 2010

(30) Foreign Application Priority Data

Mar. 6, 2007  (CN) .......................... 2007 1 0037848

(51) Int. Cl.
| | |
|---|---|
| C07D 277/30 | (2006.01) |
| C07D 263/34 | (2006.01) |
| C07D 233/00 | (2006.01) |
| C07D 233/61 | (2006.01) |
| C07D 417/10 | (2006.01) |
| C07D 413/10 | (2006.01) |
| C07D 401/10 | (2006.01) |
| A61K 31/445 | (2006.01) |
| A61K 31/44 | (2006.01) |
| A61K 31/425 | (2006.01) |
| A61K 31/42 | (2006.01) |
| A61K 31/415 | (2006.01) |

(52) U.S. Cl. ..................... 548/204; 548/236; 548/311.1; 548/335.5; 546/209; 546/269.7; 546/271.4; 546/272.7; 514/326; 514/341; 514/342; 514/340; 514/365; 514/374; 514/396; 514/397

(58) Field of Classification Search ........................ None
See application file for complete search history.

(56) References Cited

OTHER PUBLICATIONS

Sellanes et al. Tetrahedron Letters (2007), 48(10), 1827-1830.*
"The Insulin Signaling System"; The Journal of Biological Chemistry by the American Society for Biochemistry and Molecular Biology, Inc.; Boston, Massachusetts; Jan. 7, 1994; vol. 269; pp. 1-4; By: Morris F. White and C. Ronald Kahn.

"The Nontransmembrane Tyrosine Phosphatase PTP-1B Localizes to the Endoplasmic Reticulum via Its 35 Amino Acid C-Terminal Sequence"; Boston, Massachusetts; Cell Press; Feb. 7, 1992; vol. 68; pp. 545-560 By: John V. Frangioni, Pamela H. Beahm, Victor Shifrin, Christine A. Jost, and Benjamin G. Neel.
"Dynamics of the interaction between the insulin receptor and protein tyrosine-phosphatase 1B in living cells"; Department of Cell Biology, Institut Cochin, CNRS, INSERM, Universite Paris V, Paris, France; European Molecular Biology Organization; Feb. 14, 2003; vol. 4; No. 3; pp. 313-319 By: Nicolas Boute, Samira Boubekeur, Daniele Lacasa and Tarik Issad.
"Imaging Sites of Receptor Dephosphorylation by PTP1B on the Surface of the Endoplasmic Reticulum"; SCIENCE; vol. 295; Mar. 1, 2002; pp. 1708-1711 By: Fawaz G. Haj, Peter J. Verveer, Anthony Squire, Benjamin G. Neel, and Philippe I. H. Bastiaens.
"Protein Tyrosine Phosphatase 1B Inhibitors for Diabetes"; Nature Publishing Group; Sep. 2002, vol. 1; pp. 696-709 By: Theodore O. Johnson, Jacques Ermolieff, and Michael R. Jirousek.
"Alterations in Skeletal Muscle Protein-Tyrosine Phosphatase Activity and Expression in Insulin-resistant Human Obesity and Diabetes"; The American Society for Clinical Investigation, Inc.; Jul. 1997; vol. 100; No. 2; pp. 449-458 By: Faiyaz Ahmad, John L. Azevedo, Jr., Ronald Cortright, G. Lynis Dohm, and Barry J. Goldstein.
"Improved Sensitivity to Insulin in Obese Subjects Following Weight Loss is Accompanied by Reduced Protein-Tyrosine Phosphatases in Adipose Tissue"; W.B. Saunders Company; Oct. 1997; vol. 46; No. 10; pp. 1140-1145 By: Faiyaz Ahmad, Robert V. Considine, Thomas L. Bauer, Joanna P. Ohannesian, Cheryl C. Marco, and Barry J. Goldstein.
"Protein-tyrosine Phosphatase-1B Negatively Regulates Insulin Signaling in L6 Myocytes and Fao Hepatoma Cells"; The Journal of Biological Chemistry; Mar. 30, 2001; vol. 276; No. 13; pp. 10207-10211 By: Katsuya Egawa, Hiroshi Maegawa, Shinya Shimizu, Katsutaro Morino, Yoshihiko Nishio, Michael Bryer-Ash, Anthony T. Cheung, Jay K. Kolls, Ryuichi Kikkawa, and Atsunori Kashiwagi.
"Osmotic Loading of Neutralizing Antibodies Demonstrates a role for Protein-tyrosine Phosphatase 1B in Negative Regulation of the Insulin Action Pathway"; The Journal of Biological Chemistry; Sep. 1, 1995; vol. 270; No. 35; pp. 20503-20508 By: Fiayaz Ahmad, Pei-Ming Li, Joseph Meyerovitch, and Barry J. Goldstein.
Increased Insulin Sensitivity and Obesity Resistance in Mice Lacking the Protein Tyrosine Phosphatase-1B Gene; SCIENCE; vol. 283; Mar. 5, 1999; pp. 1544-1548 By: Mounib Elchebly, Paul Payette, Eva Michaliszyn, Wanda Cromlish, Susan Collins, Ailsa Lee Loy, Denis Normandin, Alan Cheng, Jean Himms-Hagen, Chi-Chung Chan, Chidambaram Ramachandran, Michael J. Gresser, Michel L. Tremblay, and Brian P. Kennedy.

(Continued)

Primary Examiner — Kamal Saeed
Assistant Examiner — Nyeemah A Grazier
(74) Attorney, Agent, or Firm — Baker & Hostetler LLP

(57) ABSTRACT

PTP1B inhibitors with the following structure (formula I). Experiments indicate that these inhibitors can effectively inhibit the activity of protein tyrosine phosphatase 1B (PTP1B). They can be used as insulin sensitisers. They can be used to prevent, delay or treat diseases which are related to insulin antagonism mediated by PTP1B, especially diabetes type II and obesity. The invention also provides methods for preparing these inhibitors.

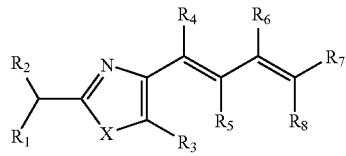

13 Claims, 1 Drawing Sheet

OTHER PUBLICATIONS

"Increased Energy Edpenditures, Decreased Adiposity, and Tissue-Specific Insulin Sensitivity in Protein-Tyrosine Phosphatase 1B-Deficient Mice"; American Society for Microbiology; Aug. 2000; pp. 5479-5489 By: Lori D. Klaman, Olivier Boss, Odile D. Peroni, Jason K. Kim, Jennifer L. Martino, Janice M. Zabolotny, Nadeem Moghal, Margaret Lubkin, Young-Bum Kim, Arlene H. Sharpe, Alain Stricker-Krongrad, Gerald I. Shulman, Benjamin G. Neel, and Barbara B. Kahn.

"Genomic characterization of the human and mouse protein tyrosine phosphatase-1B genes"; Elsevier Science B.V.; GENE 2000; vol. 260; 2000; pp. 145-153 By: Pontus K.A.L. Forsell, Yves Boie, Jacqueline Montalibet, Susan Collins, and Brian P. Kennedy.

"Depot-Specific Variation in Protein-Tyrosine Phosphatase Activities in Human Omental and Subcutaneous Adipose Tissue: A Potential Contribution to Differential Insulin Sensitivity"; The Journal of Clinical Endocrinology & Metabolism by the Endocrine Society; Dec. 2001, pp. 5973-5980 By: Xiandong Wu, Johan Hoffstedt, Wasim Deeb, Reetu Singh, Natalia Sedkova, Assaf Zilbering, Li Zhu, Pauline K. Park, Peter Arner, and Barry J. Goldstein.

"A P387L Variant in Protein tyrosine Phosphatase-1B (PTP-1B) Is Associated with type 2 Diabetes and Impaired Serine Phosphorylation of PTP-1B In Vitro"; DIABETES; Jan. 2002, vol. 51; pp. 1-6 By: Soren M. Echwald, Helle Bach, Henrik Bestergaard, Bjorn Richelsen, Kurt Kristensen, Thomas Drivsholm, Knut Borch-Johnsen, Torben Hansen and Oluf Pedersen.

"A Variation in 3' UTR of hPTP1B Increases Specific Gene Expression and Associates with Insulin Resistance"; The American Society of Human Genetics; Feb. 6, 2002; vol. 70; pp. 806-812 By: Rosa Di Paola, Lucia Frittitta, Guiseppe Miscio, Maura Bozzali, roberto Baratta, Marta Centra, Daniela Spampinato, Maria Grazia Santagati, Tonino Ercolino, Carmela Cisternino, Teresa Soccio, Sandra Mastroianno, Vittorio Tassi, Peter Almgren, Antonio Pizzuti, Riccardo Vigneri, and Vincenzo Trischitta.

"Novel Benzofuran and Benzothiophene Biphenyls as Inhibitors of Protein Tyrosine Phosphatase 1B with Antihyperglycemic Properties"; Journal of Medicinal Chemistry; American Chemical Society; Feb. 25, 2000; vol. 43; pp. 1293-1310 By: Michael S. Malamas, Janet Sredy, Christopher Moxham, Alan Katz, Weixin Xu, Robert McDevitt, Folake O. Adebayo, Diane R. Sawicki, Laura Seestaller, Donald Sullivan, and Joseph R. Taylor.

* cited by examiner

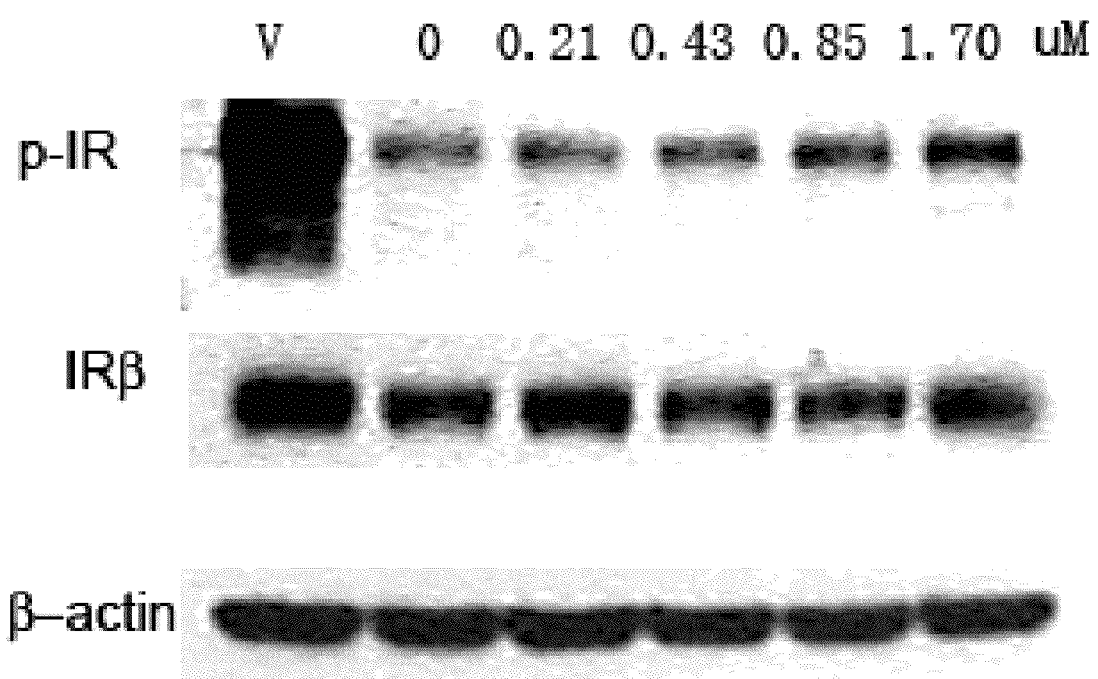

PROTEIN TYROSINE PHOSPHATASE 1B INHIBITOR, PREPARATION METHODS AND USES THEREOF

FIELD OF THE INVENTION

The present invention relates to a class of protein tyrosine phosphatase 1B (PTP1B) inhibitors, and in particular, to a class of novel organic compounds with small molecules which can be used as PTP1B inhibitors. The present invention also relates to a process for producing such inhibitors, and the uses thereof as insulin sensitisers in preventing, delaying or treating diseases which are related to diseases mediated by PTP1B, especially type II diabetes and obesity.

BACKGROUND OF THE INVENTION

Diabetes mellitus is a group of clinical syndromes induced by the genetic and environmental interactions, and involves a series of metabolic disorders in carbohydrate, protein, fat, water, electrolyte, etc. due to absolute or relative deficiencies in insulin secretion and reduced insulin sensitivity of the target tissue cells. Clinically, diabetes mellitus is mainly characterized by hyperglycemia, and may lead to various complications, such as blindness, cardiovascular diseases, kidney damage, and the like, as time goes on, and acute metabolic disorders such as ketoacidosis etc. may occur in serious conditions and stress. Therefore, diabetes mellitus and complications thereof have been worldwide public health problems that severely threaten human health.

Diabetes mellitus is mainly classified into two types, namely type I diabetes mellitus (insulin-dependent diabetes mellitus, IDDM) and type II diabetes mellitus (non-insulin-dependent diabetes mellitus, NIDDM). Type I diabetic patients have abnormal response to stimuli of environmental factors due to genetic susceptibility determined by HLA-D gene in the short arm of chromosome 6, which leads to the destruction of the pancreatic beta-cells through autoimmune response, and thus the insulin is absolutely deficient. Hence, the type I patients have to rely on insulin therapy to maintain their lives. The type II diabetes mellitus which accounts for 90% or more in the diabetic patients is caused by the relative deficiencies in insulin secretion and/or insulin resistance. Type II diabetes mellitus is also strongly affected by genetic factors, and shows significant heterogeneity, that is, its pathogenesis is varied and complicated, and there are great differences among type II diabetic patients.

Type II diabetes mellitus is accompanying with the decrease in insulin sensitivity of tissues sensitive to insulin, i.e. insulin resistance, which is because the insulin signal is weakened or disordered during the transduction, resulting the impaired glucolipids metabolism in muscle, liver and adipose tissues. During the signal transduction in the insulin signaling pathway, the insulin secreted into body fluid binds with the insulin receptor (IR) subunits of the cells sensitive to insulin first. After IRs form dimers, the subunits phosphorylate the tyrosines at the active sites by auto-phosphorylation, thus activating the protein tyrosine kinase (PTK) of the IR subunits. Then adapter proteins containing SH2 domain, such as insulin receptor substrate (IRS) 1-4, are recruited to the SH2 binding sites of the IR, and PI3Ks are activated. After that, the PKBs and GLUT4s in the downstream glucose metabolism pathway are further activated, and the glucolipids metabolism in body is initialized. During the signal transduction, an important regulating mechanism is the reversible regulation of the protein tyrosine phosphorylation of IR, IRS and other downstream molecules (White M. F., Kahn C. R.; J. Bio. Chem., 1996, 269, 1-4): the activated phosphorylated IRs are internalized, migrated to endoplasmic reticulum and de-phosphorylated by a specific tyrosine phosphatase (PTPase) such as PTP1B to lose their activity, thus terminating the insulin signal. Therefore, it can be seen that, the impaired enzyme activity between the specific PTPases and the PTKs in insulin pathway may be the reason to cause the insulin resistance of the type II diabetes mellitus. Thus, it has been a more and more important approach for treating type II diabetes mellitus by inhibiting the activity of PTPases through searching an inhibitor which selectively acts on the PTPases in the pathway to enhance and prolong the insulin signal.

PTPases include a large family of transmembrane receptor and intracellular non-receptor type enzymes. The intracellular protein tyrosine phosphatase 1B (PTP1B) is one of PTPases that is first purified and determined the biological properties. It is about 50 kDa in length, and has a cutable hydrophobic segment with 35 amino acids at its C end. The segment is responsible for locating PTP1Bs in endoplasmic reticulum (Frangioni J. V., Beahm P. H., Shifrin V., et al.; Cell, 1992, 68, 544-560). The PTP1Bs located in endoplasmic reticulum are dephosphorylated by interacting with receptor type kinases such as IR, EGFR (epidermal growth factor receptor) and PDGFR (platelet-derived growth factor receptor) (Boute N., Boubekeur S., Lacasa D., et al.; EMBO Rep., 2003, 4(3), 313-319; Haj F. G., Verveer P. J., Squire A., et al.; Science, 2002, 295(5560), 1708-1711).

Experimental results show that PTP1B plays a key role in negatively regulating the kinase activity of IR and the phosphorylation level of IRS (Johnson T. O., Ermolieff J., Jirouesk M. R.; Nat. Rev. Drug disc., 2002, 1(9), 696-709). PTP1B is generally expressed in the tissues sensitive to insulin, and its protein expression and phosphatase activity are higher in the skeletal muscles and adipocytes of abetic peoples and rodent animals suffering insulin resistance than in control group, which shows that the improved PTP may have an important function during the pathological process of insulin resistance (Ahmad F., Azevedo J. L., Cortright R., et al.; J. Clin. Invest., 1997, 100(2), 449-458; Ahmad F., Considine R. V., Bauer T. L., et al.; Metabolism, 1997, 46(10), 1140-1145). The high expression of PTP1B in L6 muscle cells and Fao cells by adenovirus-mediated gene transfection, can significantly suppress the phosphorylation levels of IR and IRS-1 which are induced by insulin, thereby inhibiting the transduction of the downstream pathway thereof and the final glyconeogenesis (Egawa K. et al.; J. Biol. Chem., 276(13), 10207-10211). By treating rat hepatocytes KRC-7 with a specific neutralizing antibody of PTP1B, Ahmad et al. found that the sensitivity of the insulin signaling pathway could be improved by inhibiting the activity of intracellular PTP1B with the antibody, and the phosphorylation levels of IR and IRS-1 and the PI3K activity of the downstream pathway thereof can also be increased apparently (Ahmad F., et al.; J. Biol. Chem., 1995, 170(35), 20503-20508).

A more important experimental evidence comes from PTP1B knockout mice. It is reported by Elchebly et al. that the PTP knockout mice produced by homologous recombination can maintain their normal physiological conditions, and have significantly enhanced insulin sensitivity, which are related to the enhanced phosphorylation levels of IR and IRS-1 in liver and skeletal muscle (Elchebly M., et al.; Science, 283, 1544-1548). Surprisingly, PTP1B knockout mice are also capable to a certain extent of resisting the weight gain and insulin resistance induced by food, which is because the adipocyte volume decreases without varying the amount of the adipocytes and the in vivo energy metabolism rate increases (Klaman L. D., et al. Mol. Cell. Bio., 20(15), 5479-

5489). These prove the important roles of PTP1B in insulin sensitivity, energy consumption and fat storage.

There are increasing genetic evidences showing that PTP1B is related to insulin resistance, obesity, type II diabetes, and the like, with the progress in Human Genome Project. The human protein tyrosine phosphatase 1B (hPTP1B) gene is located in 20q13.1-13.2 of human chromosome, and has 10 exons with two splicing forms, wherein one contains only the previous 9 exons and the other includes all the 10 exons. Both expressions of the two forms are regulated by the insulin signal itself (Forsell P. A., Boie Y., Montalibet T., et al.; Gene, 2003, 260(1-2), 145-153). It was found that the insulin sensitivity of retinal adipose tissue decreased when PTP1B was over-expressed and had excessive activity in the tissue, resulting in insulin resistance in the whole body (Wu X. D., et al.; J. Clin. Endocrinol Metab, 2001, 86, 5973-5980). It is found that a inserional mutation in some people can improve the stability of PTP1B mRNA, and thus increase the expression level of PTP 1 B, while it is often accompanied with insulin resistance and the increase of triglyceride and high-density lipoprotein (HDL) in these people (Echwald S. M., et al.; Diabetes, 2002, 51, 1-6). In addition, a rare Pro387/Leu mutation was found and it can prevent Ser in the PTP1B regulating sequence from being phosphorylated, and result in a relatively high enzyme activity of PTP1B on average. The probability of these people to suffer type II diabetes is 3.7 folds higher than that of normal people (Echwald S. M., et al.; Diabetes, 2002, 51, 1-6). Single nucleotide polymorphism (SNP) of 981T/981C located in exon No. 8 was found in OJI-OREE people, while the risk of these people to suffer type II diabetes and impaired glucose tolerance (IGT) is 42% lower than that of normal people, which is due to the relatively low enzyme activity of PTP1B on average (Di Paoia R., et al.; Am. J. Hum. Genet., 2002, 70, 806-812).

In summary, PTP1B is a novel potential target for treating diabetes and obesity. The therapeutic effect for diabetes and obesity will be greatly improved by repressing the PTP1B activity in the tissues sensitive to insulin. Therefore, it has a wide application prospect for selecting a specific inhibitor against PTP1B.

Some progresses have been made in the study on the selective inhibitors against PTP1B. However, most of the selective inhibitors are limited to some peptide or peptoid compounds, such as EEDE(F2PMP)M (Ki=7.2 nM) and Glu-F2PMP-F2PMP (IC50=40 nM) which are inhibitors designed based on the sequence of the de-phosphorylating substrate of PTP1B. It is hard for these peptide inhibitors to be drugs due to the fact that they are peptide phosphate compounds, although they have a relatively strong inhibiting activity and a relatively high selectivity. Recently, a series of PTP1B inhibitors which are non-peptide non-phosphate compounds were reported that they have certain selectivity. More importantly, some of the compounds have significant activity on reducing the glucose and insulin levels in the blood plasma of ob/ob mice. This is the first direct evidence in pharmacology showing that PTP inhibitors have an activity for treating diabetes (Malamas, M. S., et al. J. Med. Chem., 2000, 43, 1293-1310). These results provide a potential without doubt to find novel small molecular non-peptide organic compounds to be used as PTP1B inhibitors with high activity and selectivity.

SUMMARY OF THE INVENTION

One object of the present invention is to provide a class of small molecular organic compounds as PTP 1B inhibitors.

Another object of the present invention is to provide a process for producing such compounds.

A further object of the present invention is to provide a use of such compounds as insulin sensitisers in preventing, delaying or treating diseases which are related to diseases mediated by PTP 1B, especially type II diabetes and obesity.

In order to achieve the above objects, there is provided a compound having a structure represented by the following formula I,

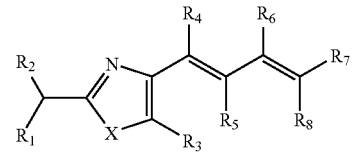

wherein X is S, O, NH or CH=CH;

$R_1$ is $OCOR_9$, $OCOCOR_9$, $NHCOR_9$, $NHCOCOR_9$, $NHCONHR_9$,

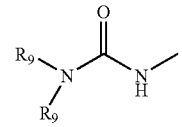

or $CH_2R_9$, wherein, $R_9$ and $R_9'$ are each independently C2-C6 alkenyl; C1-C2 alkoxycarbonyl; C3-C6 cycloalkyl, or C3-C6 cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl, or ethoxycarbonyl; or $CH_2OR_{13}$, wherein, $R_{13}$ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl substituted by O, N and/or S;

$R_2$ is H; halogen; C2-C6 alkenyl; C1-C2 alkoxycarbonyl; C3-C6 cycloalkyl, C3-C6 cycloalkyl substituted by halogen or carboxyl, or 5- or 6-membered cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl or ethoxycarbonyl; mercapto, oxy, amino, C1-C6 alkyl or C2-C6 alkenyl which are substituted by unsubstituted or substituted aryl;

$R_3$ is H; halogen; C2-C6 alkenyl; C1-C2 alkoxycarbonyl; C3-C6 cycloalkyl, C3-C6 cycloalkyl substituted by halogen or carboxyl, or 5- or 6-membered cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl or ethoxycarbonyl; preferably H or phenyl;

$R_4$, $R_5$, $R_6$ and $R_7$ are each independently H; halogen; C2-C6 alkenyl; C3-C6 cycloalkyl; phenyl or halogenated phenyl; benzyl; C1-C13 alkyl substituted by halogen, C1-C6 alkoxyl or hydroxyl; C1-C4 alkyl having carboxyl, methoxycarbonyl or ethoxycarbonyl; preferably H or methyl;

wherein, the double bond between $R_4$ and $R_5$ can be in a cis- or trans-configuration; and the double bond between $R_6$ and $R_7$ can be in a cis- or trans-configuration;

$R_8$ is C1-C4 alkyl having carboxyl, methoxycarbonyl or ethoxycarbonyl; preferably ethoxycarbonyl or carboxyl.

In particular, $R_3$ is preferably H or phenyl; $R_4$, $R_5$, $R_6$ and $R_7$ are each independently and preferably H, C1-C4 alkyl, more preferably H or methyl; $R_8$ is preferably C1-C4 alkyl having carboxyl, methoxycarbonyl or ethoxycarbonyl, more preferably ethoxycarbonyl or carboxyl.

The compound according to the present invention may have a structure represented by the following formula II,

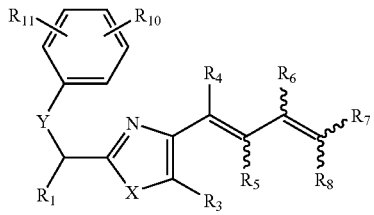

II wherein X, $R_1$ and $R_3$-$R_8$ are the same as defined in the compound I;

Y is S, O or NH; C1-C6 alkyl; C2-C6 alkenyl;

$R_{10}$ is H; halogen; hydroxyl; C2-C6 alkenyl; C1-C13 alkyl substituted by halogen, C1-C6 alkoxyl, phenyl, benzyloxy or hydroxyl; phenyl, naphthyl, or phenyl substituted by halogen, carboxyl, C1-C6 alkyl or alkoxyl; benzyl, or benzyl substituted by halogen, C1-C6 alkyl or alkoxyl; C1-C4 alkyl having carboxyl, methoxycarbonyl or ethoxycarbonyl; $OCH_2R_{12}$ or $OR_{12}$, wherein, $R_{12}$ is H; C2-C6 alkenyl; C1-C13 alkyl substituted by halogen, C1-C6 alkoxyl, phenyl or hydroxyl; C1-C4 alkyl having carboxyl, methoxycarbonyl or ethoxycarbonyl; thiazolyl, furyl, thienyl, pyranyl, pyridyl, benzothiazolyl, benzothienyl, naphthyl; benzyl; phenyl, or phenyl substituted by halogen, C1-C6 alkoxyl or hydroxyl; C3-C6 cycloalkyl, or 5- or 6-membered cycloalkyl substituted by O, N and/or S, In particular, $R_{10}$ can be H; —OH; phenyl; —OCH$_3$; —OCH$_2$CH═CH$_2$; —OCH$_2$COOEt; —OCH$_2$COOH; —OBn; 2-ethoxycarbonylethoxy; 2-hydroxylethoxy; butoxy; 4-cyanobenzyloxy; 4-fluorobenzyloxy; 4-methoxybenzyloxy; 3-fluorobenzyloxy; 2-fluorobenzyloxy; 2-naphthylmethoxy; 4-nitro-2-fluorophenoxy; phenylethoxy; 1-pyridylmethoxy; 4-pyridylmethoxy; 2-furylmethoxy; 2-pyranylmethoxy;

$R_{11}$ is H; hydroxyl; halogen; C1-C6 alkyl; C1-C6 alkoxyl; preferably H.

The compound according to the present invention may have a structure represented by the following formula III,

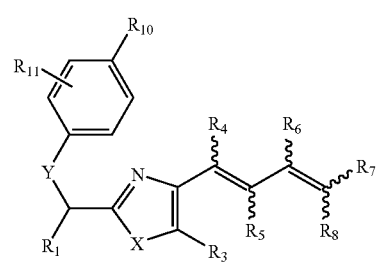

III wherein X, $R_1$, $R_3$-$R_8$, Y and $R_{10}$-$R_{11}$ are the same as defined in the compound II.

In particular, in the above formulas II and III,

Y is preferably —CH$_2$—;

$R_{10}$ is preferably H; hydroxyl; phenyl; —OCH$_3$; —OCH$_2$CH═CH$_2$; —OCH$_2$COOEt; —OCH$_2$COOH; —OBn; 2-ethoxycarbonylethoxy; 2-hydroxylethoxy; butoxy; 4-cyanobenzyloxy; 4-fluorobenzyloxy; 4-methoxybenzyloxy; 3-fluorobenzyloxy; 2-fluorobenzyloxy; 2-naphthylmethoxy; 4-nitro-2-fluorophenoxy; phenylethoxy; 1-pyridylmethoxy; 4-pyridylmethoxy; 2-furylmethoxy; 2-pyranylmethoxy;

$R_{11}$ is preferably H.

The compound according to the present invention may have a structure represented by the following formula IV,

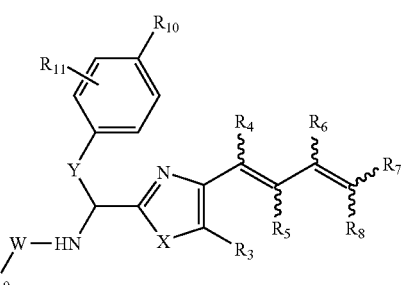

IV wherein X, $R_3$-$R_8$, Y and $R_{10}$-$R_{11}$ are the same as defined in the compound III;

$R_9$ is C2-C6 alkenyl; C1-C2 alkoxycarbonyl; C3-C6 cycloalkyl, or C3-C6 cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl or ethoxycarbonyl; or $CH_2OR_{13}$;

wherein, R₁₃ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl substituted by O, N and/or S;

W is CO, CO—CO, CO—NH or CO—NR₉';

wherein, R₉' is C2-C6 alkenyl; C1-C2 alkoxycarbonyl; C3-C6 cycloalkyl, or C3-C6 cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl or ethoxycarbonyl; or CH₂OR₁₃;

wherein, R₁₃ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl substituted by O, N and/or S.

The compound according to the present invention may have a structure represented by the following formula V or VI,

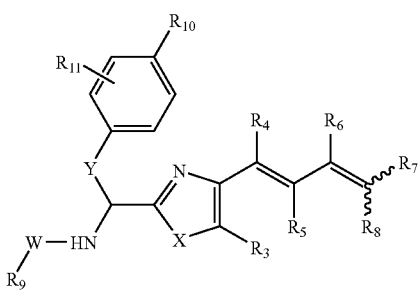

V

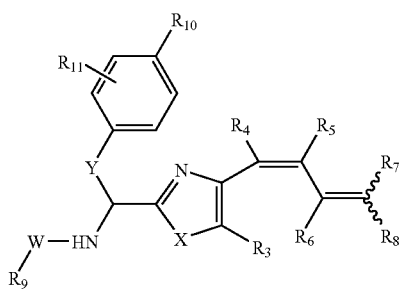

VI wherein X, W, Y, R₃-R₈, R₉ and R₁₀-R₁₁ are the same as defined in the compound IV.

The compound according to the present invention may have a structure represented by the following formula VII,

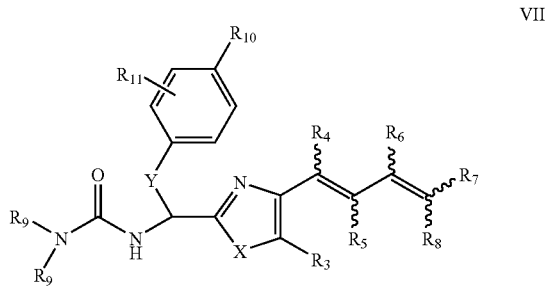

VII wherein X, Y, R₃-R₈, R₉ and R₁₀-R₁₁ are the same as defined in the compound V or VI;

R₉' is C2-C6 alkenyl; C1-C2 alkoxycarbonyl; C3-C6 cycloalkyl, or C3-C6 cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl or ethoxycarbonyl; or CH₂OR₁₃;

wherein, R₁₃ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl substituted by O, N and/or S.

In particular, in the formulas IV-VII,

R₃ is preferably H or phenyl;

R₄, R₅, R₆ and R₇ are each independently and preferably H or C1-C4 alkyl, more preferably H or methyl;

R₈ is preferably C1-C4 alkyl having carboxyl, methoxycarbonyl or ethoxycarbonyl, more preferably ethoxycarbonyl or carboxyl;

R₉ is C2-C6 alkenyl; C1-C2 alkoxycarbonyl; C3-C6 cycloalkyl, or C3-C6 cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzo-fused 5- or 6-membered aromatic cyclic group substituted by O, N and/or S; C1-C4 alkyl having carboxyl, methoxycarbonyl or ethoxycarbonyl;

Y is preferably —CH₂—;

W is preferably CO;

R₁₀ is preferably H; hydroxyl; phenyl; —OCH₃; —OCH₂CH═CH₂; —OCH₂COOEt; —OCH₂COOH; —OBn; 2-ethoxycarbonylethoxy; 2-hydroxylethoxy; butoxy; 4-cyanobenzyloxy; 4-fluorobenzyloxy; 4-methoxybenzyloxy; 3-fluorobenzyloxy; 2-fluorobenzyloxy; 2-naphthylmethoxy; 4-nitro-2-fluorophenoxy; phenylethoxy; 1-py ridylmethoxy; 4-pyridylmethoxy; 2-furylmethoxy; 2-pyranylmethoxy;

$R_{11}$ is preferably H.

The compound according to the present invention may have a structure represented by the following formula VIII,

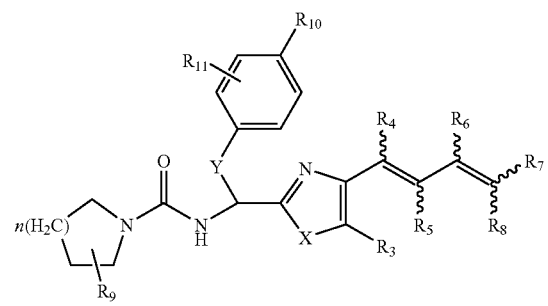

wherein X, Y, $R_3$-$R_9$, $R_9$ and $R_{10}$-$R_{11}$ are the same as defined in the compound V or VI, and $R_9$ is preferably C2-C6 alkenyl; C1-C2 alkoxycarbonyl; C3-C6 cycloalkyl, or C3-C6 cycloalkyl substituted by O, N and/or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubtituted phenyl, substituted or unsubtituted benzyl, 5- or 6-membered aromatic cyclic group substituted by O, N and/or S, C3-C6 cycloalkyl, C3-C6 cycloalkyl substituted by O, N and/or S, or hydroxyl; 5- or 6-membered aromatic cyclic group substituted by O, N and/or S, or benzofused 5- or 6-membered aromatic cyclic group substituted by O, N and/or S; C1-C4 alkyl having carboxyl, methoxycarbonyl or ethoxycarbonyl;

n=0, 1, 2, 3, preferably 0.

The compound according to the present invention is preferably

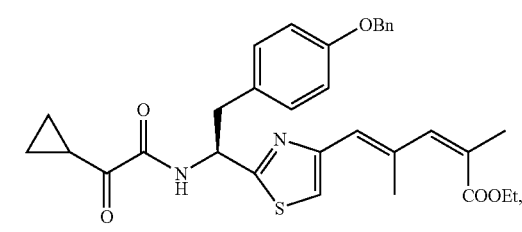

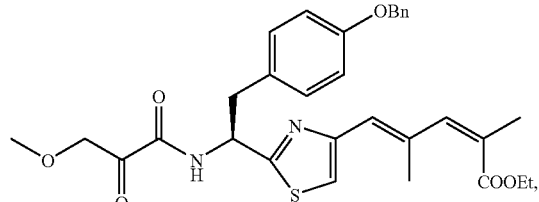

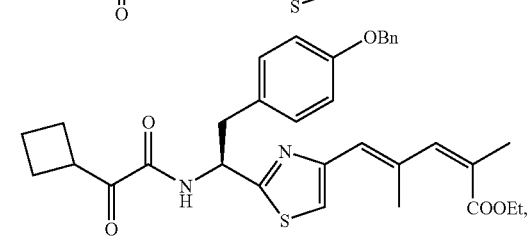

-continued

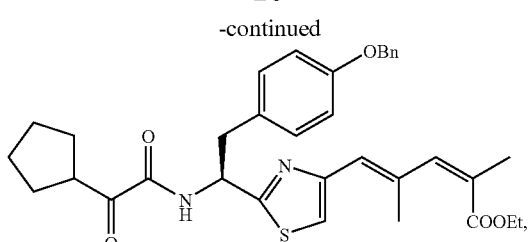

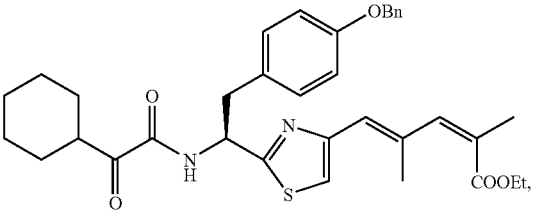

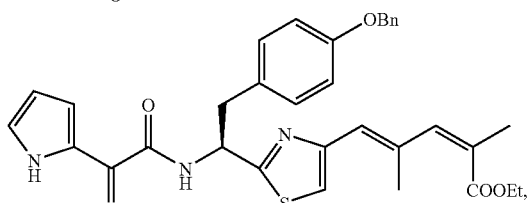

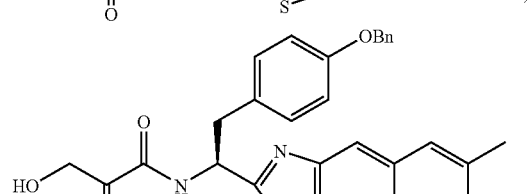

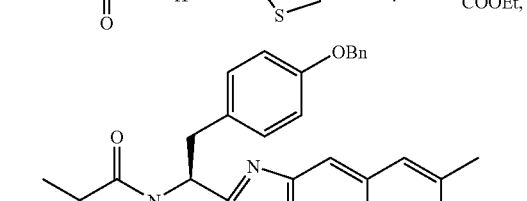

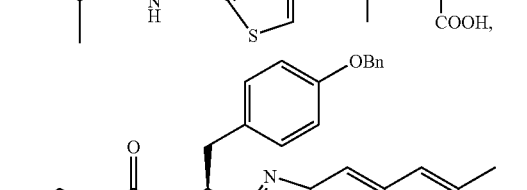

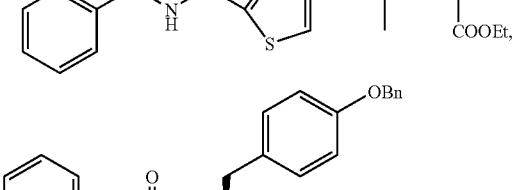

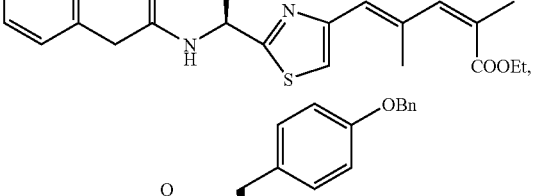

-continued

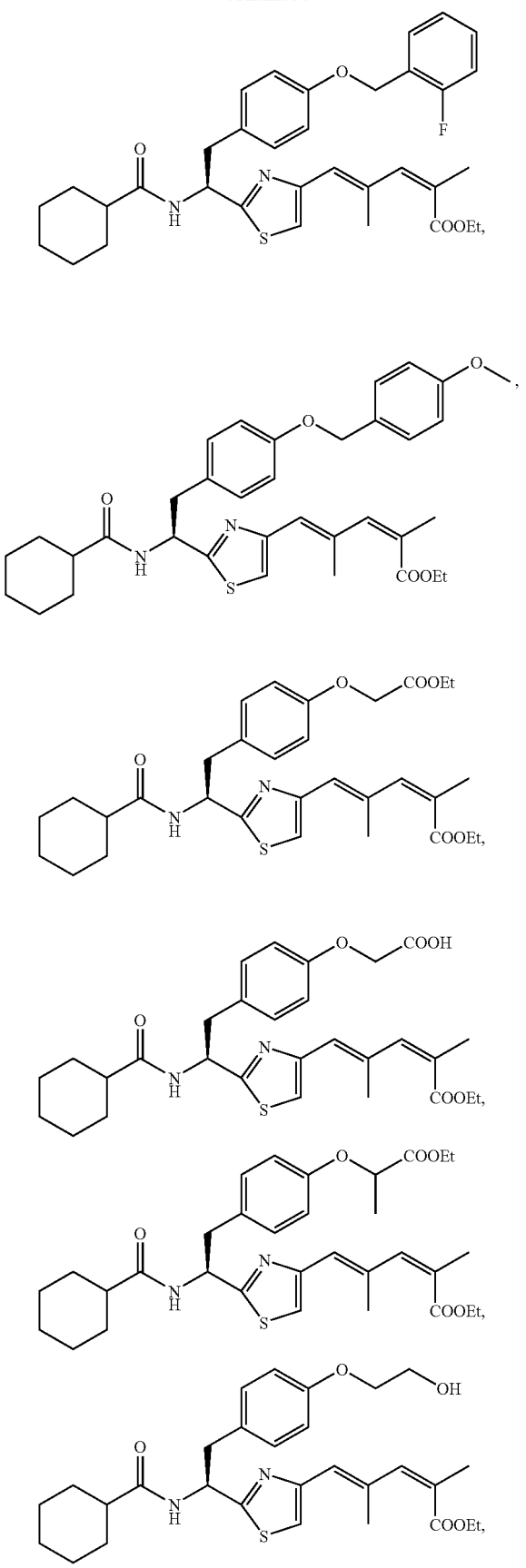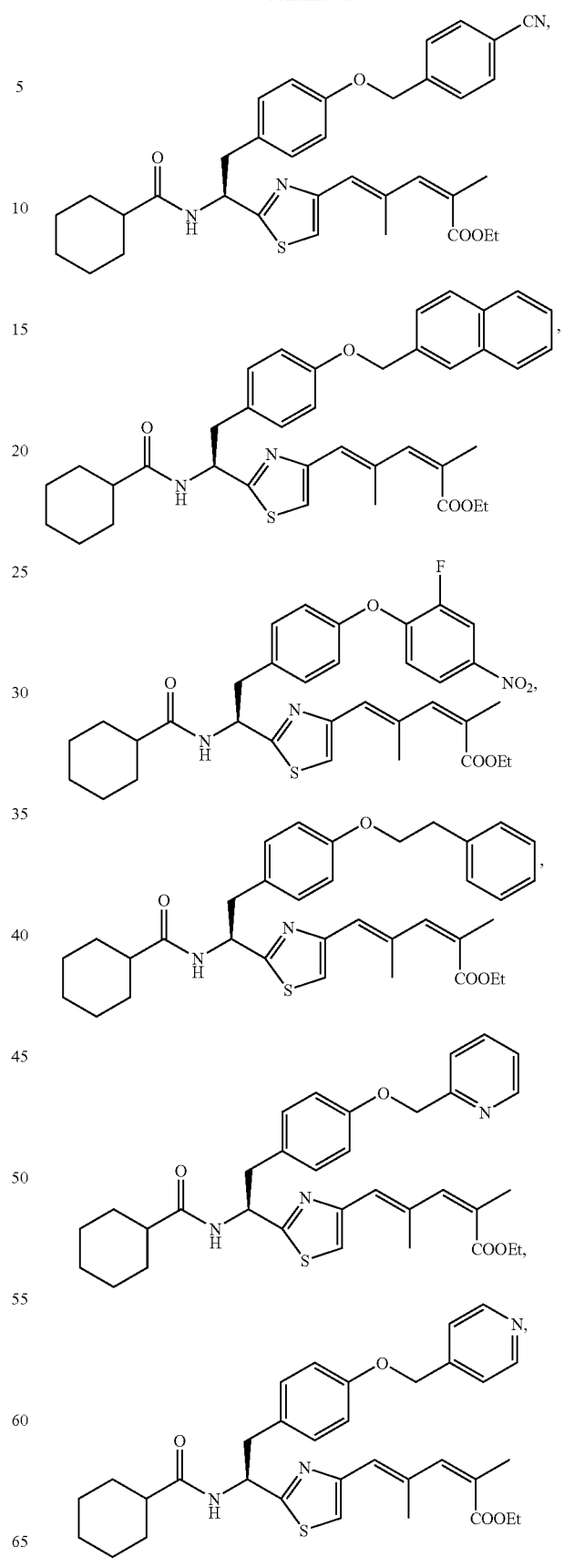

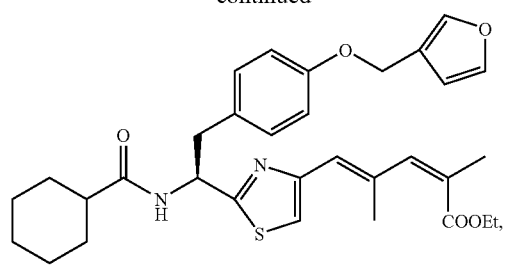
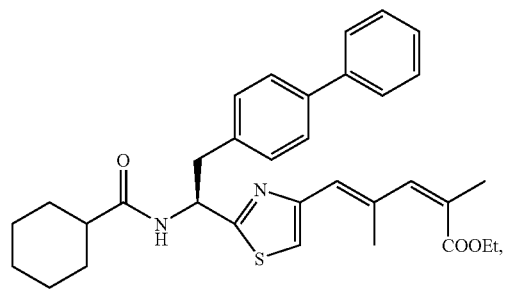
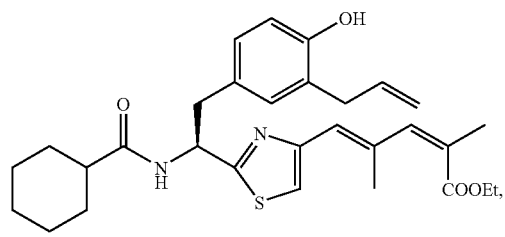
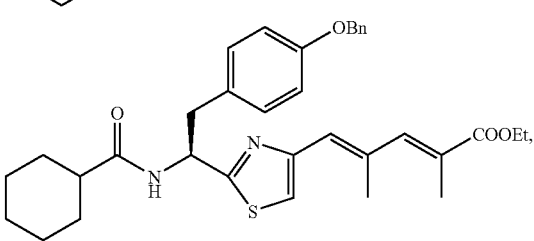
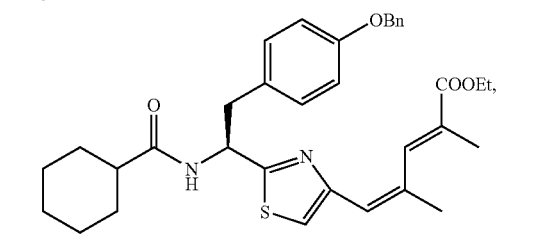
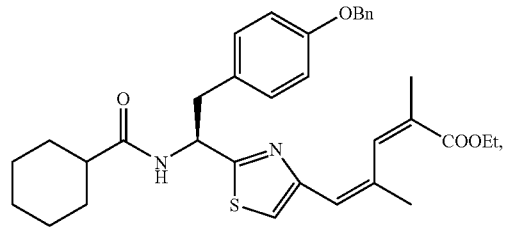
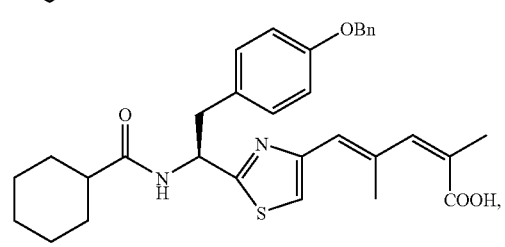
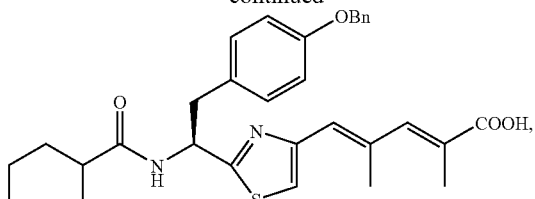
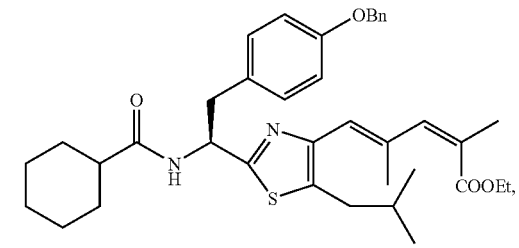
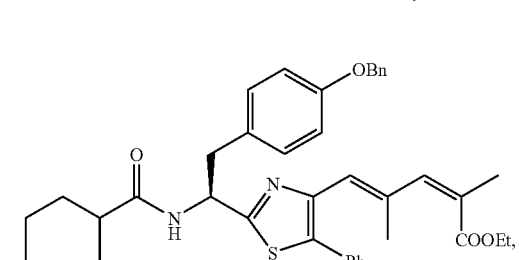
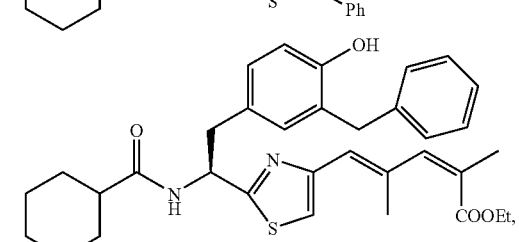
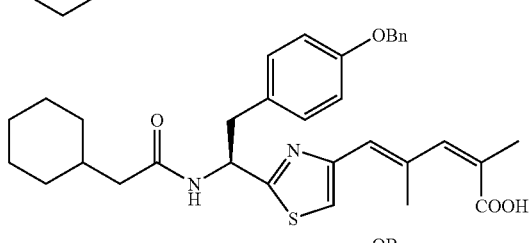
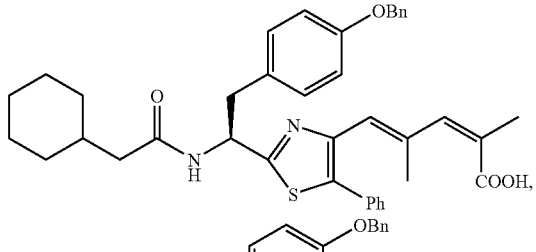
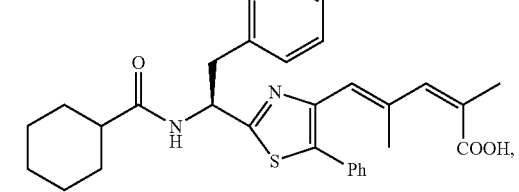

-continued
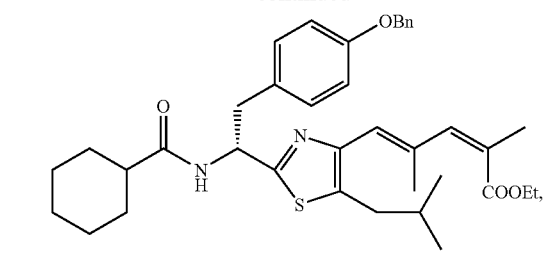
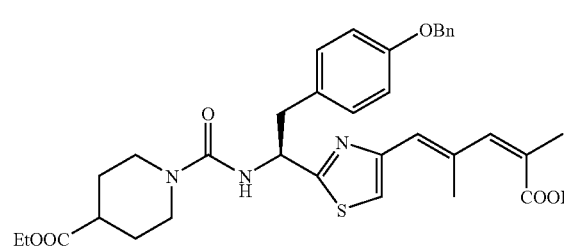
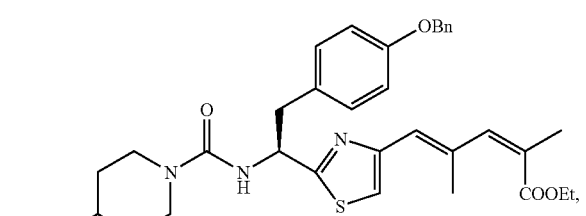
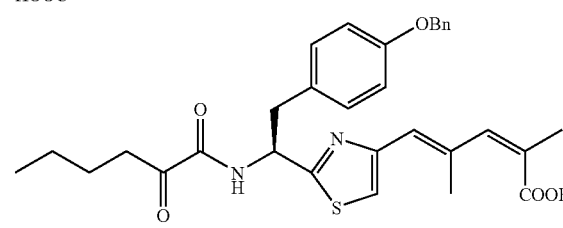
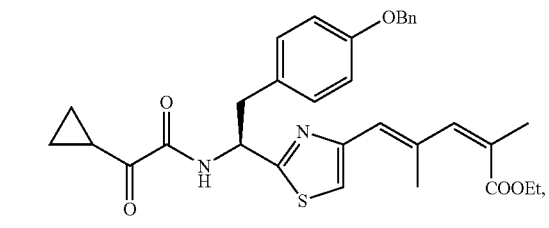
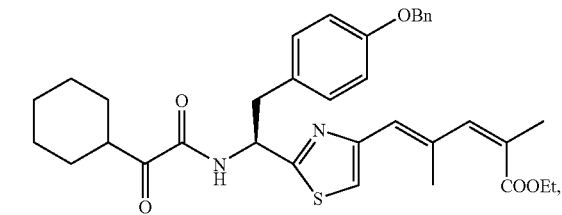
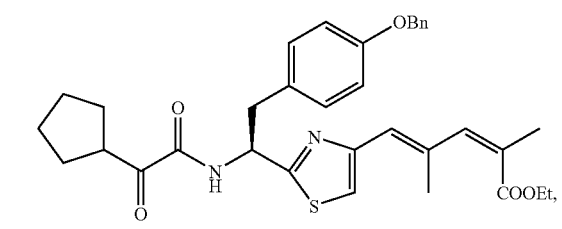
-continued
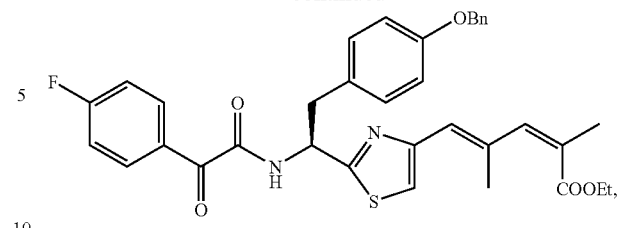
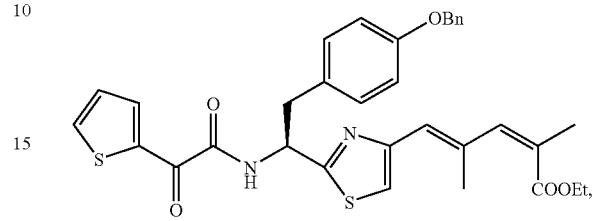
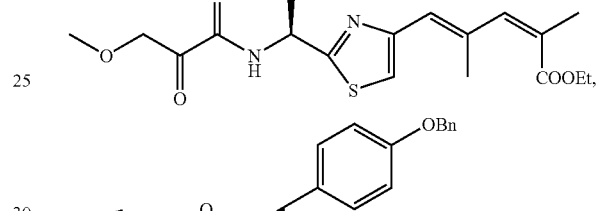
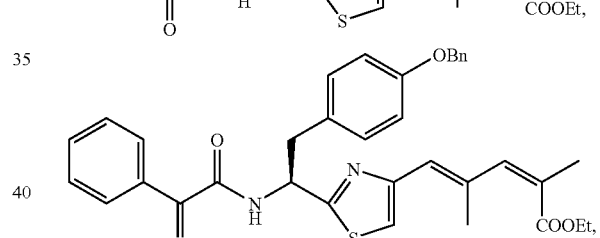
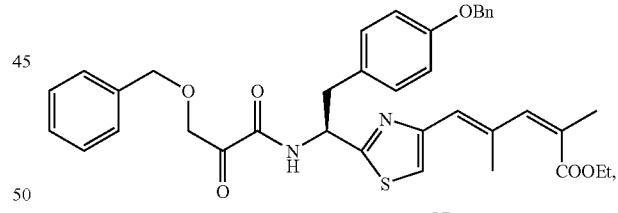
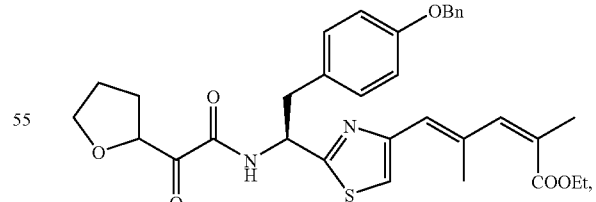
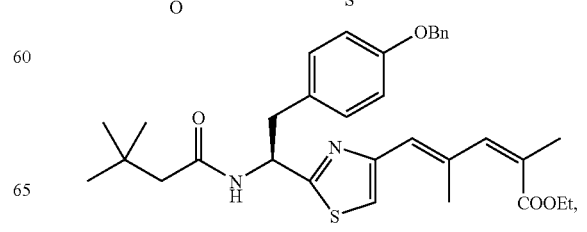

-continued
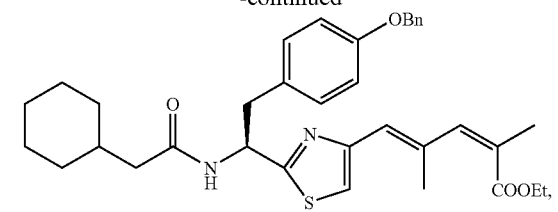
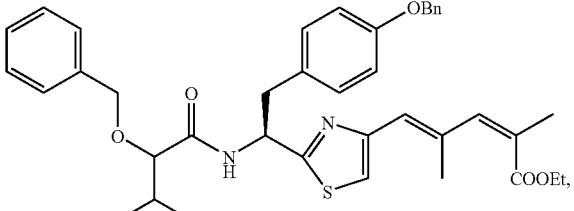
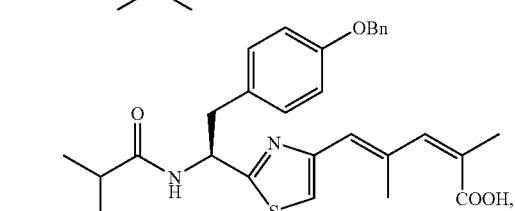
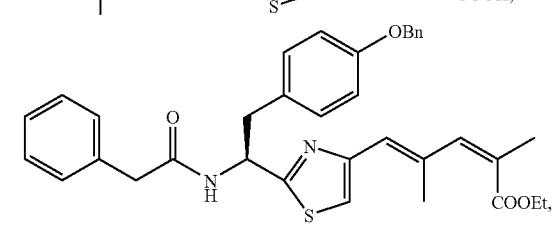
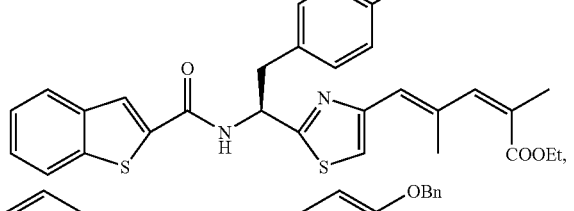
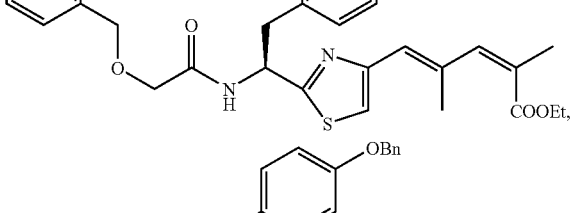
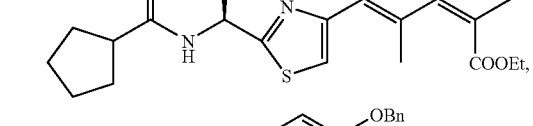
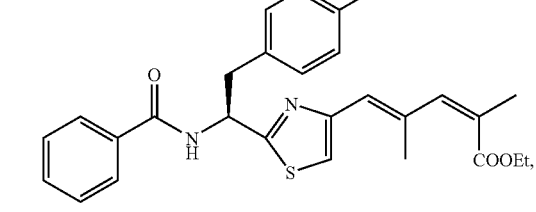
-continued
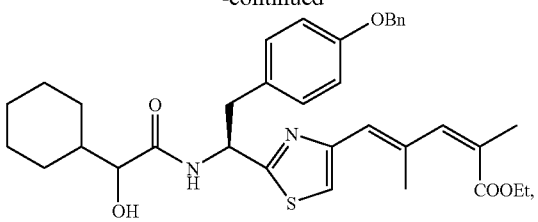
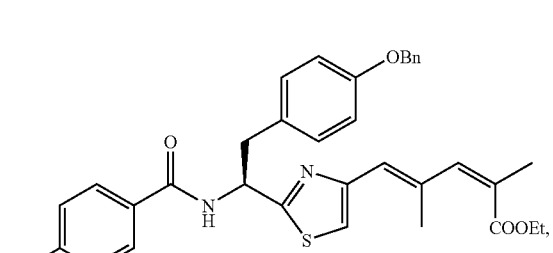
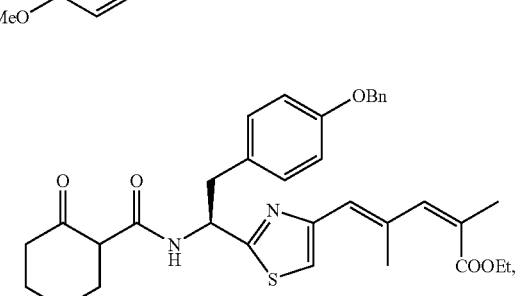
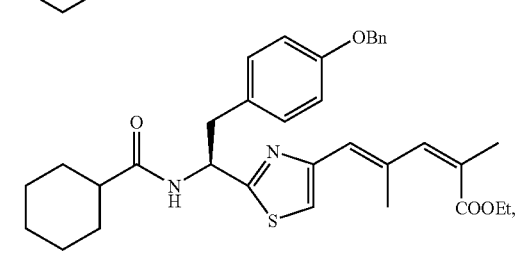
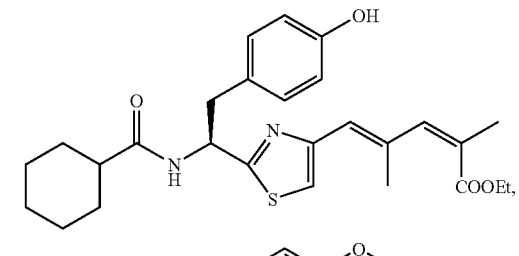
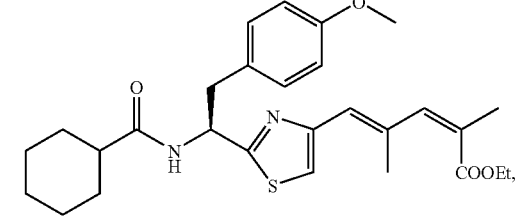
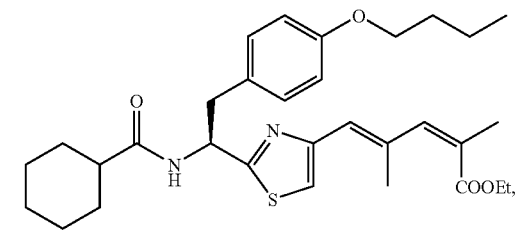

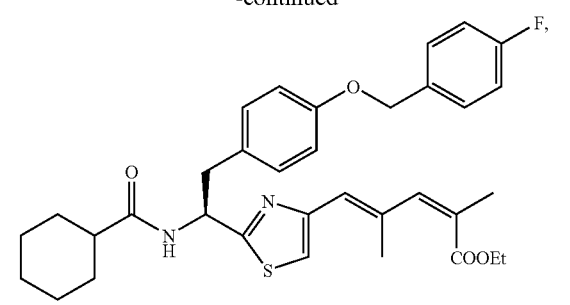
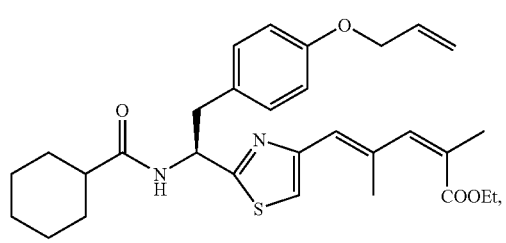
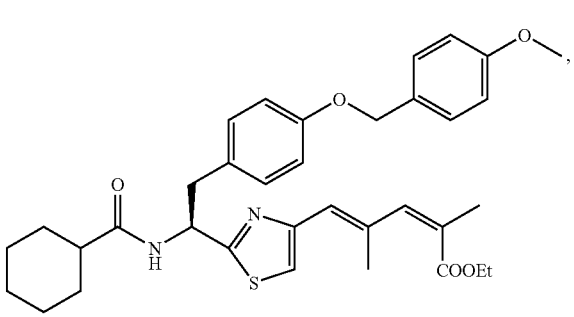
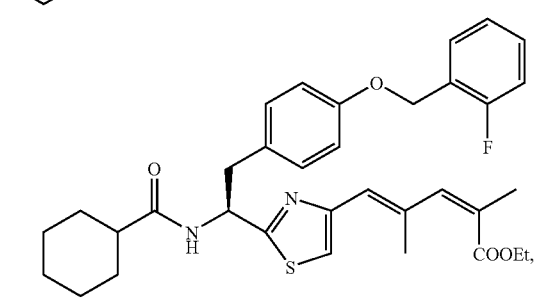
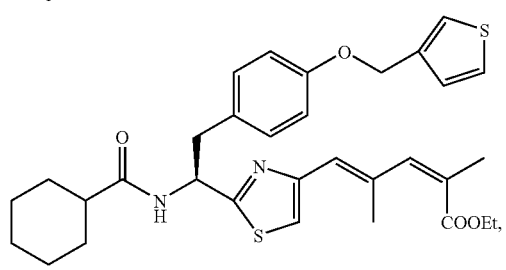
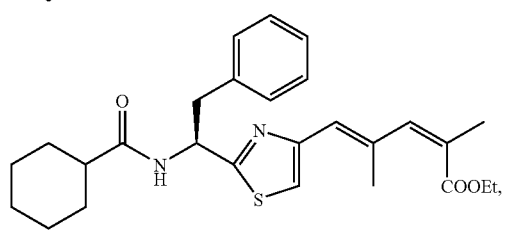
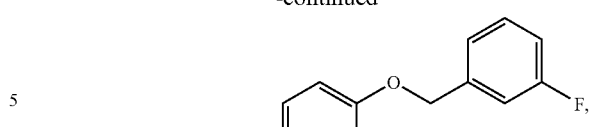
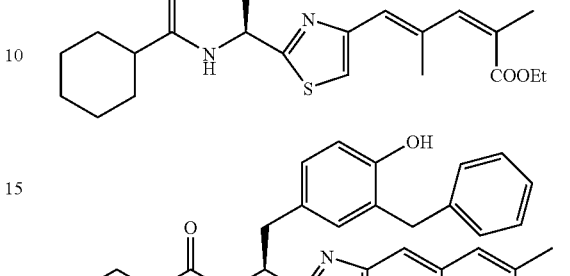
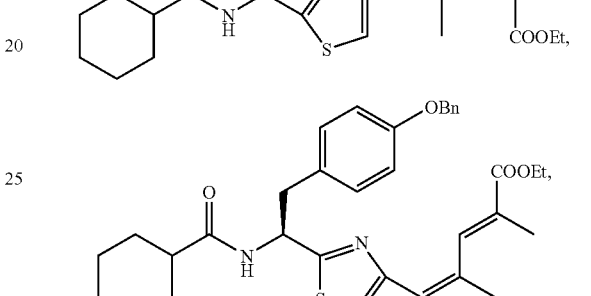
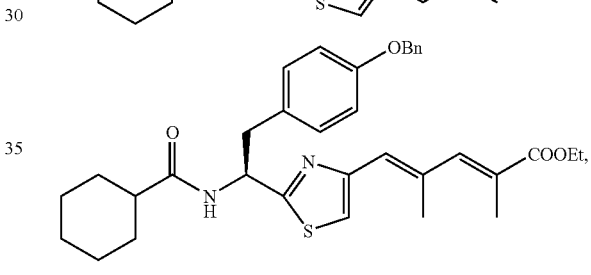
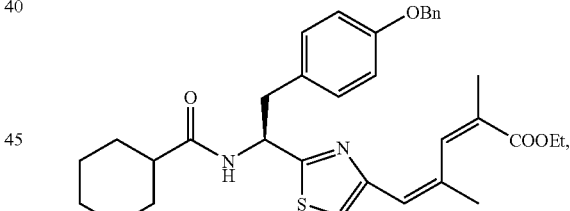
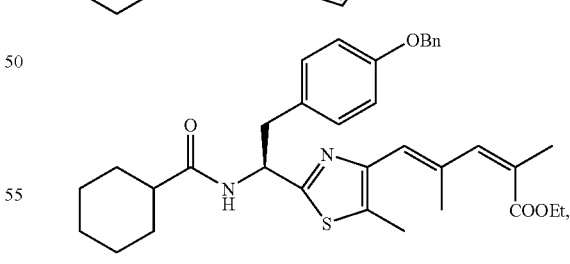
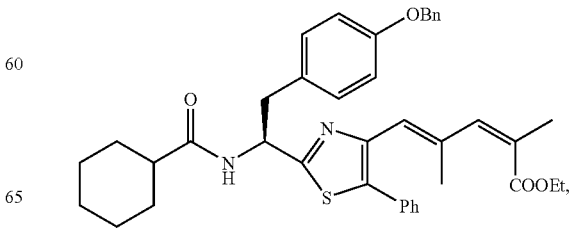

-continued

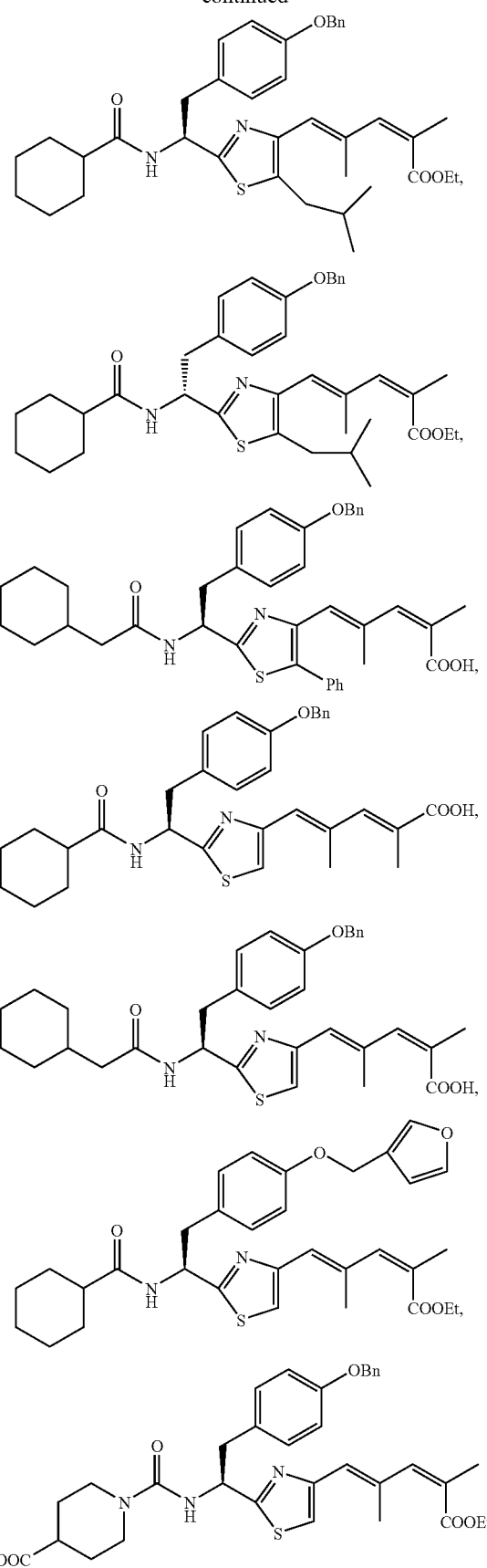

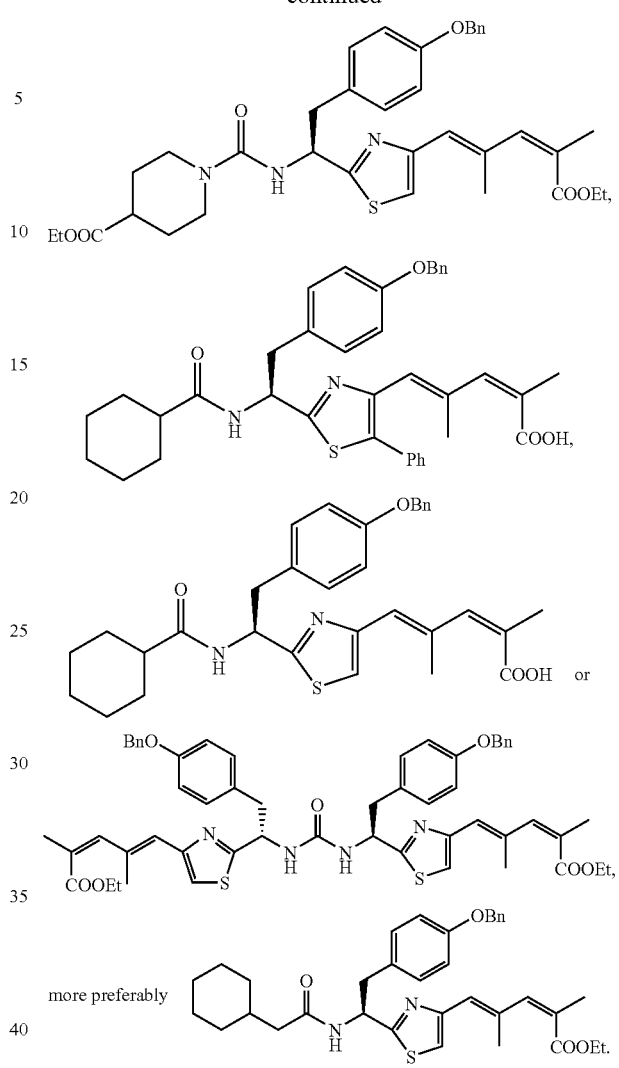

more preferably

The present invention further provides a process for preparing the above compounds, comprising:

Step 1: as illustrated in the following reaction scheme, a carboxylic compound 1 was coupled with a primary amine hydrochloride compound 2 at room temperature using dichloromethane as a solvent to produce the compound 3. Then the compound 3 was cyclized under refluxing using tetrahydrofuran as a solvent to obtain an aromatic cyclic thiazole compound 4 wherein X is S in the presence of Lawssen reagent, or to obtain an aromatic cyclic oxazole compound 4 wherein X is O in the presence of phosphorus oxychloride, or to obtain an aromatic cyclic imidazole compound 4 wherein X is NH in the presence of acetic acid and sodium acetate;

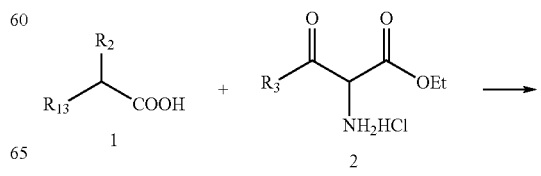

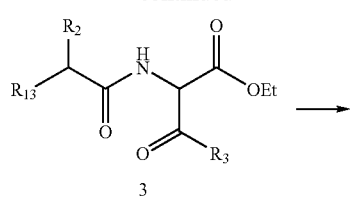

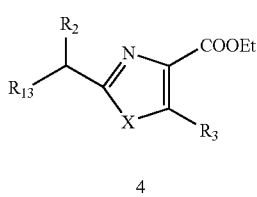

Step 2: as illustrated in the following reaction scheme, the ethoxycarbonyl-substituted aromatic cyclic compound 4 was reduced by diisobutyl aluminium hydride at −78° C. using dichloromethane as a solvent to obtain a corresponding aldehyde compound 5. Then the formaldehyde-substituted aromatic cyclic compound 5 was reacted with a Grignard reagent under room temperature or heating using tetrahydrofuran as a solvent to afford a corresponding sec-alcohol compound 6. After the sec-alcohol compound 6 was oxidized by IBX at 50° C. using toluene and dimethylsulfoxide as solvents to a corresponding ketone compound 7, the ketone compound 7 was finally reacted with Wittig-Horner reagent at a temperature in the range of 0° C. to room temperature using tetrahydrofuran as a solvent to provide an α,β-unsaturated ethyl carboxylate compound 8 in the cis- or trans-configuration;

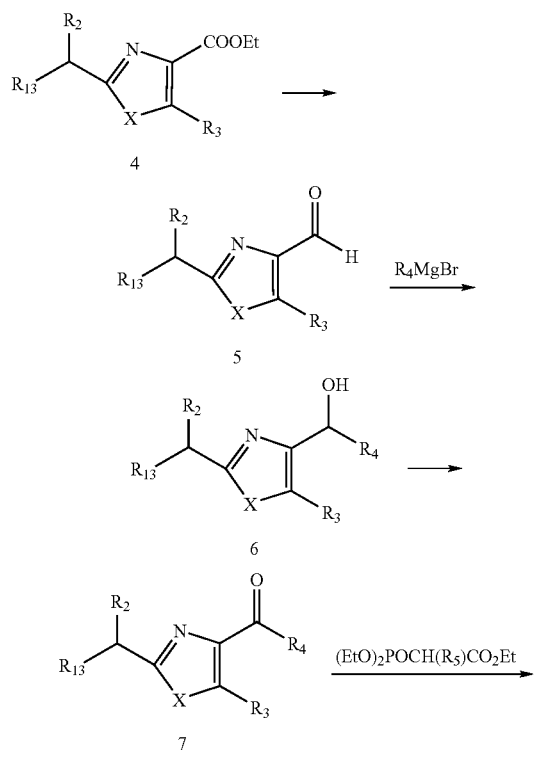

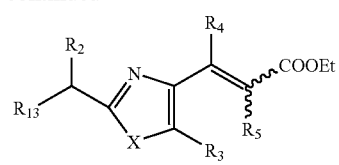

Step 3: as illustrated in the following reaction scheme, the α,β-unsaturated ethyl carboxylate compound 8 was reduced by lithium aluminium hydride at a temperature in the range of 0° C. to room temperature using tetrahydrofuran as a solvent to obtain a corresponding alcohol compound, which was then oxidized by IBX at 50° C. using toluene and dimethylsulfoxide as solvents to a corresponding aldehyde compound 9. The α,β-unsaturated aldehyde compound 9 was then reacted with a Grignard reagent under room temperature or heating using tetrahydrofuran as a solvent to afford a corresponding sec-alcohol compound 10. After the sec-alcohol compound 10 was oxidized by IBX at 50° C. using toluene and dimethylsulfoxide as solvents to a corresponding ketone compound 11, the ketone compound 11 was finally reacted with Wittig-Horner reagent at a temperature in the range of 0° C. to room temperature using tetrahydrofuran as a solvent to provide an aromatic cyclic compound 12 in the cis- or trans-configuration which is substituted by conjugated double bonds;

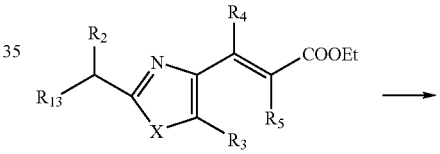

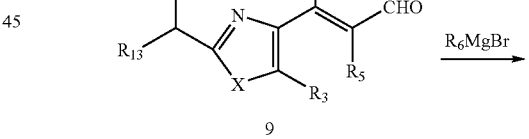

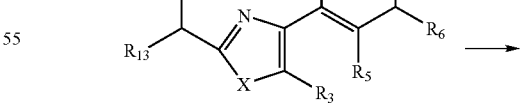

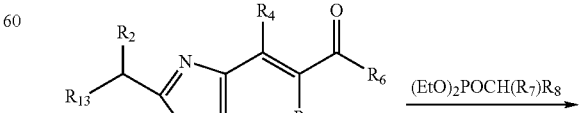

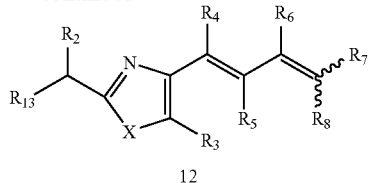

12

Step 4: as illustrated in the following reaction scheme, a compound I was obtained by removing the protecting group for $R_{13}$ of compound 12, followed by coupling with the corresponding $R_9COOH$, $R_9COCl$ or $R_9COCOOH$ using dichloromethane as a solvent, or with $R_9NH_2$ in the presence of carbonyldiimidazole using tetrahydrofuran as a solvent, or with $R_9COC(PPh_3)CN$ under ozonized conditions using dichloromethane as a solvent.

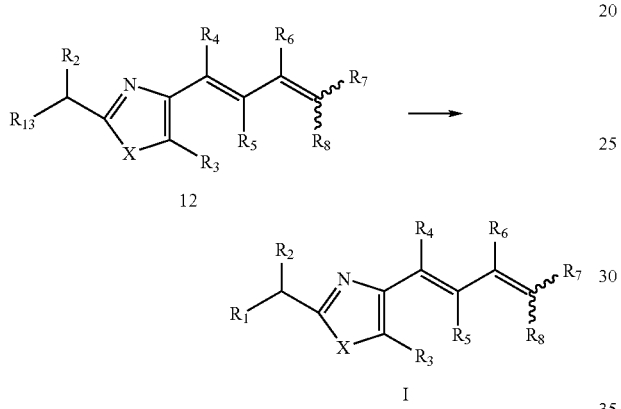

In the above four steps, X, $R_1$, $R_3$-$R_9$ and $R_{13}$ are the same as defined in the compound I; Y and $R_{10}$-$R_{12}$ are the same as defined in the compound II.

$R_{13}$ is preferably NHBoc or OTBS.

The reaction time of the above reactions is dependent on the specific reactants. The reactions are generally tracked with TLC. The post-treatments after reaction typically include vacuum filtration, concentration of reaction liquid to remove solvents, recrystallization, extraction, column chromatographic separation, and the like. The final products were identified by nuclear magnetic resonance (NMR) spectrum.

The novel fused heterocyclic triazole PTP1B inhibitors designed and synthesized in the present invention show effective activity for inhibiting the activity of PTP1B in vitro tests, therefore can be used to prepare medicants for preventing, delaying or treating diseases which are related to the diseases mediated by PTP1B, especially type II diabetes and obesity.

BRIEF DESCRIPTION OF THE DRAWINGS

FIG. 1 shows the effect of WY586s on the phosphorylation level of insulin receptors in CHO/IR cells, that is, the effect of compound WY586s on the phosphorylation of insulin receptors (p-IR) at the four final concentrations of 0.21, 0.43, 0.85, 1.70 μM, respectively, using the solvent DMSO as negative control (represented with 0) and sodium vanadate as a positive compound (represented with V), and IRβ was insulin receptor β-subunit, representing the basal expression level of insulin receptors.

DETAILED DESCRIPTION

Best Mode for Carrying Out the Invention

Hereinafter, the present invention will be described in more detail through the following examples, which are provided to facilitate the understanding of the present invention. However, the present invention is not limited to or by the examples.

In the following preparative examples, NMR spectra were measured on a Varian Mercury-Vx 300M instrument, and standardized with δH/C 7.26/77.23 ppm ($CDCl_3$). The reagents were mainly provided by Shanghai Chemical Co. Ltd., and the products were mainly purified by column chromatography using ZLX-II silica gel (200-300 mesh), which is commercially available from Qingdao Haiyang Chemical Co. Ltd.

Example 1

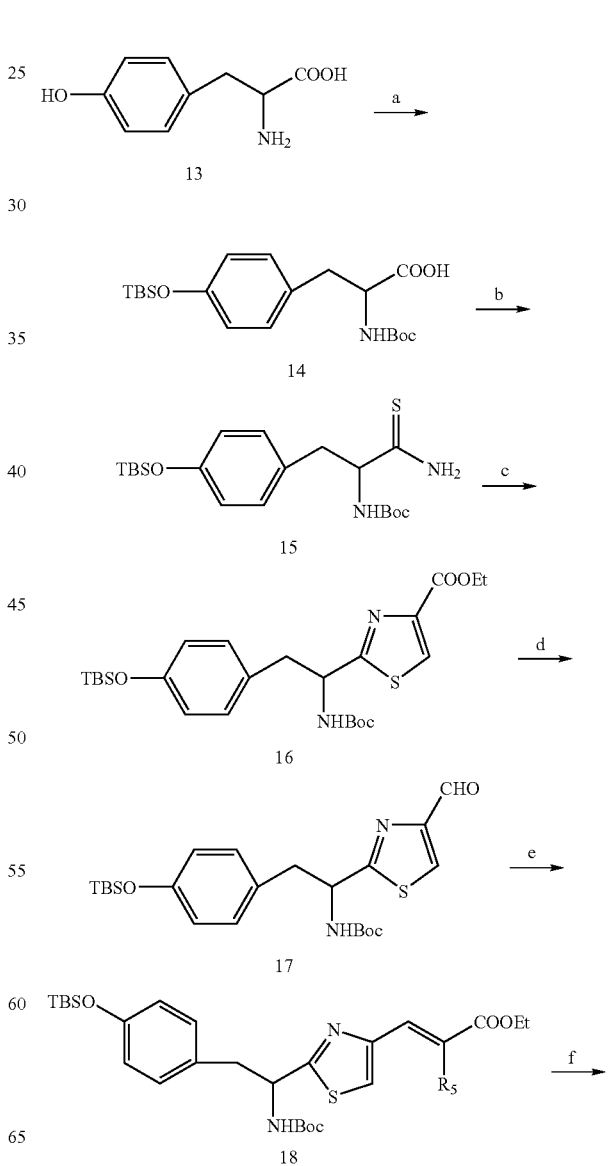

-continued

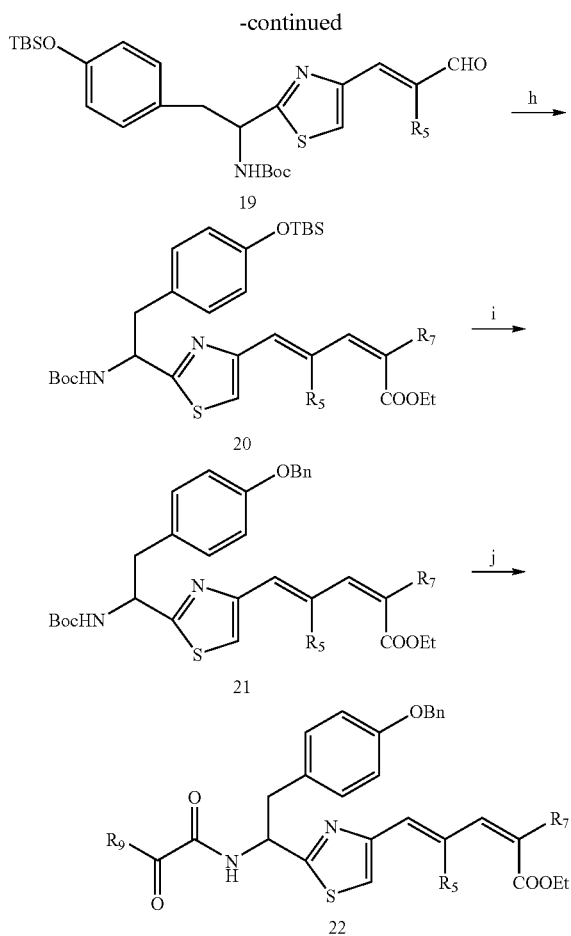

a. i) (Boc)₂O, (Et)₃N; H₂O/dioxane; ii) TBSCl, imidazole, DMF; b. i) NH₃, N-methylmorpholine, ClCOOBu, DME; ii). Lawesson reagent, DME; c. i) ethyl bromopyruvate, KHCO₃; DME; ii) TFAA; d. DIBAL-H; CH₂Cl₂; −78 ; e. (EtO)₂P(O)CH(R₅)COOEt, NaH; THF; f. i) LiAlH₄, THF; ii) DMSO, (COCl)₂, (Et)₃N; CH₂Cl₂; -78 ; h. (CF₃CH₂O)₂P(O)CH(R₇)COOEt, KN(TMS)₂; THF; i. i) TBAF, THF; ii) BnBr, K₂CO₃, DMF; j. i) TFA, CH₂Cl₂; ii) R₉COC(PPh₃)CN, O₃, CH₂Cl₂, Ag₂O.

Step 1:

55 mmol tyrosine was suspended in a mixture of 100 mL H₂O and 100 mL 1,4-dioxane, followed by addition of 110 mmol triethylamine. After the reaction mixture was reacted for 1 h, 83 mmol (Boc)₂O was added, and the reaction was continued for 20 h. The reaction solution was then rotarily evaporated to dryness. The residue was diluted with ice water, and washed with ethyl acetate. The water phase was adjusted to pH 2, and extracted with ethyl acetate. The concentrated product was dissolved in 100 mL DME, and 0.22 mol imidazole was added therein. After stirred for 10 min, 0.1 mol TBSCl was added. The mixture was reacted overnight, and then quenched with ice water, extracted with ethyl ether, and concentrated to obtain compound 14 (yield: 80%).

32 mmol compound 14 was dissolved in 200 mL redistilled DME, followed by addition of 32 mmol N-methylmorpholine and 32 mmol isobutyl chloroformate at −13. After reacted for 1 h at room temperature, the reaction mixture was purged with ammonia for 4 h, and then quenched with ice water, extracted with chloroform. The concentrated product was dissolved in 200 mL redistilled DME, followed by addition of 16 mmol Lawesson reagent. The mixture was reacted for 5 h, and then quenched with ice water, adjusted to pH 8, and extracted with dichloromethane. After ratorily evaporated to dryness, the residue was purified through column chromatography to obtain compound 15 (yield: 80%).

1 mmol compound 15 and 8 mmol potassium bicarbonate were dissolved in 10 mL redistilled DME, and the mixture was reacted for 15 min, followed by addition of 3 mmol a-ethyl bromopyruvate. After the reaction mixture was reacted for 3 h, a solution of trifluoroacetic anhydride (4 mmol) and 2,6-dimethylpyridine (8 mmol) in 5 mL DME was added dropwise at 0□, and the reaction was continued for 5 h. After DME was removed by rotary evaporation, the residue was washed with water, extracted with ethyl acetate. The organic phase was rotarily evaporated to dryness, and the residue was purified through column chromatography to obtain compound 16 (yield: 90%).

Step 2:

The compound 16 (7.5 mmol) was dissolved in 50 mL dichloromethane, followed by dropwise addition of a solution of DIBAL-H (19 mmol) in n-hexane (19 mL) at −78□. After reacted for 10 h, the reaction mixture was quenched with acetone, and then heated to room temperature, followed by addition of 20% sodium potassium tartrate solution. After stirred for 10 h, the reaction mixture was extracted with ethyl acetate. The organic phase was concentrated, and the residue was purified through column chromatography to obtain compound 17 (yield: 70%).

6 mmol phosphonate compound of $(EtO)_2P(O)CH(CH_3)CO_2Et$ was dissolved in 10 mL anhydrous THF, followed by addition of 7 mmol NaH. After the reaction mixture was reacted for 30 min, a solution of 3 mmol compound 17 in THF was added under ice bath, and the reaction was continued for 4 h. The reaction mixture was then quenched with ice water, and extracted with ethyl acetate. The organic phase was concentrated, and the residue was purified through column chromatography to obtain compound 18 (yield: 82%).

Step 3:

0.5 mmol lithium aluminium hydride was dissolved in 20 mL anhydrous THF, followed by addition of a solution of 0.5 mmol compound 18 in THF (10 mL). The reaction mixture was reacted for 1 h, then quenched with ice water, and extracted with ethyl acetate. The concentrated product was used in the next reaction. 1 mmol oxalyl chloride was dissolved in 2 mL dichloromethane. After the solution was cooled to −78□, a solution of dimethyl sulfoxide (2 mmol) in dichloromethane was added, and the reaction mixture was stirred for 30 min. Then a solution of compound 20 (0.5 mmol) in dichloromethane was added dropwise, and the mixture was reacted for 8 h, followed by addition of 3 mmol triethylamine. After the reaction mixture was stirred for 10 h at room temperature, ice water was added. The reaction mixture was extracted with dichloromethane, and the organic phase was concentrated. The residue was purified through column chromatography to obtain compound 19 (yield: 70%).

27 mmol 18-crown-6 and 5.5 mmol phosphonate compound of $(CF_3CH_2O)_2P(O)CH(CH_3)CO_2Et$ were dissolved in 10 mL anhydrous THF, and the solution was cooled to −78□. After addition of 5.5 mmol potassium bis(trimethylsilyl)amide solution, the reaction mixture was reacted for 1 h. Then a solution of compound 19 (1.3 mmol) in THF (5 mL) was added, and the reaction was continued for 2 h. The reaction mixture was quenched with saturated ammonium chloride solution, heated to room temperature, diluted with ice water, and extracted with ethyl acetate. The organic phase was concentrated, and the residue was purified through column chromatography to obtain compound 20 (yield: 90%).

Step 4:

0.05 mmol compound 20 was dissolved in redistilled THF, followed by dropwise addition of 0.075 mmol tetrabutylammonium fluoride. After the reaction mixture was reacted for 2 h, the solvent was removed by rotary evaporation, and 0.5 mmol anhydrous potassium carbonate and 2 mL DMF were added. After dropwise addition of 0.25 mmol benzyl bromide, the reaction mixture was reacted overnight, then quenched with ice water, and extracted with ethyl acetate. The organic phase was concentrated, and the residue was purified through column chromatography to obtain compound 21 (yield: 80%).

0.05 mmol compound 21 was dissolved in 2 mL dichloromethane, followed by dropwise addition of 0.75 mL trifluoroacetic acid. After the mixture was reacted for 2 h, the solvent and trifluoroacetic acid were removed by rotary evaporation, and the obtained intermediate was stored for use. A glide of $CH_3(CH_2)_3COC(PPh_3)CN$ (0.1 mmol) was dissolved in 10 mL anhydrous dichloromethane, and the solution was cooled to −78□, and then purged with ozone until the system became blue. A solution of the intermediate obtained before from compound 21 in dichloromethane (2 mL) was added, and the reaction mixture was reacted for 1 h. After the solvent was removed by rotary evaporation, a solution of silver oxide (0.5 mmol) in $THF/H_2O$ (0.4 mL/0.1 mL) was added. The reaction mixture was reacted overnight, then quenched with ice water, and extracted with dichloromethane. The organic phase was concentrated, and the residue was purified through column chromatography (petroleum ether:ethyl acetate=4:1) to obtain compound 22 (yield: 20-50%).

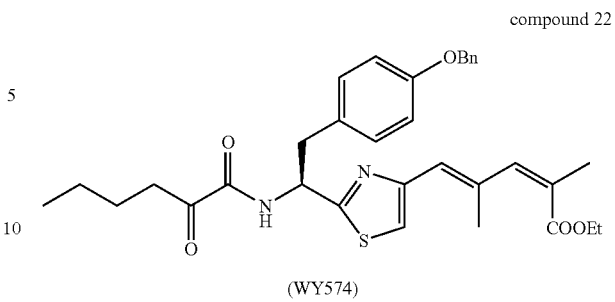

compound 22

(WY574)

$^1$H NMR (CDCl$_3$, 300 MHz): δ 0.91 (t, 3H), 1.27 (t, 3H), 1.32 (m, 2H), 1.57 (m, 2H), 2.03 (s, 3H), 2.15 (s, 3H), 2.88 (t, 2H), 3.25 (d, 2H), 4.21 (q, 2H), 5.21 (s, 2H), 5.42 (q, 1H), 6.27 (s, 1H), 6.47 (s, 1H), 6.84 (d, 2H), 6.99 (s, 1H), 7.01 (d, 2H), 7.33-7.42 (5H), 7.65 (d, 1H).

Example 2-13

The final products of Example 2-13 listed in Table 1-1 were prepared in a process similar to that described in Example 1.

TABLE 1-1

Final products ($R_5 = R_7$ = Me)

| Example | Compound | $R_9$ | Formula | $^1$H NMR (CDCl$_3$, 300 MHz) |
|---|---|---|---|---|
| 2 | WY594 | phenyl | | δ1.27 (t, 3H), 2.03 (s, 3H), 2.17 (s, 3H), 3.32 (d, 2H), 4.21 (q, 2H), 5.01 (s, 2H), 5.58 (q, 1H), 6.28 (s, 1H), 6.49 (s, 1H), 7.00 (d, 2H), 7.03 (s, 1H), 7.06 (d, 2H), 7.30-7.49 (8H), 7.61 (d, 1H), 7.76 (d, 1H), 8.26 (d, 1H). |
| 3 | WY558 | cyclopropyl | | δ 1.16 (dd, 4H), 1.25 (t, 3H), 2.03 (s, 3H), 2.16 (s, 3H), 3.04 (m, 1H), 3.27 (dd, 2H), 4.22 (q, 2H), 5.01 (s, 2H), 5.47 (q, 1H), 6.27 (s, 1H), 6.47 (s, 1H), 6.85 (d, 2H), 6.87 (s, 1H), 6.88 (d, 2H), 7.31-7.43 (5H), 7.69 (d, 1H). |
| 4 | WY612 | 4-fluorophenyl | | δ1.27 (t, 3H), 2.03 (s, 3H), 2.17 (s, 3H), 3.31 (d, 2H), 4.21 (q, 2H), 5.02 (s, 2H), 5.58 (q, 1H), 6.28 (s, 1H), 6.49 (s, 1H), 6.87 (d, 2H), 7.02 (s, 1H), 7.05 (d, 2H), 7.13 (t, 2H), 7.30-7.49 (5H), 7.82 (d, 1H), 8.37 (dd, 1H). |

TABLE 1-1-continued

Final products ($R_5 = R_7 = Me$)

| Example | Compound | $R_9$ | Formula | $^1$H NMR (CDCl$_3$, 300 MHz) |
|---|---|---|---|---|
| 5 | WY600 | cyclohexyl | | δ 1.25 (t, 3H), 1.40-1.50 (4H), 1.65-1.75 (6H), 2.03 (s, 3H), 2.16 (s, 3H), 3.25 (d, 2H), 3.27 (m, 1H), 4.22 (q, 2H), 5.01 (s, 2H), 5.45 (q, 1H), 6.27 (s, 1H), 6.48 (s, 1H), 6.84 (d, 2H), 6.96 (s, 1H), 7.04 (d, 2H), 7.30-7.43 (5H), 7.63 (d, 1H). |
| 6 | WY586 | cyclopentyl | | δ 1.26 (t, 3H), 1.58-1.78 (4H), 1.80-1.96 (4H), 1.98 (s, 3H), 2.11 (s, 3H), 3.26 (d, 2H), 3.72 (m, 1H), 4.21 (q, 2H), 5.01 (s, 2H), 5.45 (q, 1H), 6.27 (s, 1H), 6.47 (s, 1H), 6.84 (d, 2H), 6.99 (s, 1H), 7.00 (d, 2H), 7.31-7.39 (5H), 7.79 (d, 1H). |
| 7 | WY562 | methoxymethyl | | δ 1.25 (t, 3H), 2.03 (s, 3H), 2.16 (s, 3H), 3.25 (d, 2H), 3.36 (s, 3H), 3.88 (d, 2H), 4.21 (q, 2H), 5.02 (s, 2H), 5.54 (q, 1H), 6.28 (s, 1H), 6.48 (s, 1H), 6.87 (d, 2H), 6.99 (s, 1H), 7.02 (d, 2H), 7.31-7.42 (6H). |
| 8 | WY638 | benzyloxymethyl | | δ 1.28 (t, 3H), 2.03 (s, 3H), 2.14 (s, 3H), 3.26 (d, 2H), 3.99 (s, 2H), 4.19 (q, 2H), 4.51 (s, 2H), 5.01 (s, 2H), 5.57 (q, 1H), 6.27 (s, 1H), 6.48 (s, 1H), 6.84 (d, 2H), 6.98 (d, 2H), 6.99 (s, 1H), 7.26 (d, 1H), 7.27-7.42 (9H). |
| 9 | WY572 | cyclobutyl | | δ 1.27 (t, 3H), 2.03 (s, 3H), 2.16 (s, 3H), 2.18-2.27 (m, 6H), 4.21 (q, 2H), 4.02 (m, 1H), 5.01 (s, 2H), 5.43 (q, 1H), 6.28 (s, 1H), 6.48 (s, 1H), 6.85 (d, 2H), 6.99 (s, 1H), 7.01 (d, 2H), 7.33-7.42 (5H), 7.72 (d, 1H). |
| 10 | WY588 | 2-tetrahydrofuryl | | δ 1.27 (t, 3H), 1.54-1.87 (4H), 2.03 (s, 3H), 2.11 (d, 3H), 3.24 (dt, 2H), 3.81 (dq, 2H), 4.21 (q, 2H), 4.34 (m, 1H), 5.02 (d, 2H), 5.53 (q, 1H), 6.27 (s, 1H), 6.47 (d, 1H), 6.94 (d, 2H), 7.00-7.09 (3H), 7.26-7.40 (6H). |

TABLE 1-1-continued

Final products ($R_5 = R_7$ = Me)

| Example | Compound | $R_9$ | Formula | $^1$H NMR (CDCl$_3$, 300 MHz) |
|---|---|---|---|---|
| 11 | WY583 | 2-pyrrolyl | | δ1.26 (t, 3H), 2.04 (s, 3H), 2.18 (s, 3H), 3.32 (d, 2H), 4.22 (q, 2H), 5.00 (s, 2H), 5.52 (q, 1H), 6.35 (s, 1H), 6.36 (d, 1H), 6.50 (s, 1H), 6.85 (d, 2H), 7.01 (s, 1H), 7.05 (d, 2H), 7.10 (br, 1H), 7.31-7.42 (5H), 8.23 (br, 1H) |
| 12 | WY548 | methylol | | δ 1.27 (t, 3H), 2.03 (s, 3H), 2.12 (s, 3H), 3.23 (dd, 2H), 4.10 (d, 2H), 4.20 (q, 2H), 5.01 (s, 2H), 5.55 (q, 1H), 6.27 (s, 1H), 6.47 (s, 1H), 6.84 (d, 2H), 6.83 (s, 1H), 7.00 (d, 2H), 7.32-7.42 (6H). |
| 13 | WY600t | 2-thienyl | | δ1.25 (t, 3H), 2.04 (s, 3H), 2.18 (s, 3H), 3.32 (d, 2H), 4.22 (q, 2H), 5.00 (s, 2H), 5.53 (q, 1H), 6.28 (s, 1H), 6.49 (d, 1H), 6.87 (d, 2H), 7.01 (s, 1H), 7.04 (d, 2H), 7.16 (t, 1H), 7.31-7.42 (5H), 7.82 (dd, 2H), 8.04 (d, 2H), 8.39 (dd, 2H). |

Example 14

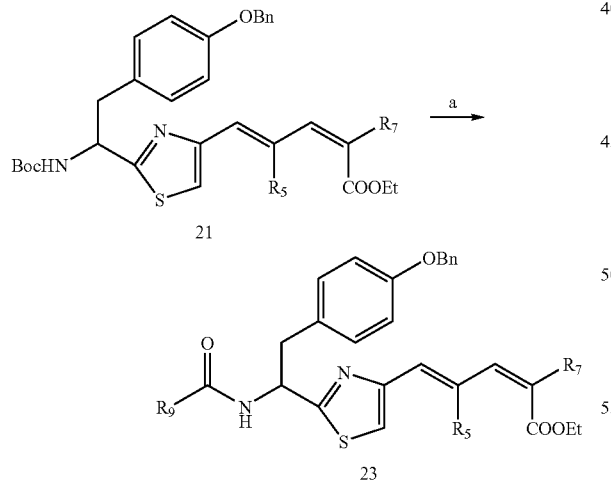

a. i) TFA, CH$_2$Cl$_2$; ii) R$_9$COOH, EDCI, DMAP.

The preparation of compound 21 was the same as described in Example 1.

0.05 mmol compound 21 was dissolved in 1 mL dichloromethane, followed by dropwise addition of 0.3 mL trifluoroacetic acid. After the mixture was reacted for 2 h, the solvent and trifluoroacetic acid were removed by rotary evaporation. 0.06 mmol F$_3$CCOOH, 0.12 mmol EDCI, 0.01 mmol DMAP and 2 mL DMF were added, and the reaction mixture was reacted overnight, and then quenched with ice water, and extracted with ethyl acetate. The organic phase was concentrated, and the residue was purified through column chromatography (petroleum ether:ethyl acetate=4:1) to obtain compound 23 (yield: 50-90%).

compound 23 (WY558f)

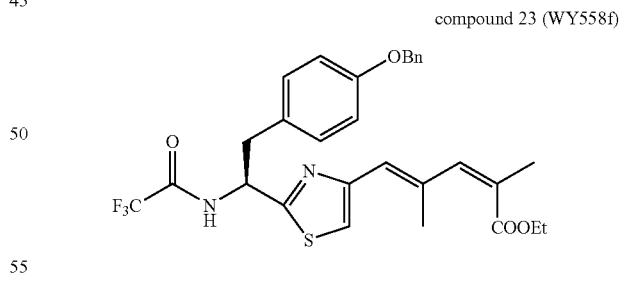

$^1$H NMR (CDCl$_3$, 300 MHz): δ 1.26 (t, 3H), 2.04 (s, 3H), 2.17 (s, 3H), 3.26 (dq, 2H), 4.21 (q, 2H), 5.02 (s, 2H), 5.47 (q, 1H), 6.27 (s, 1H), 6.48 (s, 1H), 6.88 (d, 2H), 6.98 (d, 2H), 7.04 (s, 1H), 7.32-7.44 (5H), 7.48 (d, 1H).

Example 15-35

The final products of Example 15-34 listed in Table 1-2 were prepared in a process similar to that described in Example 14.

TABLE 1-2

| Example | Compound | R$_9$ | Formula | $^1$H NMR (CDCl$_3$, 300 MHz) |
|---|---|---|---|---|
| 15 | WY584s | 4-fluoro-phenyl | | δ1.24 (t, 3H), 1.99 (s, 3H), 2.14 (s, 3H), 3.34 (dq, 2H), 4.17 (q, 2H), 5.01 (s, 2H), 5.69 (q, 1H), 6.27 (s, 1H), 6.49 (s, 1H), 6.84 (d, 2H), 7.00 (s, 1H), 7.02 (d, 2H), 7.09 (m, 2H), 7.31-7.42 (5H), 7.76 (m, 2H). |
| 16 | WY566s | phenyl | | δ1.26 (t, 3H), 2.03 (s, 3H), 2.16 (s, 3H), 3.34 (dq, 2H), 4.21 (q, 2H), 5.01 (s, 2H), 5.72 (q, 1H), 6.28 (s, 1H), 6.50 (s, 1H), 6.85 (d, 2H), 7.05 (s, 1H), 7.08 (d, 2H), 7.12 (d, 1H), 7.31-7.74 (8H), 7.75 (d, 2H). |
| 17 | WY558s | cyclo-pentyl | | δ 1.25 (t, 3H), 1.50-1.90 (8H), 2.03 (s, 3H), 2.03 (m, 1H), 2.14 (s, 3H), 3.23 (d, 2H), 4.21 (q, 2H), 5.01 (s, 2H), 5.53 (q, 1H), 6.27 (br, 2H), 6.48 (s, 1H), 6.84 (d, 2H), 6.97 (d, 2H), 6.99 (s, 1H), 7.31-7.43 (5H). |
| 18 | WY544s | cyclo-butyl | | δ 1.24 (t, 3H), 1.87 (m, 2H), 1.98 (s, 3H), 2.18 (s, 3H), 2.21 (m, 4H), 3.00 (m, 1H), 3.22 (d, 2H), 4.20 (q, 2H), 5.01 (s, 2H), 5.52 (q, 1H), 6.17 (d, 1H), 6.27 (s, 1H), 6.48 (s, 1H), 6.84 (d, 2H), 6.98 (d, 2H), 6.99 (s, 1H), 7.28-7.42 (5H). |
| 19 | WY610s | ben-zyloxy-methyl | | δ 1.26 (t, 3H), 2.04 (s, 3H), 2.15 (s, 3H), 3.26 (d, 2H), 4.00 (s, 2H), 4.19 (q, 2H), 4.52 (s, 2H), 5.00 (s, 2H), 5.58 (q, 1H), 6.28 (s, 1H), 6.50 (s, 1H), 6.83 (d, 2H), 6.99 (d, 2H), 7.01 (s, 1H), 7.27 (d, 2H), 7.28-7.43 (8H). |
| 20 | WY562s | acetyl-oxy-methyl | | δ 1.26 (t, 3H), 2.03 (s, 3H), 2.11 (s, 3H), 2.15 (s, 3H), 3.24 (dq, 2H), 4.20 (q, 2H), 4.57 (s, 2H), 5.01 (s, 2H), 5.54 (q, 1H), 6.27 (s, 1H), 6.46 (s, 1H), 6.90 (d, 2H), 7.01 (d, 2H), 7.04 (s, 1H), 7.31-7.43 (5H). |

TABLE 1-2-continued

Final products ($R_5 = R_7 = $ Me)

| Example | Compound | $R_9$ | Formula | $^1$H NMR (CDCl$_3$, 300 MHz) |
|---|---|---|---|---|
| 21 | WY530s | cyclopropyl | 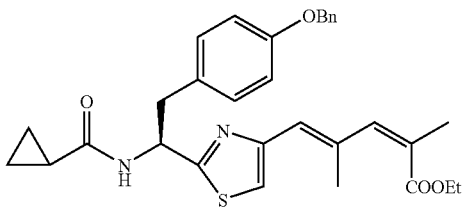 | δ 0.74 (m, 2H), 0.90 (m, 2H), 1.24 (t, 3H), 1.38 (m, 1H), 2.03 (s, 3H), 2.14 (s, 3H), 3.24 (dq, 2H), 4.21 (q, 2H), 5.01 (s, 2H), 5.53 (q, 1H), 6.27 (d, 1H), 6.50 (br, 2H), 6.86 (d, 2H), 6.98 (d, 2H), 7.00 (s, 1H), 7.30-7.43 (5H). |
| 22 | WY622s | 2-benzothienyl | 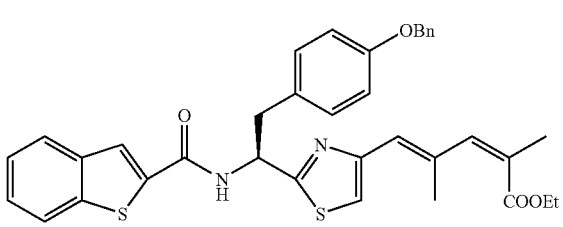 | δ 1.27 (t, 3H), 2.04 (s, 3H), 2.17 (s, 3H), 3.37 (dq, 2H), 4.21 (q, 2H), 5.00 (s, 2H), 5.72 (q, 1H), 6.29 (s, 1H), 6.51 (s, 1H), 6.86 (d, 2H), 7.02 (s, 1H), 7.04 (d, 2H), 7.24 (d, 2H), 7.28-7.45 (8H), 7.78 (s, 1H), 7.82 (t, 2H). |
| 23 | WY596s | 4-methoxyphenyl | 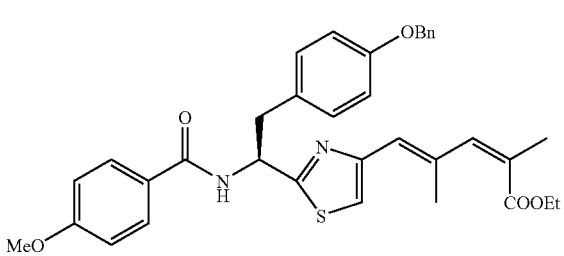 | δ 1.26 (t, 3H), 2.04 (s, 3H), 2.15 (s, 3H), 3.34 (dq, 2H), 3.83 (s, 3H), 4.21 (q, 2H), 5.01 (s, 2H), 5.71 (q, 1H), 6.28 (s, 1H), 6.50 (s, 1H), 6.85 (d, 2H), 6.90 (d, 2H), 7.02 (d, 2H), 7.09 (m, 2H), 7.29-7.40 (5H), 7.73 (d, 2H). |
| 24 | WY560s | 2-tetrahydrofuryl | 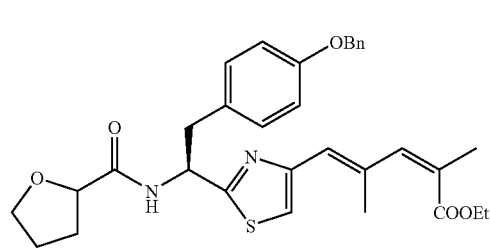 | δ 1.27 (t, 3H), 1.85 (m 4H), 2.05 (s, 3H), 2.25 (d, 3H), 3.22 (dq, 2H), 3.75 (m, 2H), 4.18 (q, 2H), 4.34 (q, 1H), 5.01 (d, 2H), 5.48 (q, 1H), 6.27 (s, 1H), 6.47 (d, 1H), 6.85 (d, 2H), 6.98 (m, 3H), 7.29-7.43 (5H). |
| 25 | WY560t | 2,2-dimethylpropyl | 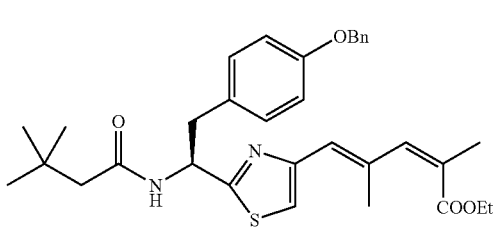 | δ 1.03 (s, 9H), 1.26 (t, 3H), 2.03 (s, 3H), 2.05 (s, 2H), 2.14 (s, 3H), 3.22 (d, 2H), 4.20 (q, 2H), 5.01 (s, 2H), 5.54 (q, 1H), 6.26 (br, 2H), 6.48 (s, 1H), 6.84 (d, 2H), 6.99 (s, 1H), 7.01 (d, 2H), 7.28-7.39 (5H). |
| 26 | WY580s | benzyl | 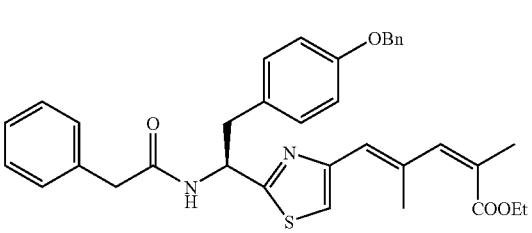 | δ 1.26 (t, 3H), 2.04 (s, 3H), 2.09 (s, 3H), 3.13 (d, 2H), 3.57 (s, 2H), 4.21 (q, 2H), 5.02 (s, 2H), 5.52 (q, 1H), 6.15 (d, 2H), 6.26 (s, 1H), 6.43 (s, 1H), 6.78 (br, 4H), 6.97 (br, 1H), 7.17 (m, 2H), 7.29-7.44 (8H). |

TABLE 1-2-continued

Final products ($R_5 = R_7 = Me$)

| Example | Compound | $R_9$ | Formula | $^1$H NMR (CDCl$_3$, 300 MHz) |
|---|---|---|---|---|
| 27 | WY556s | 2-furyl | | δ 1.26 (t, 3H), 2.03 (s, 3H), 2.17 (s, 3H), 3.33 (dq, 2H), 4.21 (q, 2H), 5.01 (s, 2H), 5.68 (q, 1H), 6.28 (s, 1H), 6.49 (br, 2H), 6.85 (d, 2H), 7.00 (s, 1H), 7.04 (d, 2H), 7.09 (d, 1H), 7.15 (d, 1H), 7.31-7.43 (5H). |
| 28 | WY532s | iso-propyl | | δ 1.11 (dd, 6H), 1.26 (t, 3H), 2.03 (s, 3H), 2.14 (s, 3H), 2.38 (m, 1H), 3.22 (dd, 2H), 4.21 (q, 2H), 5.02 (s, 2H), 5.53 (q, 1H), 6.27 (s, 1H), 6.37 (d, 1H), 6.48 (s, 1H), 6.84 (d, 2H), 6.98 (d, 2H), 7.00 (s, 1H), 7.28-7.42 (5H). |
| 29 | WY652s | 1-benzyloxy-2-methyl-propyl | | δ 0.94 (dd, 6H), 1.26 (t, 3H), 2.04 (s, 3H), 2.15 (s, 3H), 3.34 (dq, 2H), 3.63 (d, 1H), 4.21 (q, 2H), 4.37 (s, 2H), 4.97 (s, 2H), 5.63 (q, 1H), 6.28 (s, 1H), 6.48 (br, 2H), 6.80 (d, 2H), 7.01 (s, 1H), 7.03 (d, 2H), 7.29-7.42 (10H). |
| 30 | WY584 | phenyl-methylol | | δ 2.03 (s, 3H), 2.09 (d, 3H), 3.20 (m, 2H), 3.75 (s, 3H), 5.01 (d, 2H), 5.04 (br, 1H), 5.52 (q, 1H), 6.26 (s, 1H), 6.42 (s, 1H), 6.74-6.99 (6H), 7.24-7.44 (8H). |
| 31 | WY602-2 | cyclo-hexyl-methylol | | δ 1.26 (t, 3H), 1.30-1.44 (4H), 1.66-1.80 (6H), 2.03 (s, 3H), 2.07 (m, 1H), 2.14 (s, 3H), 3.27 (d, 2H) 4.21 (q, 2H), 5.01 (s, 2H), 5.55 (q, 1H), 6.14 (d, 1H), 6.27 (s, 1H), 6.48 (s, 1H), 6.85 (d, 2H), 6.99 (d, 2H), 7.01 (s, 1H), 7.32-7.42 (5H). |
| 32 | WY586s | cyclo-hexyl-methyl | | δ 0.85 (m, 2H), 1.16 (m, 3H), 1.28 (t, 3H), 1.62-1.72 (6H), 2.03 (s, 3H), 2.07 (m, 2H), 2.14 (s, 3H), 3.22 (d, 2H), 4.21 (q, 2H), 5.01 (s, 2H), 5.56 (q, 1H), 6.21 (d, 1H), 6.27 (s, 1H), 6.48 (s, 1H), 6.86 (d, 2H), 6.99 (s, 2H), 7.01 (d, 2H), 7.31-7.43 (5H). |

TABLE 1-2-continued

Final products ($R_5 = R_7$ = Me)

| Example | Compound | $R_9$ | Formula | $^1$H NMR (CDCl$_3$, 300 MHz) |
|---|---|---|---|---|
| 33 | WY586d | 2-cyclohexanoyl | | δ 1.28 (t, 3H), 1.68 (br, 4H), 1.93 (m, 1H), 2.03 (s, 3H), 2.11 (m, 2H), 2.17 (s, 3H), 2.30 (br, 1H), 3.15-3.22 (3H), 4.21 (q, 2H), 5.02 (s, 2H), 5.56 (q, 1H), 6.25 (d, 1H), 6.27 (s, 1H), 6.47 (s, 1H), 6.85 (d, 2H), 7.00 (d, 2H), 7.03 (d, 2H), 7.06 (t, 1H), 7.31-7.42 (4H). |
| 34 | WY587s | 4-N-methyl-piperidyl | | δ 1.26 (t, 3H), 1.70-1.82 (2H), 1.96-2.02 (2H), 2.03 (s, 3H), 2.07 (m, 1H), 2.13 (s, 3H), 2.28 (s, 3H), 2.86 (m, 2H), 3.22 (dd, 2H), 4.20 (q, 2H), 5.01 (s, 2H), 5.53 (q, 1H), 6.27 (s, 1H), 6.31 (d, 1H), 6.47 (s, 1H), 6.84 (d, 2H), 6.96 (d, 2H), 6.99 (s, 1H), 7.31-7.42 (5H). |
| 35 | WY572s | cyclohexyl | | δ 1.26 (t, 3H), 1.30-1.44 (4H), 1.66-1.80 (6H), 2.03 (s, 3H), 2.07 (m, 1H), 2.14 (s, 3H), 3.22 (dd, 2H), 4.20 (q, 2H), 5.02 (s, 2H), 5.53 (q, 1H), 6.27 (s, 1H), 6.32 (d, 1H), 6.48 (s, 1H), 6.84 (d, 2H), 6.98 (d, 2H), 6.99 (s, 1H), 7.30-7.43 (5H). |

Example 36

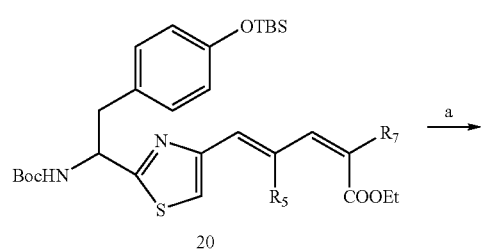

20

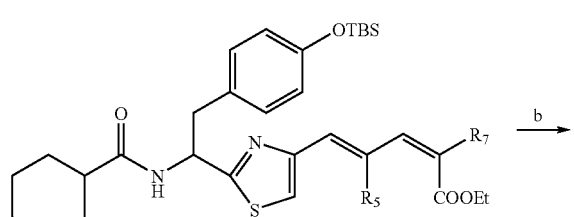

24

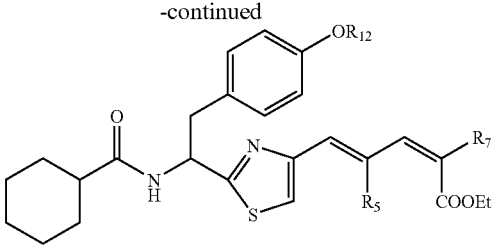

25 a. i) TFA, CH$_2$Cl$_2$; ii) cyclohexane carboxylic acid, EDCI, DMAP, DMF; b. i) TBAF, THF; ii) R$_{12}$X (X = Cl, Br, I), K$_2$CO$_3$, DMF.

The preparation of compound 20 was the same as described in Example 1.

0.05 mmol compound 20 was dissolved in 1 mL dichloromethane, followed by dropwise addition of 0.3 mL trifluoroacetic acid. After the reaction mixture was reacted for 2 h, the solvent and trifluoroacetic acid were removed by rotary evaporation. 0.056 mmol cyclohexanecarboxylic acid, 0.12 mmol EDCI, 0.01 mmol DMAP and 2 mL DMF were added, and the reaction mixture was reacted overnight, and then quenched with ice water, and extracted with ethyl acetate. The organic phase was concentrated, and the residue was purified through column chromatography to obtain compound 24 (yield: 80%).

0.04 mmol compound 24 was dissolved in 1 mL THF, followed by dropwise addition of 0.06 mmol tetrabutylammonium fluoride. After the reaction mixture was reacted for 2 h, the solvent was removed by rotary evaporation. 0.5 mmol anhydrous potassium carbonate and 2 mL DMF were added, followed by dropwise addition of CH$_3$I. The reaction mixture was reacted overnight, and then quenched with ice water, and extracted with ethyl acetate. The organic phase was concentrated, and the residue was purified through column chromatography (petroleum ether:ethyl acetate=4:1) to obtain compound 25 (yield: 60-95%).

$^1$H NMR (CDCl$_3$, 300 MHz): δ 1.27 (t, 3H), 1.30-1.44 (4H), 1.66-1.81 (6H), 2.02 (s, 3H), 2.07 (m, 1H), 2.14 (s, 3H), 3.22 (m, 2H), 3.76 (s, 3H), 4.21 (q, 2H), 5.52 (q, 1H), 6.23 (d, 1H), 6.27 (s, 1H), 6.47 (s, 1H), 6.76 (d, 2H), 6.96 (d, 2H), 6.98 (s, 1H).

compound 25 (WY496h)

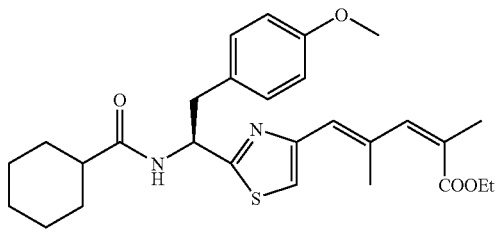

Example 37-55

The final products of Example 36-54 listed in Table 1-3 were prepared in a process similar to that described in Example 35.

TABLE 1-3

| | | | Final products (R$_5$ = R$_7$ = Me) | |
|---|---|---|---|---|
| Example | Compound | R$_{12}$ | Formula | $^1$H NMR (CDCl$_3$, 300 MHz) |
| 37 | WY482h | H | (structure with OH) | δ 1.27 (t, 3H), 1.30-1.44 (4H), 1.66-1.81 (6H), 2.02 (s, 3H), 2.07 (m, 1H), 2.13 (s, 3H), 3.17 (d, 2H), 4.21 (q, 2H), 5.53 (q, 1H), 6.27 (s, 1H), 6.39 (d, 1H), 6.48 (s, 1H), 6.70 (d, 2H), 6.90 (d, 2H), 6.99 (s, 1H). |
| 38 | WY568h | ethyl acetate group | (structure with O-CH$_2$-COOEt) | δ 1.27 (m, 6H), 1.30-1.44 (4H), 1.66-1.81 (6H), 2.02 (s, 3H), 2.07 (m, 1H), 2.13 (s, 3H), 3.22 (m, 2H), 4.22 (m, 4H), 4.56 (s, 2H), 5.51 (q, 1H), 6.24 (d, 1H), 6.26 (s, 1H), 6.46 (s, 1H), 6.77 (d, 2H), 6.97 (d, 2H), 6.98 (s, 1H). |
| 39 | WY540a | carboxymethyl | (structure with O-CH$_2$-COOH) | δ 1.27 (m, 3H), 1.30-1.44 (4H), 1.66-1.81 (6H), 2.02 (s, 3H), 2.06 (m, 1H), 2.13 (s, 3H), 3.16 (m, 2H), 4.22 (q, 2H), 4.61 (s, 2H), 5.51 (q, 1H), 6.26 (s, 1H), 6.47 (s, 1H), 6.67 (d, 1H), 6.78 (d, 2H), 6.95 (d, 2H), 7.00 (s, 1H). |

TABLE 1-3-continued

Final products ($R_5 = R_7$ = Me)

| Example | Compound | $R_{12}$ | Formula | $^1$H NMR (CDCl$_3$, 300 MHz) |
|---|---|---|---|---|
| 40 | WY582h | (1-carbonyl-ethoxy)-ethyl | 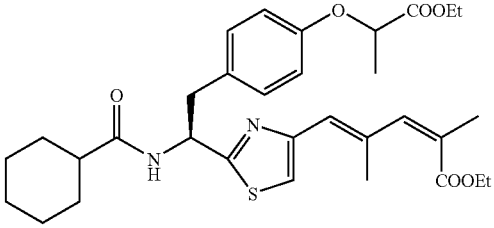 | δ 1.27 (m, 9H), 1.30-1.44 (4H), 1.66-1.81 (6H), 1.57 (d, 2H), 2.02 (s, 3H), 2.07 (m, 1H), 3.19 (m, 2H), 4.22 (m, 4H), 4.67 (q, 1H), 5.50 (q, 1H), 6.23 (dd, 1H), 6.26 (s, 1H), 6.46 (s, 1H), 6.72 (d, 2H), 6.93 (d, 2H), 6.97 (s, 1H). |
| 41 | WY526h | 2-hydroxy-ethyl | 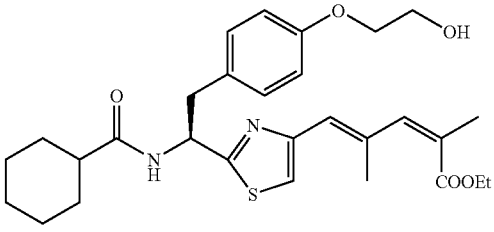 | δ 1.27 (t, 3H), 1.30-1.44 (4H), 1.66-1.81 (6H), 2.02 (s, 3H), 2.07 (m, 1H), 2.14 (s, 3H), 3.21 (m, 2H), 3.94 (br, 2H), 4.02 (d, 2H), 4.21 (q, 2H), 5.52 (q, 1H), 6.27 (br, 2H), 6.47 (s, 1H), 6.77 (d, 2H), 6.96 (d, 2H), 6.99 (s, 1H). |
| 42 | WY538h | n-butyl | 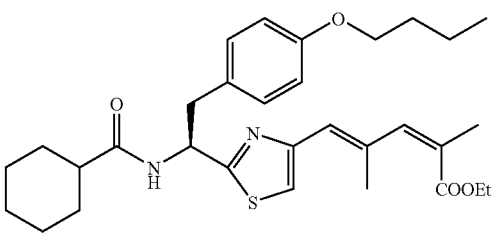 | δ 0.96 (t, 3H), 1.27 (t, 3H), 1.30-1.44 (5H), 1.66-1.81 (9H), 2.02 (s, 3H), 2.07 (m, 1H), 2.14 (s, 3H), 3.22 (m, 2H), 3.90 (t, 2H), 4.21 (q, 2H), 5.52 (q, 1H), 6.23 (d, 1H), 6.57 (s, 1H), 6.47 (s, 1H), 6.76 (d, 2H), 6.95 (d, 2H), 6.99 (s, 1H). |
| 43 | WY597h | 4-cyano-benzyl | 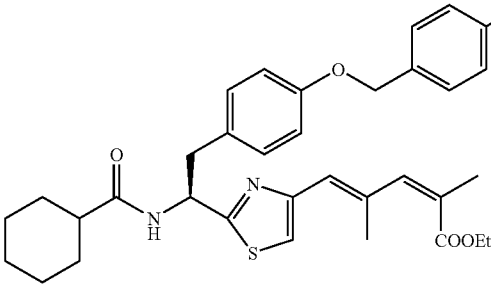 | δ 1.27 (t, 3H), 1.32-1.44 (4H), 1.66-1.80 (6H), 2.02 (s, 3H), 2.07 (m, 1H), 2.13 (s, 3H), 3.22 (d, 2H), 4.20 (q, 2H), 5.07 (s, 2H), 5.50 (q, 1H), 6.26 (s, 1H), 6.28 (d, 1H), 6.47 (s, 1H), 6.80 (d, 2H), 6.90 (d, 2H), 6.99 (s, 1H), 7.52 (d, 2H), 7.66 (d, 2H). |
| 44 | WY590h | 4-fluoro-benzyl | 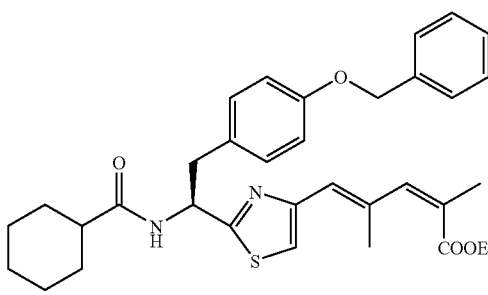 | δ 1.27 (t, 3H), 1.32-1.44 (4H), 1.66-1.80 (6H), 2.03 (s, 3H), 2.07 (m, 1H), 2.14 (s, 3H), 3.21 (d, 2H), 4.21 (q, 2H), 4.97 (s, 2H), 5.52 (q, 1H), 6.25 (d, 1H), 6.27 (s, 1H), 6.48 (s, 1H), 6.82 (d, 2H), 6.85 (d, 2H), 6.86 (s, 1H), 6.99 (dd, 2H), 7.38 (dd, 2H). |

TABLE 1-3-continued

Final products ($R_5 = R_7$ = Me)

| Example | Compound | $R_{12}$ | Formula | $^1$H NMR (CDCl$_3$, 300 MHz) |
|---|---|---|---|---|
| 45 | WY602h | 4-methoxy-benzyl | | δ 1.27 (t, 3H), 1.32-1.44 (4H), 1.66-1.80 (6H), 2.03 (s, 3H), 2.07 (m, 1H), 2.14 (s, 3H), 3.22 (d, 2H), 3.80 (s, 3H), 4.21 (q, 2H), 4.93 (s, 2H), 5.53 (q, 1H), 6.26 (d, 1H), 6.27 (s, 1H), 6.48 (s, 1H), 6.83 (d, 2H), 6.89 (d, 2H), 6.97 (d, 2H), 6.99 (s, 1H), 7.33 (d, 2H). |
| 46 | WY590h3 | 3-fluoro-benzyl | | δ 1.27 (t, 3H), 1.32-1.44 (4H), 1.66-1.80 (6H), 2.03 (s, 3H), 2.07 (m, 1H), 2.14 (s, 3H), 3.22 (d, 2H), 4.21 (q, 2H), 5.01 (s, 2H), 5.52 (q, 1H), 6.26 (d, 1H), 6.27 (s, 1H), 6.48 (s, 1H), 6.82 (d, 2H), 6.98 (d, 2H), 6.99 (s, 1H), 7.11-7.34 (4H). |
| 47 | WY590h2 | 2-fluoro-benzyl | | δ 1.27 (t, 3H), 1.32-1.44 (4H), 1.66-1.80 (6H), 2.03 (s, 3H), 2.07 (m, 1H), 2.14 (s, 3H), 3.22 (d, 2H), 4.21 (q, 2H), 5.08 (s, 2H), 5.52 (q, 1H), 6.25 (d, 1H), 6.27 (s, 1H), 6.48 (s, 1H), 6.84 (d, 2H), 6.98 (d, 2H), 6.99 (s, 1H), 7.07 (t, 1H), 7.15 (t, 1H), 7.29 (t, 1H), 7.48 (t, 1H). |
| 48 | WY622h | 2-naphthyl | | δ 1.25 (t, 3H), 1.32-1.44 (4H), 1.66-1.80 (6H), 2.03 (s, 3H), 2.07 (m, 1H), 2.13 (s, 3H), 3.23 (m, 2H), 4.20 (q, 2H), 5.19 (s, 2H), 5.52 (q, 1H), 6.25 (d, 1H), 6.27 (s, 1H), 6.48 (s, 1H), 6.89 (d, 2H), 6.93-7.03 (4H), 7.47-7.53 (2H), 7.83-7.87 (3H). |
| 49 | WY621h | 4-nitro-2-fluoro-phenyl | | δ 1.27 (t, 3H), 1.32-1.44 (4H), 1.66-1.80 (6H), 2.03 (s, 3H), 2.07 (m, 1H), 2.14 (s, 3H), 3.27 (d, 2H), 4.22 (q, 2H), 5.56 (q, 1H), 6.27 (s, 1H), 6.33 (d, 1H), 6.47 (s, 1H), 6.90 (t, 1H), 6.96 (d, 2H), 7.02 (s, 1H), 7.13 (d, 2H), 7.98 (dd, 1H), 8.07 (dd, 1H). |

TABLE 1-3-continued

Final products ($R_5 = R_7 = Me$)

| Example | Compound | $R_{12}$ | Formula | $^1$H NMR (CDCl$_3$, 300 MHz) |
|---------|----------|----------|---------|-------------------------------|
| 50 | WY586h | phenyl-ethyl | | δ 1.26 (t, 3H), 1.30-1.44 (4H), 1.66-1.80 (6H), 2.03 (s, 3H), 2.07 (m, 1H), 2.14 (s, 3H), 3.07 (t, 2H), 3.24 (m, 2H), 4.12 (t, 2H), 4.24 (q, 2H), 5.53 (q, 1H), 6.22 (d, 1H), 6.27 (s, 1H), 6.48 (s, 1H), 6.75 (d, 2H), 6.94 (d, 2H), 6.98 (s, 1H), 7.30-7.43 (5H). |
| 51 | WY573h | 2-piperidyl | | δ 1.26 (t, 3H), 1.30-1.44 (4H), 1.66-1.80 (6H), 2.03 (s, 3H), 2.07 (m, 1H), 2.14 (s, 3H), 3.22 (m, 2H), 4.22 (q, 2H), 5.16 (s, 2H), 5.53 (q, 1H), 6.22 (d, 1H), 6.27 (s, 1H), 6.47 (s, 1H), 6.83 (d, 2H), 6.97 (d, 2H), 6.99 (s, 1H), 7.22 (t, 1H), 7.49 (d, 1H), 7.70 (t, 1H), 8.59 (d, 1H). |
| 52 | WY573h4 | 4-piperidyl | | δ 1.26 (t, 3H), 1.30-1.44 (4H), 1.66-1.80 (6H), 2.02 (s, 3H), 2.07 (m, 1H), 2.12 (s, 3H), 3.21 (d, 2H), 4.19 (q, 2H), 5.03 (s, 2H), 5.51 (q, 1H), 6.26 (s, 1H), 6.33 (d, 1H), 6.46 (s, 1H), 6.80 (d, 2H), 6.97 (d, 2H), 6.98 (s, 1H), 7.32 (d, 2H), 8.58 (d, 2H). |
| 53 | WY560h | furyl-3-methyl | | δ 1.27 (t, 3H), 1.30-1.44 (4H), 1.66-1.80 (6H), 2.02 (s, 3H), 2.07 (m, 1H), 2.12 (s, 3H), 3.22 (m, 2H), 4.21 (q, 2H), 4.88 (s, 2H), 5.52 (q, 1H), 6.25 (d, 1H), 6.27 (s, 1H), 6.47 (br, 2H), 6.82 (d, 2H), 6.97 (d, 2H), 6.99 (s, 1H), 7.42 (br, 1H), 7.48 (br, 1H). |
| 54 | WY578h | thiophene-3-methyl | | δ 1.27 (t, 3H), 1.30-1.44 (4H), 1.66-1.80 (6H), 2.02 (s, 3H), 2.07 (m, 1H), 2.14 (s, 3H), 3.22 (m, 2H), 4.21 (q, 2H), 5.02 (s, 2H), 5.52 (q, 1H), 6.23 (d, 1H), 6.27 (s, 1H), 6.48 (s, 1H), 6.83 (d, 2H), 6.97 (d, 2H), 6.99 (s, 1H), 7.12 (br, 1H), 7.30 (m, 2H). |

TABLE 1-3-continued

Final products ($R_5 = R_7 = Me$)

| Example | Compound | $R_{12}$ | Formula | $^1$H NMR (CDCl$_3$, 300 MHz) |
|---|---|---|---|---|
| 55 | WY522h | allyl | 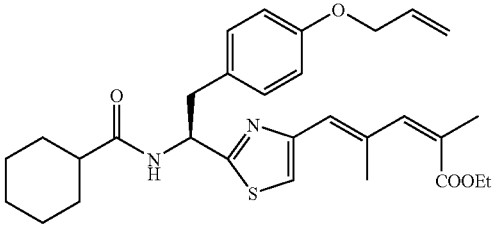 | δ 1.27 (t, 3H), 1.30-1.44 (4H), 1.66-1.81 (6H), 2.02 (s, 3H), 2.07 (m, 1H), 2.14 (s, 3H), 3.22 (br, 2H), 4.21 (q, 2H), 4.48 (d, 2H), 5.26 (d, 1H), 5.38 (d, 1H), 5.52 (q, 1H), 6.02 (m, 1H), 6.24 (d, 1H), 6.27 (s, 1H), 6.47 (s, 1H), 6.77 (d, 2H), 6.96 (d, 2H), 6.99 (s, 1H). |

Example 56

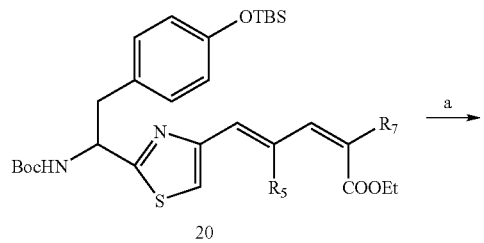
20

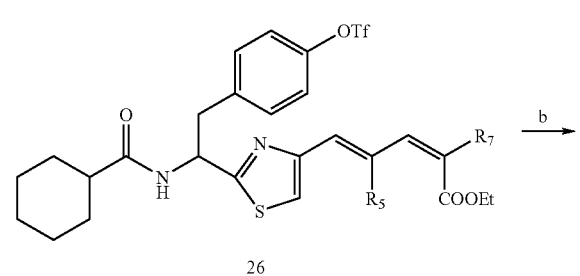
26

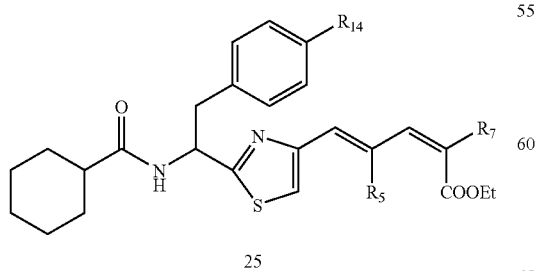
25 a. i) TFA, CH$_2$Cl$_2$; ii) Tf$_2$O, DMAP, CH$_2$Cl$_2$; b. Pd(PPh$_3$)$_4$, K$_2$CO$_3$, R$_{14}$B(OH)$_2$, toluene.

The preparation of the compound 20 was the same as described in Example 1.

0.05 mmol compound 20 was dissolved in 1 mL dichloromethane, followed by dropwise addition of 0.3 mL trifluoroacetic acid. After the reaction mixture was reacted for 2 h, the solvent and trifluoroacetic acid were removed by rotary evaporation. After 0.125 mmol triflic anhydride, 0.15 mmol DMAP and 2 mL CH$_2$Cl$_2$ were added, the reaction mixture was reacted overnight, and then concentrated to obtain compound 26 (yield: 100%).

0.04 mmol compound 26, 0.004 mmol tetrakis(triphenylphosphine)palladium, 0.06 mmol anhydrous potassium carbonate and boric acid were dissolved in 2 mL redistilled toluene. The reaction mixture was reacted overnight at 50□, and then quenched with ice water, and extracted with ethyl acetate. The organic phase was concentrated, and the residue was purified through column chromatography (petroleum ether:ethyl acetate=4:1) to obtain compound 27 (yield: 60-90%).

compound 27 (WY466h)

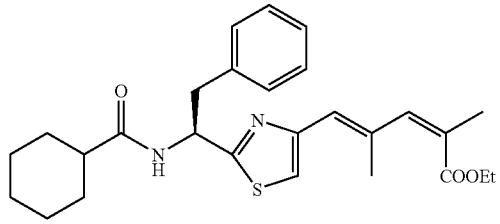

$^1$H NMR (CDCl$_3$, 300 MHz): δ 1.27 (t, 3H), 1.30-1.44 (4H), 1.66-1.80 (6H), 2.03 (s, 3H), 2.07 (m, 1H), 2.13 (s, 3H), 3.20 (dd, 2H), 4.21 (q, 2H), 5.56 (q, 1H), 6.27 (br, 2H), 6.46 (br, 1H), 7.02 (s, 1H), 7.15 (br, 4H).

Example 57

The final product of Example 57 listed in Table 1-4 was prepared in a process similar to that described in Example 56.

TABLE 1-4

| | | | Final product ($R_5 = R_7 = Me$) | |
|---|---|---|---|---|
| Example | Compound | $R_{10}$ | Formula | $^1$H NMR (CDCl$_3$, 300 MHz) |
| 57 | WY542h | phenyl | 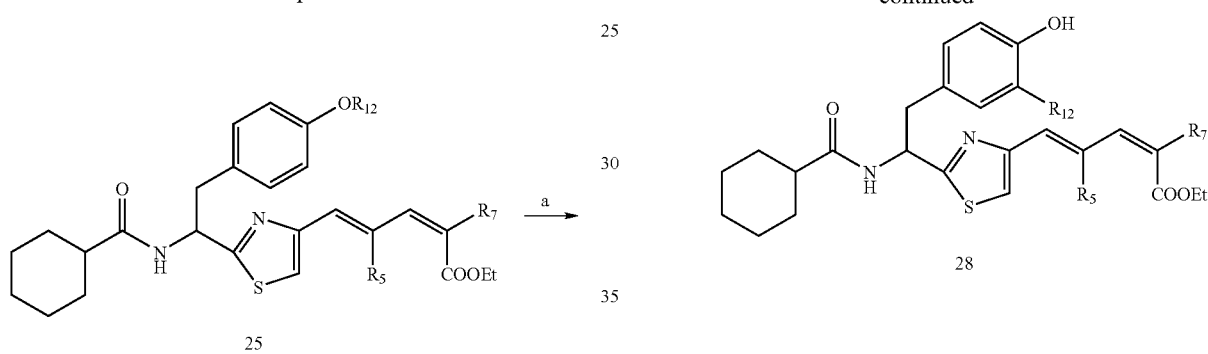 | δ 1.27 (t, 3H), 1.30-1.44 (4H), 1.66-1.80 (6H), 2.03 (s, 3H), 2.07 (m, 1H), 2.15 (s, 3H), 3.23 (dd, 2H), 4.21 (q, 2H), 5.60 (q, 1H), 6.27 (br, 2H), 6.47 (br, 1H), 7.01 (s, 1H), 7.13-7.57 (8H). |

Example 58

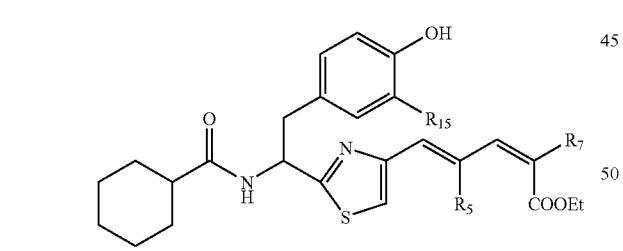

25 a. BCl$_3$, CH$_2$Cl$_2$

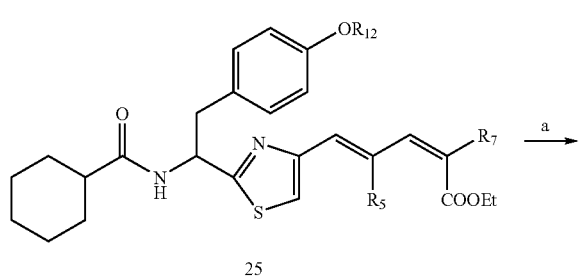

The preparation of the compound 25 was the same as described in Example 36.

0.2 mmol compound 25 was dissolved in 5 mL dichloromethane, followed by dropwise addition of 1.2 mmol boron trichloride-trifluoroacetic acid under ice salt bath. After reacted for 3 h, the reaction mixture was quenched with ice water, and extracted with ethyl acetate. The organic phase was concentrated, and the residue was purified through column chromatography (petroleum ether:ethyl acetate=4:1) to obtain compound 28 (yield: 50-80%).

TABLE 1-5

Final products ($R_5 = R_7 = Me$)

| Compound | $R_{12}$ | Formula | $^1$H NMR (CDCl$_3$, 300 MHz) |
|---|---|---|---|
| WY522b | allyl | | δ 1.27 (t, 3H), 1.30-1.44 (4H), 1.66-1.81 (6H), 2.02 (s, 3H), 2.07 (m, 1H), 2.14 (s, 3H), 3.21 (m, 2H), 4.19 (q, 2H), 4.48 (d, 2H), 5.26 (d, 1H), 5.34 (d, 1H), 5.51 (q, 1H), 6.02 (m, 1H), 6.26 (s, 1H), 6.29 (d, 1H), 6.47 (s, 1H), 6.77 (d, 2H), 6.96 (d, 2H), 6.98 (s, 1H). |
| WY572t | benzyl | | δ 1.27 (t, 3H), 1.30-1.44 (4H), 1.66-1.81 (6H), 2.02 (s, 3H), 2.05 (m, 1H), 2.11 (s, 3H), 3.14 (dd, 2H), 3.89 (s, 2H), 4.20 (q, 2H), 5.49 (q, 1H), 6.26 (s, 1H), 6.32 (d, 1H), 6.47 (s, 1H), 6.64 (d, 2H), 6.74 (s, 1H), 6.79 (d, 2H), 6.95 (s, 1H), 7.12-7.24 (3H). |

Example 59

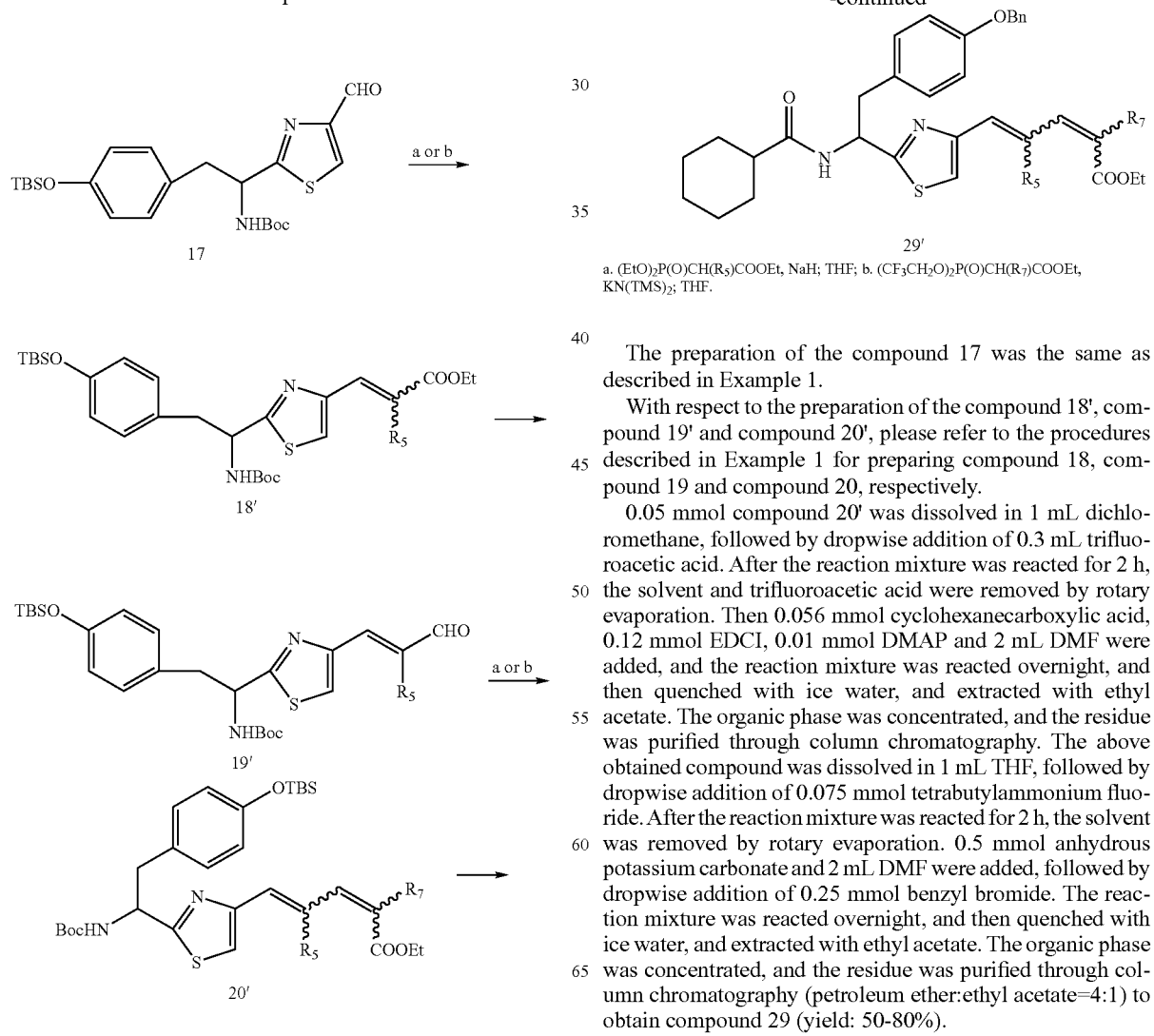

a. (EtO)$_2$P(O)CH(R$_5$)COOEt, NaH; THF; b. (CF$_3$CH$_2$O)$_2$P(O)CH(R$_7$)COOEt, KN(TMS)$_2$; THF.

The preparation of the compound 17 was the same as described in Example 1.

With respect to the preparation of the compound 18', compound 19' and compound 20', please refer to the procedures described in Example 1 for preparing compound 18, compound 19 and compound 20, respectively.

0.05 mmol compound 20' was dissolved in 1 mL dichloromethane, followed by dropwise addition of 0.3 mL trifluoroacetic acid. After the reaction mixture was reacted for 2 h, the solvent and trifluoroacetic acid were removed by rotary evaporation. Then 0.056 mmol cyclohexanecarboxylic acid, 0.12 mmol EDCI, 0.01 mmol DMAP and 2 mL DMF were added, and the reaction mixture was reacted overnight, and then quenched with ice water, and extracted with ethyl acetate. The organic phase was concentrated, and the residue was purified through column chromatography. The above obtained compound was dissolved in 1 mL THF, followed by dropwise addition of 0.075 mmol tetrabutylammonium fluoride. After the reaction mixture was reacted for 2 h, the solvent was removed by rotary evaporation. 0.5 mmol anhydrous potassium carbonate and 2 mL DMF were added, followed by dropwise addition of 0.25 mmol benzyl bromide. The reaction mixture was reacted overnight, and then quenched with ice water, and extracted with ethyl acetate. The organic phase was concentrated, and the residue was purified through column chromatography (petroleum ether:ethyl acetate=4:1) to obtain compound 29 (yield: 50-80%).

TABLE 1-6

| Compound | Formula | $^1$H NMR (CDCl$_3$, 300 MHz) |
|---|---|---|
| WY572-2 | (see structure) | δ 1.26 (t, 3H), 1.30-1.44 (4H), 1.66-1.80 (6H), 2.10 (s, 3H), 2.15 (br, 1H), 2.30 (s, 3H), 3.24 (d, 2H), 4.24 (q, 2H), 5.02 (s, 2H), 5.56 (q, 1H), 6.33 (d, 1H), 6.60 (s, 1H), 6.85 (d, 2H), 7.00 (d, 2H), 7.07 (s, 1H), 7.28 (s, 1H), 7.32-7.42 (5H). |
| WY572-3 | (see structure) | δ 1.30 (t, 3H), 1.32-1.41 (4H), 1.66-1.80 (6H), 1.90 (s, 3H), 2.11 (s, 3H), 2.13 (m, 1H), 3.19 (m, 2H), 4.22 (q, 2H), 5.02 (s, 2H), 5.51 (q, 1H), 6.36 (d, 1H), 6.55 (s, 1H), 6.90 (d, 2H), 6.95 (d, 2H), 6.97 (s, 1H), 7.31-7.43 (5H), 7.79 (s, 1H). |
| WY572-4 | (see structure) | δ 1.26 (t, 3H), 1.32-1.41 (4H), 1.66-1.80 (6H), 2.03 (br, 6H), 2.10 (m, 1H), 3.21 (d, 2H), 4.16 (q, 2H), 5.01 (s, 2H), 5.49 (q, 1H), 6.36 (d, 1H), 6.40 (s, 1H), 6.75 (s, 1H) 6.84 (d, 2H), 6.91 (s, 1H), 6.97 (d, 2H), 7.32-7.43 (5H). |

Example 60

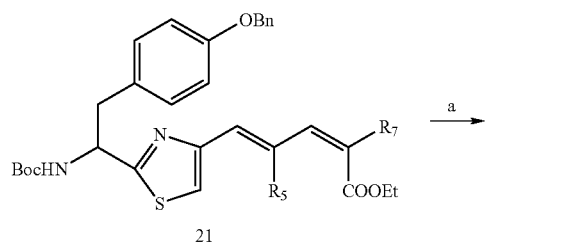

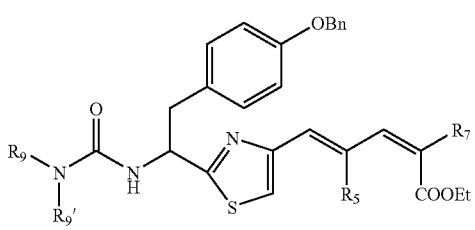

a. i) TFA, CH$_2$Cl$_2$; ii) R$_9$NHR$_9'$, CDI, THF.

The preparation of the compound 21 was the same as described in Example 1.

0.05 mmol compound 21 was dissolved in 1 mL dichloromethane, followed by dropwise addition of 0.3 mL trifluoroacetic acid. After the reaction mixture was reacted for 2 h, the solvent and trifluoroacetic acid were removed by rotary evaporation. 0.06 mmol R$_9$NHR$_9'$ was dissolved in 1 mL THF, followed by addition of 0.06 mmol carbonyldiimidazole. After the solution was stirred for 2 h, a solution of the above product in THF (0.5 mL) was added, and the reaction mixture was reacted overnight under refluxing. The solvent was removed by rotary evaporation, and the residue was purified through column chromatography (petroleum ether: ethyl acetate=4:1) to obtain compound 30 (yield: 50-90%).

TABLE 1-7
Final product 30
| Compound | Formula | $^1$H NMR (CDCl$_3$, 300 MHz) |
|---|---|---|
| WY951 | | δ 1.26 (t, 3H), 2.03 (s, 3H), 2.12 (s, 3H), 3.26 (dq, 2H), 4.21 (q, 2H), 5.03 (s, 2H), 5.46 (q, 1H), 6.27 (s, 1H), 6.45 (s, 1H), 6.86 (d, 2H), 6.97 (d, 2H), 7.04 (s, 1H), 7.32-7.44 (5H). |
| WY645s | | δ 1.22-1.32 (6H), 1.62 (m, 2H), 1.85 (m, 2H), 2.02 (s, 3H), 2.12 (s, 3H), 2.45 (m, 1H), 2.86 (m, 2H), 3.22 (m, 2H), 3.80 (m, 2H), 4.18 (m, 4H), 4.95 (d, 1H), 5.00 (s, 2H), 5.42 (br, 1H), 6.26 (br, 1H), 6.48 (br, 1H), 6.81 (d, 2H), 6.98 (br, 3H), 7.30-7.42 (5H). |
| WY617a | | δ 1.26 (t, 3H), 1.65 (m, 2H), 1.91 (m, 2H), 2.03 (s, 3H), 2.10 (s, 3H), 2.51 (m, 1H), 2.92 (m, 2H), 3.22 (dq, 2H), 3.85 (m, 2H), 4.20 (q, 2H), 5.01 (s, 2H), 5.42 (q, 1H), 5.59 (d, 1H), 6.27 (br, 1H), 6.49 (br, 1H), 6.84 (d, 2H), 6.97 (d, 3H), 7.00 (s, 1H), 7.30-7.42 (5H). |
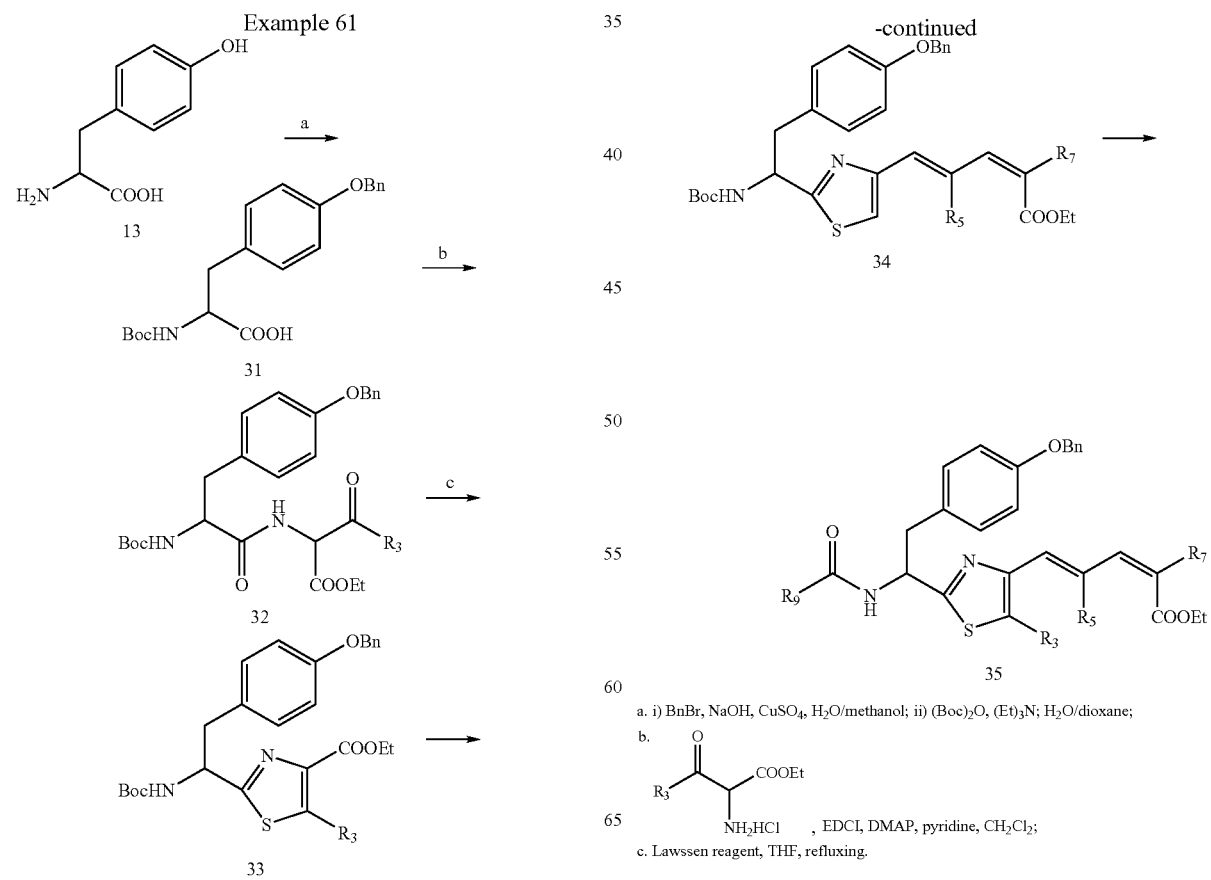
Example 61
a. i) BnBr, NaOH, CuSO$_4$, H$_2$O/methanol; ii) (Boc)$_2$O, (Et)$_3$N; H$_2$O/dioxane;
b. 
R$_3$―C(O)―CH(NH$_2$HCl)―COOEt, EDCI, DMAP, pyridine, CH$_2$Cl$_2$;
c. Lawssen reagent, THF, refluxing.

50 mmol compound 13 was dissolved in sodium hydroxide solution (100 mmol/50 mL), and stirred for 1.5 h, followed by dropwise addition of copper sulfate solution (25 mmol/25 mL). After the reaction mixture was stirred for 30 min, methanol was added, followed by dropwise addition of 51 mmol benzyl bromide. The reaction mixture was reacted for 3 h at room temperature, and filtrated under reduced pressure. The filter cake was washed with 2N HCl, and dried in vacuo. The obtained product was suspended in a mixture of 100 mL water and 100 mL 1,4-dioxane, followed by addition of 110 mmol triethylamine. After the reaction mixture was reacted for 1 h, 75 mmol (Boc)$_2$O was added therein, and the reaction was continued for 20 h. The reaction mixture was rotarily evaporated to dryness. The residue was diluted with ice water, and extracted with ethyl acetate. The water phase was adjusted to pH 2, and extracted with ethyl acetate. The organic phase was concentrated to obtain compound 31 (yield: 80%).

In 50 mL dichloromethane was dissolved 12 mmol compound 31 with 10 mmol CH$_3$COC(COOEt)NH$_2$HCl, 12 mmol EDCI, 2 mmol DMAP and 20 mmol pyridine. The reaction mixture was reacted overnight, and then diluted with ice water, and extracted with ethyl acetate. The organic phase was concentrated, and the residue was purified through column chromatography to obtain compound 32 (yield: 70%).

1 mmol compound 32 and 1.5 mmol Lawssen reagent were dissolved in 10 mL THF, and the reaction mixture was reacted overnight under refluxing. The solvent was removed by rotary evaporation, and the residue was purified through column chromatography to obtain compound 33 (yield: 60-95%).

With respect to the preparation of compound 34 from compound 33, please refer to the procedure described in Example 1 for preparing compound 20 from compound 16.

With respect to the preparation of compound 35 from compound 34, please refer to the procedure described in Example 14 for preparing compound 23 from compound 21.

TABLE 1-8

Final product (R$_5$ = R$_7$ = Me)

| Compound | R$_3$ | R$_9$ | Formula | $^1$H NMR (CDCl$_3$, 300 MHz) |
|---|---|---|---|---|
| WY586z | methyl | cyclohexyl | | δ 1.27 (t, 3H), 1.29-1.43 (4H), 1.66-1.86 (6H), 2.03 (s, 3H), 2.07 (m, 1H), 2.11 (s, 1H), 2.32 (s, 3H), 3.20 (dd, 2H) 4.20 (q, 2H), 5.02 (s, 2H), 5.45 (q, 1H), 6.28 (br, 2H), 6.31 (d, 1H), 6.84 (d, 2H), 6.99 (d, 2H), 6.99 (s, 1H), 7.31-7.42 (5H). |
| WY648z | phenyl | cyclohexyl | | δ 1.25 (t, 3H), 1.28-1.45 (4H), 1.68-1.88 (6H), 2.00 (s, 3H), 2.09 (m, 1H), 2.17 (s, 3H), 3.27 (m, 2H), 4.17 (q, 2H), 5.03 (s, 2H), 5.55 (q, 1H), 6.20 (s, 1H), 6.30 (d, 1H), 6.33 (s, 1H), 6.87 (d, 2H), 7.05 (d, 2H), 7.31-7.43 (10H). |
| WY628z | isobutyl | cyclohexyl | | δ 0.89 (d, 6H), 1.26 (t, 3H), 1.29-1.44 (4H), 1.66-1.85 (6H), 2.03 (s, 3H), 2.08 (m, 1H), 2.13 (s, 3H), 2.56 (d, 2H), 3.20 (m, 2H), 4.20 (q, 2H), 5.01 (s, 2H), 5.47 (q, 1H), 6.25 (br, 2H), 6.36 (d, 1H), 6.82 (d, 2H), 6.96 (d, 2H), 7.31-7.42 (5H). |
| WY662z | phenyl | cyclohexylmethyl | | δ 0.89 (m, 2H), 1.26 (t, 3H), 1.64-1.75 (9H), 2.00 (s, 3H), 2.07 (m, 2H), 2.18 (s, 3H), 3.27 (m, 2H), 4.17 (q, 2H), 5.02 (s, 2H), 5.58 (q, 1H), 6.20 (s, 1H), 6.23 (d, 1H), 6.34 (d, 1H), 6.87 (d, 2H), 7.07 (d, 2H), 7.31-7.50 (10H). |

TABLE 1-8-continued

Final product ($R_5 = R_7$ = Me)

| Compound | $R_3$ | $R_9$ | Formula | $^1$H NMR (CDCl$_3$, 300 MHz) |
|---|---|---|---|---|
| WY628z2 | iso-butyl | cyclo-hexyl | | δ 0.89 (d, 6H), 1.26 (t, 3H), 1.29-1.44 (4H), 1.66-1.85 (6H), 2.03 (s, 3H), 2.08 (m, 1H), 2.13 (s, 3H), 2.56 (d, 2H), 3.20 (m, 2H), 4.20 (q, 2H), 5.01 (s, 2H), 5.47 (q, 1H), 6.25 (br, 2H), 6.36 (d, 1H), 6.82 (d, 2H), 6.96 (d, 2H), 7.31-7.42 (5H). |

Example 62

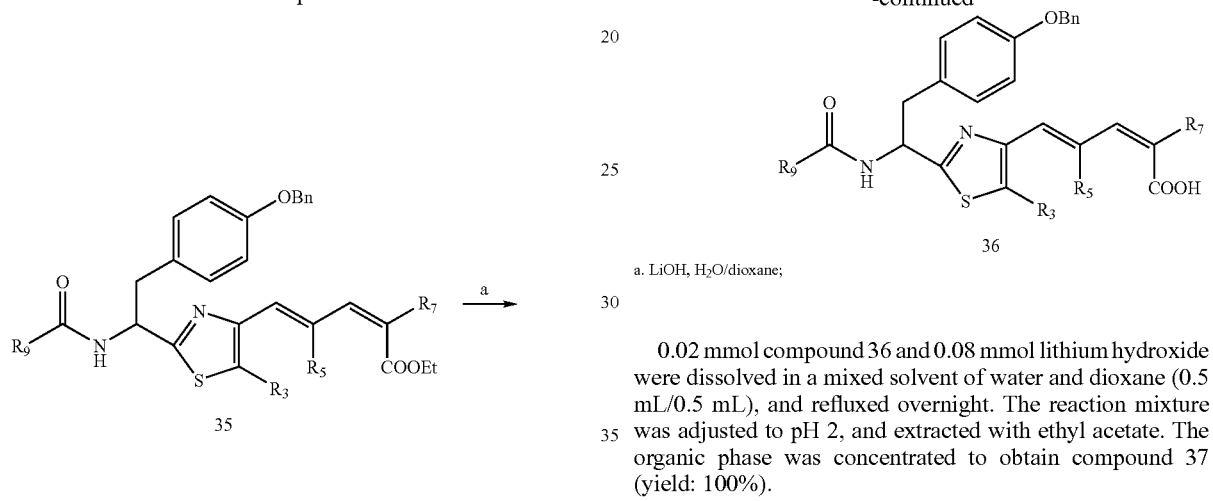

a. LiOH, H$_2$O/dioxane;

0.02 mmol compound 36 and 0.08 mmol lithium hydroxide were dissolved in a mixed solvent of water and dioxane (0.5 mL/0.5 mL), and refluxed overnight. The reaction mixture was adjusted to pH 2, and extracted with ethyl acetate. The organic phase was concentrated to obtain compound 37 (yield: 100%).

TABLE 1-9

Final product 37

| Compound | Formula | 1H NMR (CDCl3, 300 MHz) |
|---|---|---|
| WY544a | | δ 1.30-1.44 (4H), 1.66-1.80 (6H), 2.03 (s, 3H), 2.07 (m, 1H), 2.15 (s, 3H), 3.19 (br, 2H), 5.00 (s, 2H), 5.53 (q, 1H), 6.36 (s, 1H), 6.58 (s, 1H), 6.84 (d, 2H), 6.98 (d, 2H), 7.01 (s, 1H), 7.30-7.42 (5H). |
| WY544-2 | | δ1.30-1.44 (4H), 1.66-1.80 (6H), 2.10 (s, 3H), 2.15 (br, 1H), 2.30 (s, 3H), 3.00 (d, 2H), 4.49 (d, 1H), 5.06 (s, 2H), 5.20 (m, 2H), 6.60 (s, 1H), 6.91 (d, 2H), 7.17 (s, 1H), 7.18 (d, 2H), 7.31-7.44 (5H), 7.56 (s, 1H), 8.46 (d, 1H). |

TABLE 1-9-continued

Final product 37

| Compound | Formula | 1H NMR (CDCl3, 300 MHz) |
|---|---|---|
| WY558a | | δ 0.85(m, 2H), 1.16 (m, 3H), 1.62-1.72 (6H), 2.03 (s, 3H), 2.07 (m, 2H), 2.14 (s, 3H), 3.22 (d, 2H), 4.99 (s, 2H), 5.54 (q, 1H), 6.34 (s, 1H), 6.58 (s, 1H), 6.83 (d, 2H), 6.95 (d, 1H), 7.01 (br, 3H), 7.27-7.39 (5H). |
| WY620a | | δ 1.34-1.42 (4H), 1.63-1.78 (6H), 2.05 (s, 3H), 2.08 (m, 1H), 2.17 (s, 3H), 3.23 (d, 2H), 5.00 (s, 2H), 5.54 (q, 1H), 6.29 (s, 1H), 6.36 (s, 1H), 6.85 (d, 2H), 6.91 (d, 1H), 7.06 (d, 2H), 7.28-7.39 (10H). |
| WY634a | | δ 0.89 (m, 2H), 1.64-1.75 (9H), 2.01 (m, 2H), 2.03 (s, 3H), 2.15 (s, 3H), 3.22 (d, 2H), 4.98 (s, 2H), 5.57 (q, 1H), 6.28 (s, 1H), 6.38 (d, 1H), 6.85 (d, 2H), 7.07 (d, 2H), 7.30-7.38 (10H). |

EXPERIMENTAL EXAMPLE 1

PTP1B Inhibition Test

1) Test principle: The catalytic structural domain of hPTP1B was expressed in E-coli system by a molecular biology protocol. The purified hPTP1B recombinant protein can hydrolyze the phosphoester linkage of the pNPP substrate to obtain a product which has a strong light absorption at 410 nm. Therefore, the variation of the enzyme activity and the inhibitory activity of a compound against the enzyme can be observed by directly monitoring the changes in the light absorption at 410 nm. A typical activity assay system is as follows: 50 mM Mops, PH 7.0, 1 mM EDTA, 2 mM DTT, 2 mM PNPP, 2% DMSO, 40 nM hPTP1B.

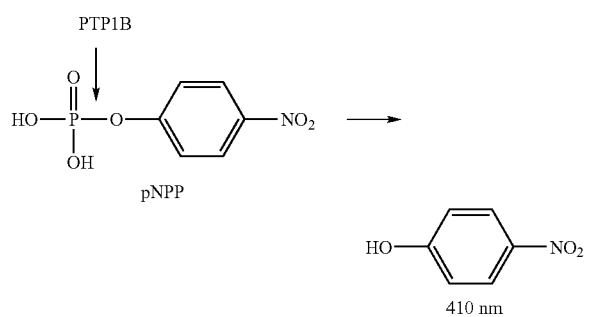

2) Measuring Index: The light absorption was dynamically measured at 410 nm for 3 min. The slope of the first-order reaction of the dynamic curve thereof was considered as the activity index of the enzymes.

3) Measurement:
1. 1 mg sample was dissolved in 200 μL DMSO. To each wall of the A2-H11 of a 96-wells polypropylene plate, 20 μL of the solution was added, followed by addition of 80 μL DMSO. The plate was used as mother plate.
2. To each corresponding wall of a 96-wells polypropylene plate, 2 μL of sample was added with a Biomek 2000 automation workstation. The plate was used as daughter plate for screening.
3. To each wall of A1-D1 and E12-H12, 2 μL, DMSO was added. These walls were regarded as 100% of enzyme activity for control.
4. To each wall of A12-D12 and E1-H1, 2 μL positive control with different concentrations (four concentrations prepared by double-fold dilution from 10 μL/mL) was added respectively.
5. To each wall of A1-H12, 88 μL Assay mix was added respectively.
6. To each wall of A1-H12, 10 μL hPTP1B was added respectively.
7. The light absorption was measured at 410 nm for 3 min on a SpectraMAX 340 spectrometer.
8. Exporting the output into a TXT file, and opening the file with Excel. The average of the Vmax values of A1-D1 and E12-H12 was considered as 100% of enzyme activity. The inhibitory rate of the compound against PTP1B was calculated by the following equation:

% inhibitory rate=(1−$V$max value of each screening wall/average of the $V$max values of blank control walls)*100%

4) Results: The screening results were the % inhibitory rate against the enzyme when the compound concentration was 20 μg/mL. 1050 value was calculated according to a conventional screening when the inhibitory rate exceeded 50%. The 1050 value of the positive control, 4-[4-(4-oxalyl-phenoxymethyl)-benzyloxy]-phenyl-oxo-acetic acid, is 5.4 μM [Christopher T. Seto, et al. J. Med. Chem., 2002, 45, 3946-3952]. The IC50 value of each test compound against hPTP1B is listed in Table 2.

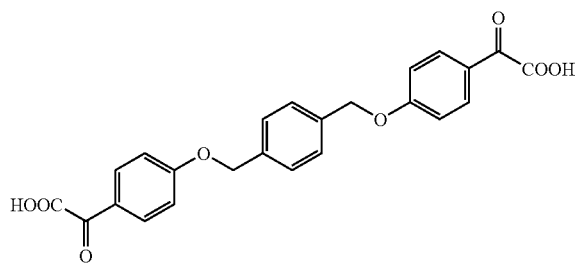

4-[4-(4-oxalyl-phenoxymethyl)-benzyloxy]-phenyl-oxo-acetic acid

TABLE 2

Inhibitory activity of the test compounds against PTP1B

| compound | IC$_{50}$(μM) |
|---|---|
| WY558 | 8.14 |
| WY572 | 8.52 |
| WY600 | 3.44 |
| WY574 | 8.58 |
| WY612 | 5.13 |
| WY600t | 10.92 |
| WY548 | >35 |
| WY566s | 15.20 |
| WY622s | 25.59 |
| WY560t | 20.18 |
| WY586d | 8.44 |
| WY586s | 2.48 |
| WY558f | >35 |
| WY602-2 | 13.54 |
| WY544s | >40 |
| WY530s | >35 |
| WY556s | >40 |
| WY584 | >35 |
| WY578h | 11.97 |
| WY496h | 30.14 |
| WY538h | 22.12 |
| WY590h | 25.59 |
| WY590h3 | 24.10 |
| WY602h | 25.55 |
| WY540a | >40 |
| WY526h | >40 |
| WY622h | >35 |
| WY586h | >35 |
| WY573h4 | >40 |
| WY542h | >40 |
| WY572-2 | 6.38 |
| WY572-4 | 7.90 |
| WY544-2 | 11.25 |
| WY648z | 3.30 |
| WY586z | 4.86 |
| WY558a | 9.32 |
| WY620a | 4.00 |
| WY645s | 10.48 |
| WY562 | 10.25 |
| WY586 | 10.98 |
| WY588 | 10.44 |
| WY594 | 6.92 |
| WY638 | 4.10 |
| WY583 | >35 |
| WY532s | 20.85 |
| WY580s | 23.10 |

TABLE 2-continued

Inhibitory activity of the test compounds against PTP1B

| compound | IC$_{50}$(μM) |
|---|---|
| WY610s | 9.42 |
| WY572s | 6.29 |
| WY652s | 9.98 |
| WY558s | 12.72 |
| WY596s | 44.78 |
| WY584s | >35 |
| WY562s | >40 |
| WY560s | >40 |
| WY532s | >40 |
| WY587s | >35 |
| WY466h | 34.23 |
| WY482h | 27.83 |
| WY522h | 34.36 |
| WY592h2 | 31.75 |
| WY560h | 12.32 |
| WY568h | >40 |
| WY582h | >35 |
| WY597h | >35 |
| WY621h | >35 |
| WY573h | >35 |
| WY560h | >40 |
| WY522b | >40 |
| WY572-3 | 8.69 |
| WY544a | 4.40 |
| WY628z | 6.68 |
| WY572t | 4.47 |
| WY951 | 6.29 |
| WY634a | 3.97 |
| WY628z2 | 10.48 |
| WY617a | 6.47 |

EXPERIMENTAL EXAMPLE 2

Effect of the Compound WY586s on the Phosphorylation Level of IRs in CHO/IR Cells 1). Experimental principle: The phosphorylation levels of insulin receptors (IRs) in cells sensitive to insulin are regulated by PTK and PTPase. PTP1B is a negative regulator during the process. It can be evaluated by measuring the phosphorylation level of IRs in CHO/IR cells whether the PTP inhibitor has entered into the cells and how its effect in cells is.

2). Experimental Protocol:
1. Cell inoculation: Cells in good growth condition were inoculated into a 6-well plate with a density of $3-4 \times 10^5$ cells/well. To each well was added 2 mL F12 culture media containing 10% FBS.
2. Starvation: After cultivation for 24 h, to each well was added 2 mL serum-free F12 culture media. Then the plate was cultivated overnight.
3. Administration: After removing the old culture media, to each well was added 0.9 mL serum-free F12 culture media containing the test compound, wherein 1 mM Na$_3$VO$_4$ and 0.1% DMSO were used as positive and negative control, respectively. The plate was incubated for 2-4 h.
4. Insulin stimulation: To each well was added 100 μL 100 nM insulin solution so that the final concentration was 10 nM. The reaction was carried out for 10 min.
5. Sample collection: After discarding the culture media, to each well was added 150 μL×1 loading buffer. The cells were lysed, and the samples were collected.

3). Experimental results: The experiment evaluated the effect of WY586s on the phosphorylation levels of insulin receptors in CHO/IR cells. The final concentration of test compound, WY586s, was set at 0.21, 0.43, 0.85, 1.70 μM, respectively. The DMSO solvent was used as negative control (represented with 0), and sodium vanadate was used as positive compound (represented with V). As shown in FIG. 1, p-IR is the phosphorylated insulin receptor, representing the activity level of insulin receptor; IRβ is the insulin receptor β-subunit, representing the basal expression level of insulin receptor; β-activated protein was used as internal control, representing total loading amount. It is shown from the investigation on the compound of WY586s that the phosphorylation level of IR significantly increases with the increase of the concentration of the inhibitor. Therefore, it can be seen that WY586s plays an inhibitory function in the dephosphorylation of IR in cells, and can improve the insulin sensitivity of cells, indicating that this class of compounds can enhance the effect of insulin, and release insulin resistance to a certain extent.

What is claimed is:

1. A compound of formula I,

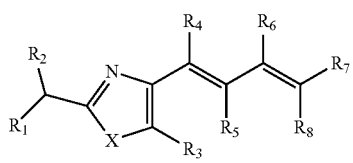

wherein X is S, O, or NH;

$R_1$ is $OCOR_9$, $OCOCOR_9$, $NHCOR_9$, $NHCOCOR_9$, $NHCONHR_9$,

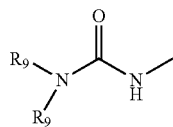

or $CH_2R_9$;

wherein $R_9$ and $R_9'$ are each independently C2-C6 alkenyl; C1-C2 alkoxycarbonyl; C3-C6 cycloalkyl, or C3-C6 cycloalkyl wherein one or more carbon atoms may be replaced by O, N or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubstituted phenyl, substituted or unsubstituted benzyl, 5- or 6-membered aromatic cyclic group wherein one or more carbon atoms may be replaced by O, N or S, C3-C6 cycloalkyl, C3-C6 cycloalkyl wherein one or more carbon atoms may be replaced by O, N or S, or hydroxyl; 5- or 6-membered aromatic cyclic group wherein one or more carbon atoms may be replaced by O, N or S, or benzo-fused 5- or 6-membered aromatic cyclic group wherein one or more carbon atoms may be replaced by O, N or S; C1-C4 alkyl having carboxyl, methoxycarbonyl or ethoxycarbonyl; or $CH_2OR_{13}$, wherein, $R_{13}$ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl wherein one or more carbon atoms may be replaced by O, N or S;

$R_2$ is

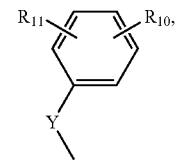

wherein,

Y is C1-C6 alkylene;

$R_{10}$ is H; halogen; hydroxyl; C2-C6 alkenyl; C1-C13 alkyl substituted by halogen, C1-C6 alkoxyl, phenyl, benzyloxy or hydroxyl; phenyl, naphthyl, or phenyl substituted by halogen, carboxyl, C1-C6 alkyl or alkoxyl; benzyl, or benzyl substituted by halogen, C1-C6 alkyl or alkoxyl; C1-C4 alkyl having carboxyl, methoxycarbonyl or ethoxycarbonyl; $OCH_2R_{12}$ or $OR_{12}$; wherein, $R_{12}$ is H; C2-C6 alkenyl; C1-C13 alkyl substituted by halogen, C1-C6 alkoxyl, phenyl or hydroxyl; C1-C4 alkyl having carboxyl, methoxycarbonyl or ethoxycarbonyl; thiazolyl, furyl, thienyl, pyranyl, pyridyl, benzothiazolyl, benzothienyl, naphthyl; benzyl; phenyl, or phenyl substituted by halogen, C1-C6 alkoxyl or hydroxyl; C3-C6 cycloalkyl, or 5- or 6-membered cycloalkyl wherein one or more carbon atoms may be replaced by O, N or S;

$R_{11}$ is H; hydroxyl; halogen; C1-C6 alkyl; or C1-C6 alkoxyl;

$R_3$ is H; halogen; C2-C6 alkenyl; C1-C2 alkoxycarbonyl; C3-C6 cycloalkyl, C3-C6 cycloalkyl substituted by halogen or carboxyl, or 5- or 6-membered cycloalkyl wherein one or more carbon atoms may be replaced by O, N or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl or hydroxyl; 5- or 6-membered aromatic cyclic group wherein one or more carbon atoms may be replaced by O, N or S, or benzo-fused 5- or 6-membered aromatic cyclic group wherein one or more carbon atoms may be replaced by O, N or S; C1-C4 alkyl having carboxyl, methoxycarbonyl or ethoxycarbonyl;

$R_4$, $R_5$, $R_6$ and $R_7$ are each independently H; halogen; C2-C6 alkenyl; C3-C6 cycloalkyl; phenyl or halogenated phenyl; benzyl; C1-C13 alkyl substituted by halogen, C1-C6 alkoxyl or hydroxyl; C1-C4 alkyl having carboxyl, methoxycarbonyl or ethoxycarbonyl;

wherein, the double bond between $R_4$ and $R_5$ can be in a cis- or trans-configuration; the double bond between $R_6$ and $R_7$ can be in a cis- or trans-configuration;

$R_8$ is carboxyl, methoxycarbonyl or ethoxycarbonyl.

2. A compound according to claim 1, wherein, $R_3$ is H or phenyl; $R_4$, $R_5$, $R_6$ and $R_7$ are each independently H or C1-C4 alkyl; $R_8$ is carboxyl, methoxycarbonyl or ethoxycarbonyl.

3. A compound according to claim 1 having a structure represented by the following formula III,

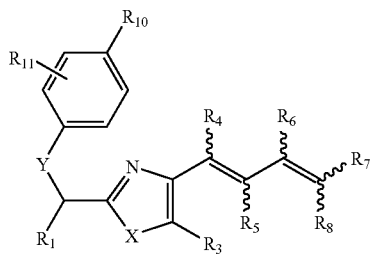

wherein X, $R_1$, $R_3$-$R_8$, Y and $R_{10}$-$R_{11}$ are the same as defined in claim 1.

4. A compound according to claim 1 or 3, wherein
Y is —$CH_2$—;
$R_{10}$ is H; hydroxyl; phenyl; —$OCH_3$; —$OCH_2CH$=$CH_2$; —$OCH_2COOEt$; —$OCH_2COOH$; —OBn; 2-ethoxycarhonylethoxy; 2-hydroxylethoxy; butoxy; 4-cyanobenzyloxy; 4-fluorobenzyloxy; 4-methoxybenzyloxy; 3-fluorobenzyloxy; 2-fluorobenzyloxy; 2-naphthylmethoxy; 4-nitro-2-fluorophenoxy; phenylethoxy; 1-pyridylmethoxy; 4-pyridylmethoxy; 2-furylmethoxy; 2-pyranylmethoxy;
$R_{11}$ is H.

5. A compound according to claim 3, having a structure represented by the following formula IV,

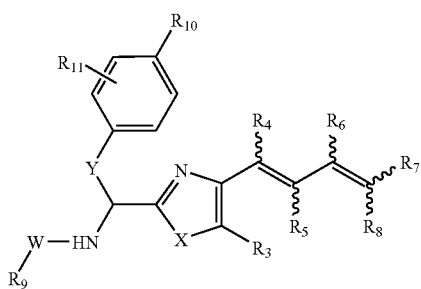

wherein X, $R_3$-$R_8$, Y and $R_{10}$-$R_{11}$ are the same as defined in claim 3;
$R_9$ is C2-C6 alkenyl; C1-C2 alkoxycarbonyl; C3-C6 cycloalkyl, or C3-C6 cycloalkyl wherein one or more carbon atoms may be replaced by O, N or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubstituted phenyl, substituted or unsubstituted benzyl, 5- or 6-membered aromatic cyclic group wherein one or more carbon atoms may be replaced by O, N or S, C3-C6 cycloalkyl, C3-C6 cycloalkyl wherein one or more carbon atoms may be replaced by O, N or S, or hydroxyl; 5- or 6-membered aromatic cyclic group wherein one or more carbon atoms may be replaced by O, N or S, or benzo-fused 5- or 6-membered aromatic cyclic group wherein one or more carbon atoms may be replaced by O, N or S; C1-C4 alkyl having carboxyl, methoxycarbonyl or ethoxycarbonyl; or $CH_2OR_{13}$;

wherein, $R_{13}$ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl wherein one or more carbon atoms may be replaced by O, N or S;

W is CO, CO—CO, CO—NH or CO—$NR_9$';

wherein, $R_9$' is C2-C6 alkenyl; C1-C2 alkoxycarbonyl; C3-C6 cycloalkyl, or C3-C6 cycloalkyl wherein one or more carbon atoms may be replaced by O, N or S; phenyl naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubstituted phenyl, substituted or unsubstituted benzyl, 5- or 6-membered aromatic cyclic group wherein one or more carbon atoms may be replaced by O, N or S, C3-C6 cycloalkyl, C3-C6 cycloalkyl wherein one or more carbon atoms may be replaced by O, N or S, or hydroxyl; 5- or 6-membered aromatic cyclic group wherein one or more carbon atoms may be replaced by O, N or S, or benzo-fused 5- or 6-membered aromatic cyclic group wherein one or more carbon atoms may be replaced by O, N or S; C1-C4 alkyl having carboxyl, methoxycarbonyl or ethoxycarbonyl; or $CH_2OR_{13}$;

wherein, $R_{13}$ is phenyl or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl wherein one or more carbon atoms may be replaced by O, N or S.

6. A compound according to claim 5, having a structure represented by the following formula V or VI,

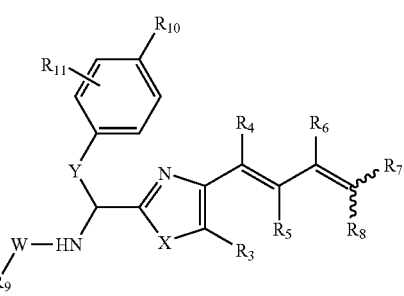

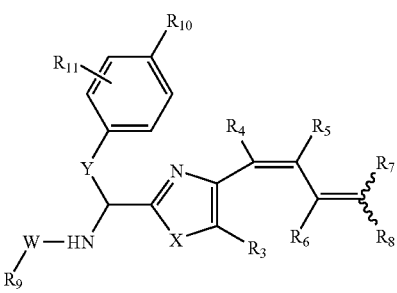

wherein X, Y, W, $R_3$-$R_8$, $R_9$ and $R_{10}$-$R_{11}$ are the same as defined in claim 5.

7. A compound according to claim 5, having a structure represented by the following formula VII,

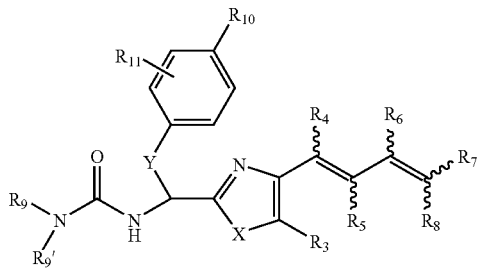

wherein X, Y, $R_3$-$R_8$, $R_9$ and $R_{10}$-$R_{11}$ are the same as defined in claim 6;
$R_9'$ is C2-C6 alkenyl; C1-C2 alkoxycarbonyl; C3-C6 cycloalkyl, or C3-C6 cycloalkyl wherein one or more carbon atoms may be replaced by O, N or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubstituted phenyl, substituted or unsubstituted benzyl, 5- or 6-membered aromatic cyclic group wherein one or more carbon atoms may be replaced by O, N or S, C3-C6 cycloalkyl, C3-C6 cycloalkyl wherein one or more carbon atoms may be replaced by O, N or S, or hydroxyl; 5- or 6-membered aromatic cyclic group substituted by O, N and/or S, or benzo-fused 5- or 6-membered aromatic cyclic group wherein one or more carbon atoms may be replaced by O, N or S; C1-C4 alkyl having carboxyl, methoxycarbonyl or ethoxycarbonyl; or $CH_2OR_{13}$;
wherein, $R_{13}$ is phenyl, or phenyl substituted by halogen, C1-C6 alkoxyl or hydroxyl; benzyl, or benzyl substituted by halogen, C1-C6 alkoxyl or hydroxyl; thiazolyl, furyl, thienyl, pyranyl, pyridyl, benzothiazolyl, benzothienyl, naphthyl; C3-C6 cycloalkyl, or C3-C6 cycloalkyl wherein one or more carbon atoms may be replaced by O, N or S.

8. A compound according to any one of claims 5-6, wherein,
$R_3$ is H or phenyl;
$R_4$, $R_5$, $R_6$ and $R_7$ are each independently H or C1-C4 alkyl;
$R_8$ is carboxyl, methoxycarbonyl or ethoxycarbonyl;
$R_9$ is C2-C6 alkenyl; C1-C2 alkoxycarbonyl; C3-C6 cycloalkyl, or C3-C6 cycloalkyl wherein one or more carbon atoms may be replaced by O, N or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubstituted phenyl, substituted or unsubstituted benzyl, 5- or 6-membered aromatic cyclic group wherein one or more carbon atoms may be replaced by O, N or S, C3-C6 cycloalkyl, C3-C6 cycloalkyl wherein one or more carbon atoms may be replaced by O, N or S, or hydroxyl; 5- or 6-membered aromatic cyclic group wherein one or more carbon atoms may be replaced by O, N or S, or benzo-fused 5- or 6-membered aromatic cyclic group wherein one or more carbon atoms may be replaced by O, N or S; C1-C4 alkyl having carboxyl, methoxycarbonyl or ethoxycarbonyl;
Y is —$CH_2$—;
W is CO;
$R_{10}$ is H; hydroxyl; phenyl; —$OCH_3$; —$OCH_2CH=CH_2$; —$OCH_2COOEt$; —$OCH_2COOH$; —OBn; 2-ethoxycarbonylethoxy; 2-hydroxylethoxy; butoxy; 4-cyanobenzyloxy; 4-fluorobenzyloxy; 4-methoxybenzyloxy; 3-fluorobenzyloxy; 2-fluorobenzyloxy; 2-naphthylmethoxy; 4-nitro-2-fluorophenoxy; phenylethoxy; 1-pyridylmethoxy; 4-pyridylmethoxy; 2-furylmethoxy; 2-pyranylmethoxy;
$R_{11}$ is H.

9. A compound according to claim 5, having a structure represented by the following formula VIII,

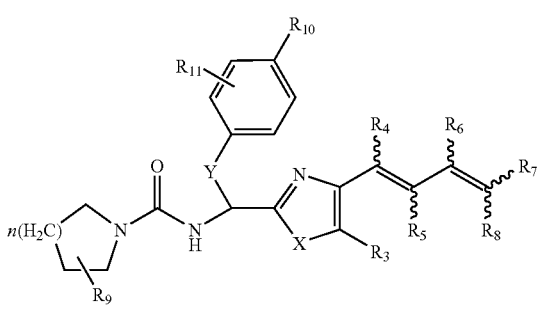

wherein X, Y, $R_3$-$R_8$, $R_9$ and $R_{10}$-$R_{11}$ are the same as defined in claim 6;
n=0, 1, 2, or 3.

10. A compound according to claim 9, wherein,
n=0;
$R_9$ is C2-C6 alkenyl; C1-C2 alkoxycarbonyl; C3-C6 cycloalkyl, or C3-C6 cycloalkyl wherein one or more carbon atoms maybe replaced by O, N or S; phenyl, naphthyl, or phenyl substituted by halogen, carboxyl or C1-C6 alkoxyl; benzyl, or benzyl substituted by halogen, carboxyl or C1-C6 alkoxyl; C1-C13 alkyl substituted by halogen, carboxyl, substituted or unsubstituted phenyl, substituted or unsubstituted benzyl, 5- or 6-membered aromatic cyclic group wherein one or more carbon atoms may be replaced by O, N or S, C3-C6 cycloalkyl, C3-C6 cycloalkyl wherein one or more carbon atoms may be replaced by O, N or S, or hydroxyl; 5- or 6-membered aromatic cyclic group wherein one or more carbon atoms ay be replaced by O, N or S, or benzo-fused 5- or 6-membered aromatic cyclic group wherein one or more carbon atoms may be replaced by O, N or S; C1-C4 alkyl having carboxyl, methoxycarbonyl or ethoxycarbonyl.

11. A compound selected from a group consisting of

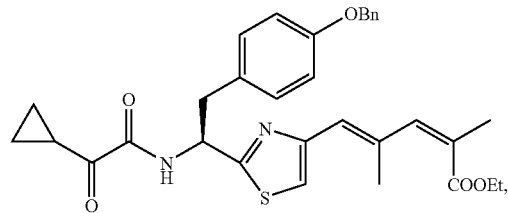

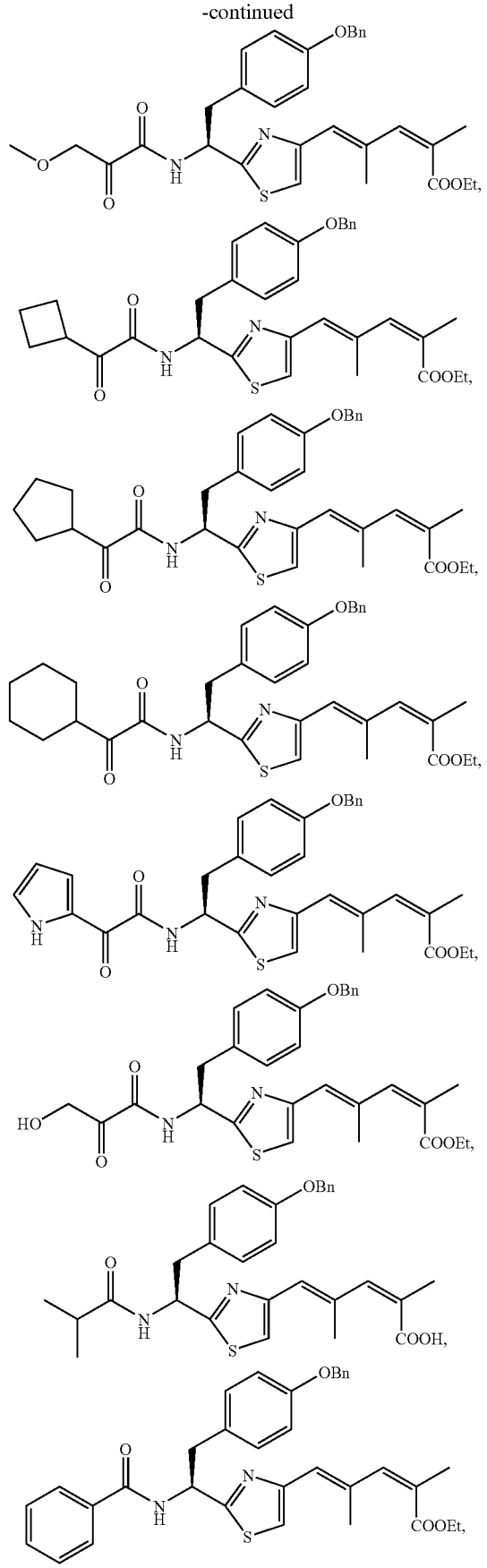
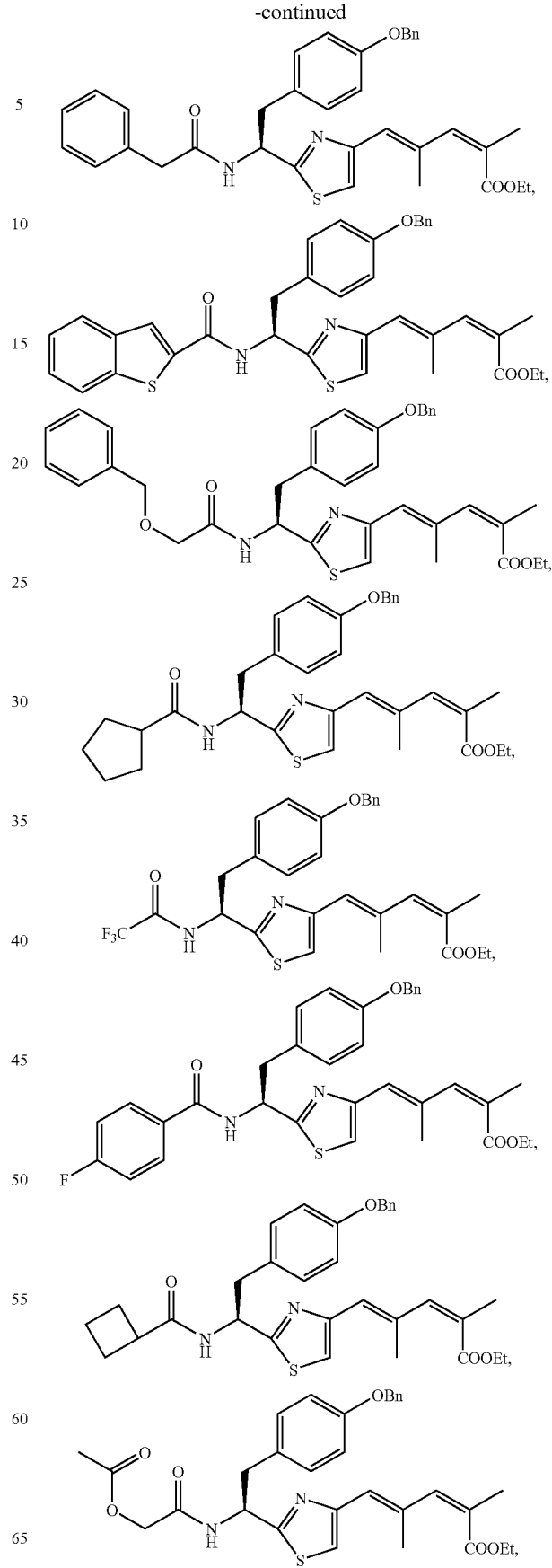

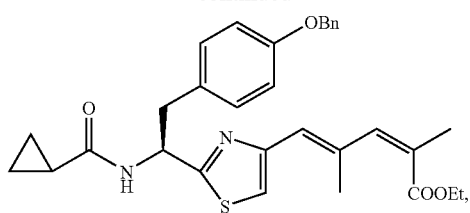
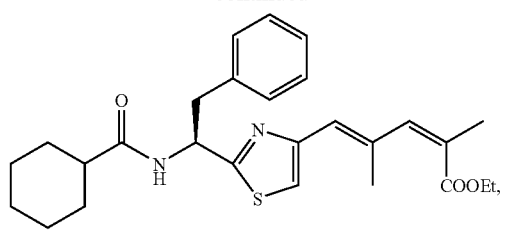
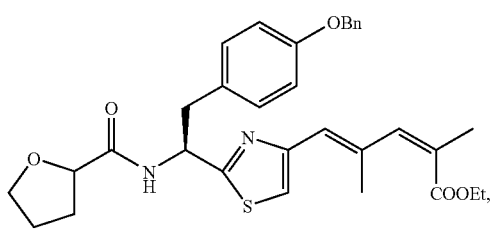
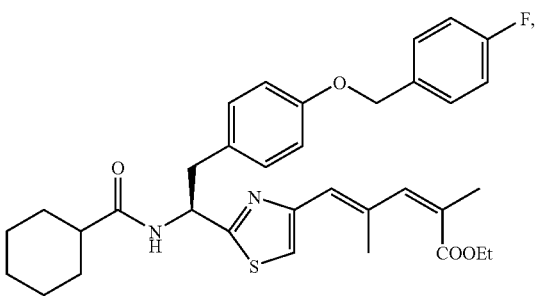
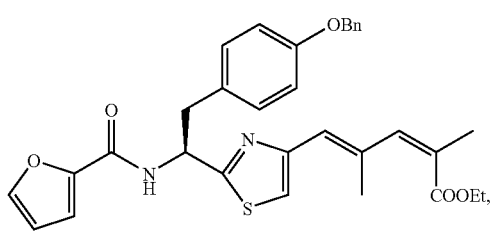
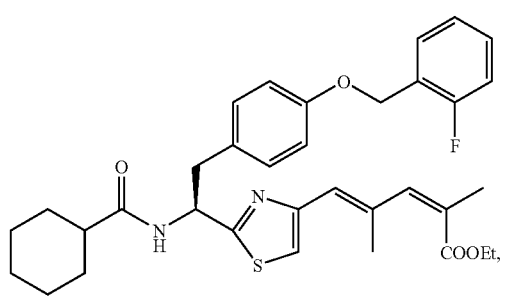
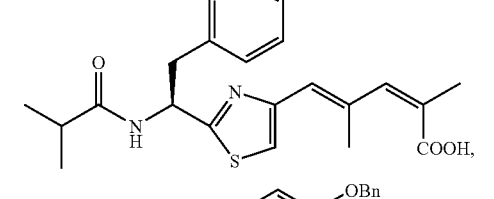
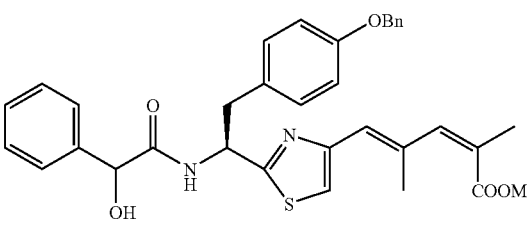
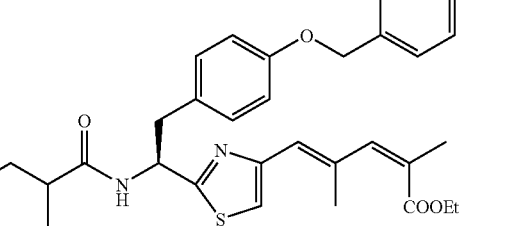
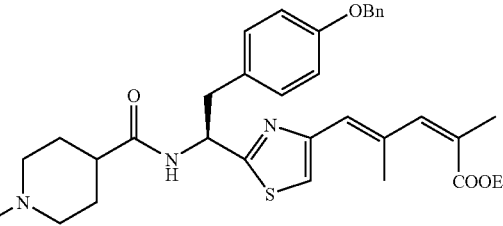
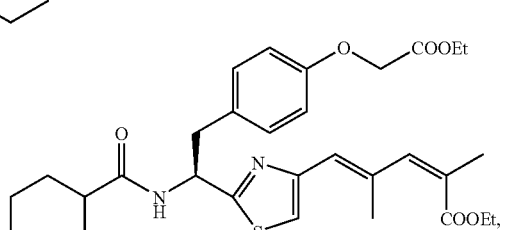
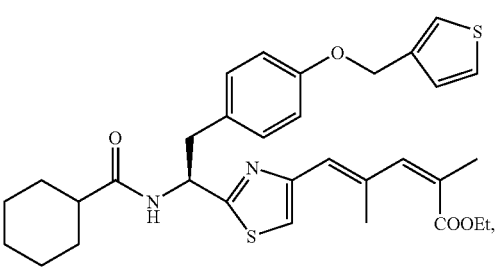
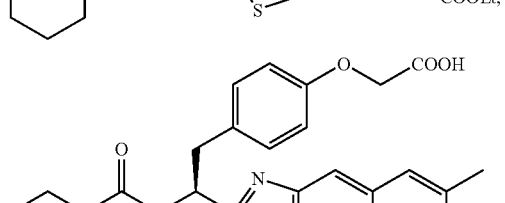
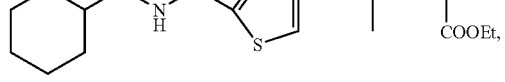

81
-continued
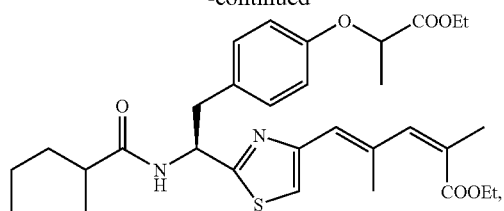
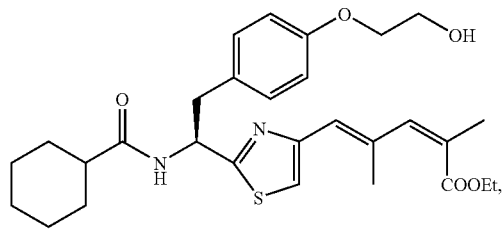
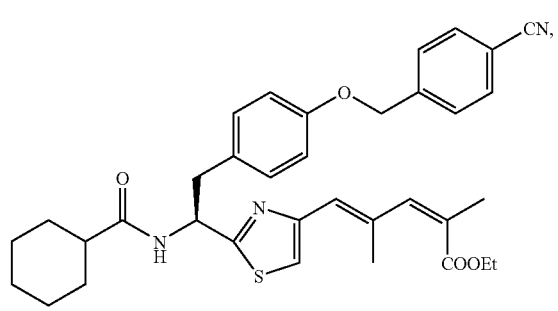
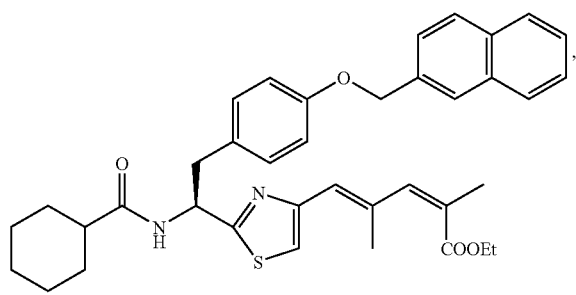
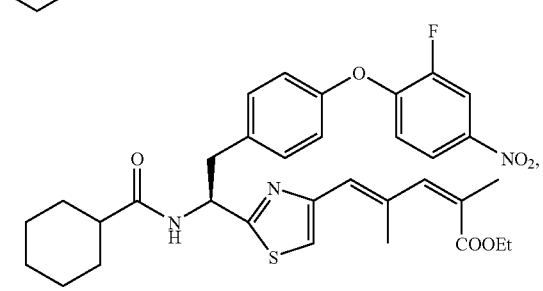
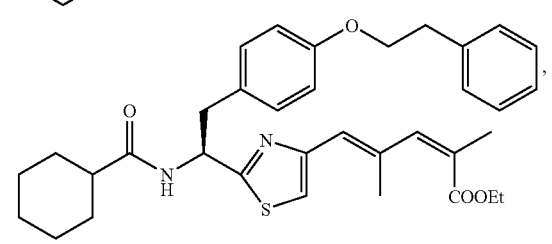
82
-continued
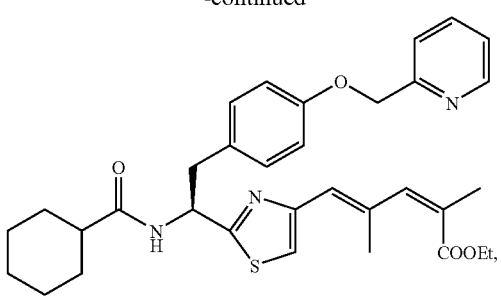
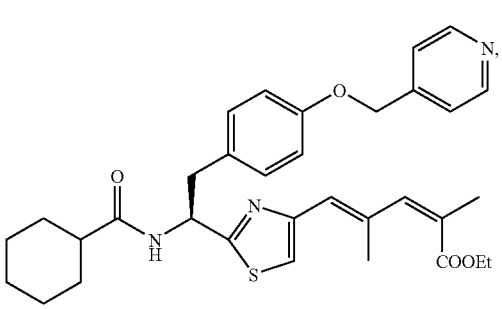
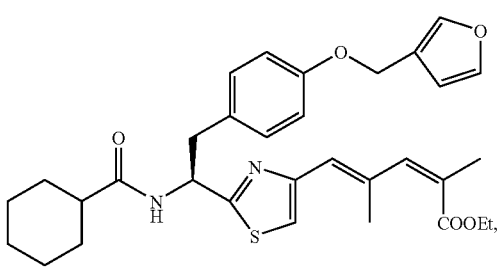
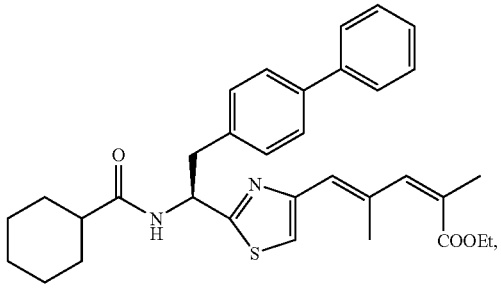
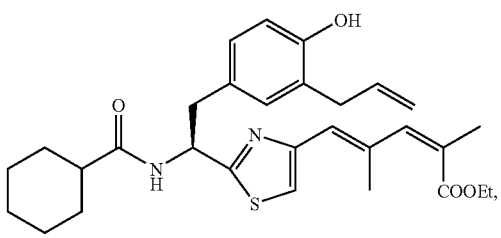
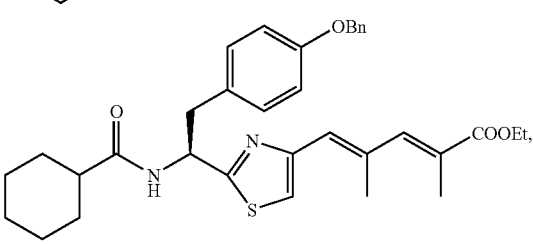

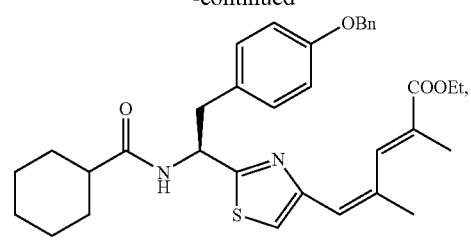
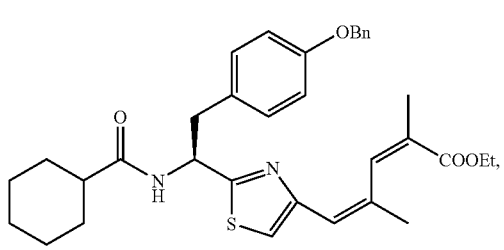
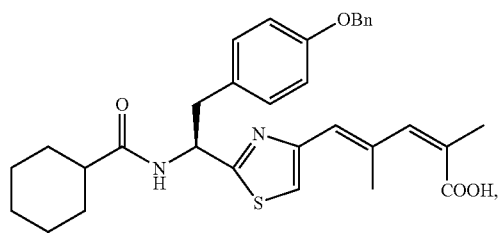
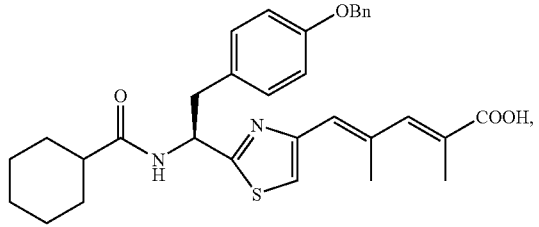
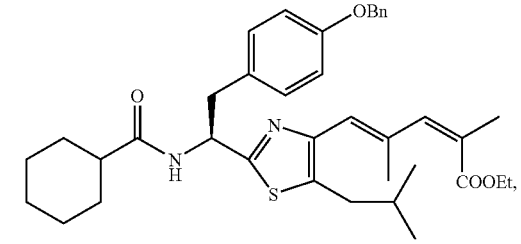
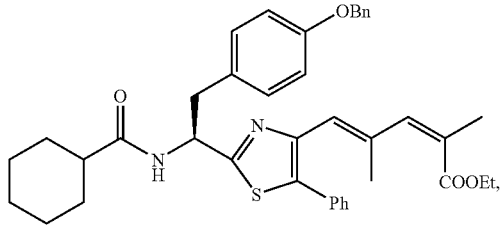
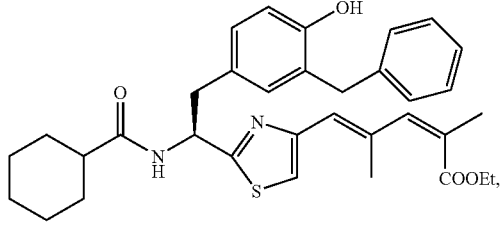
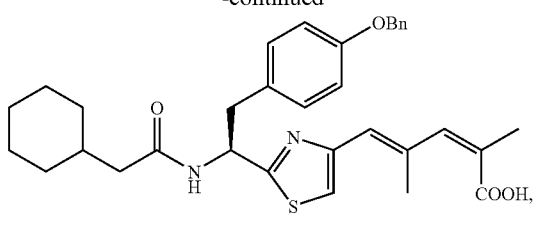
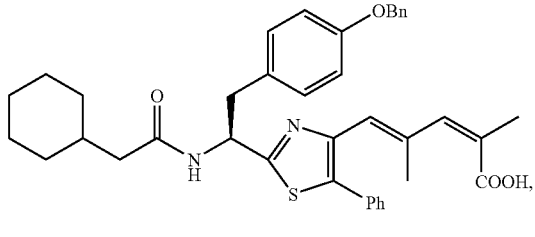
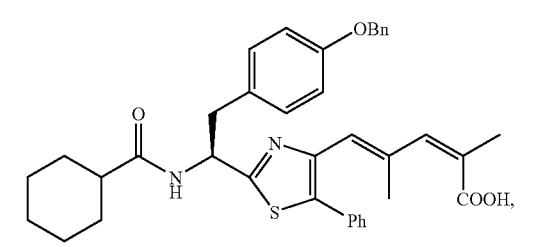
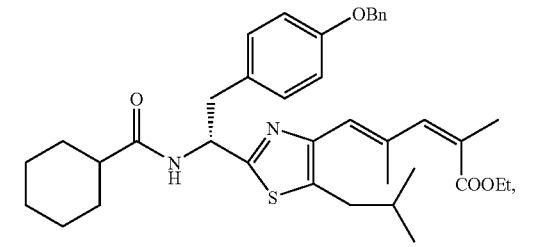
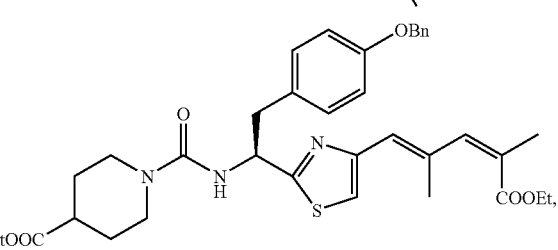
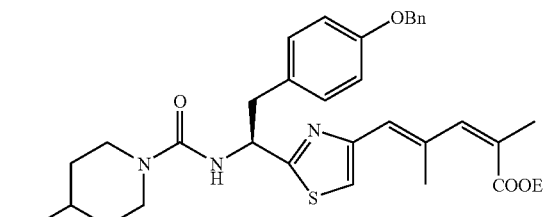
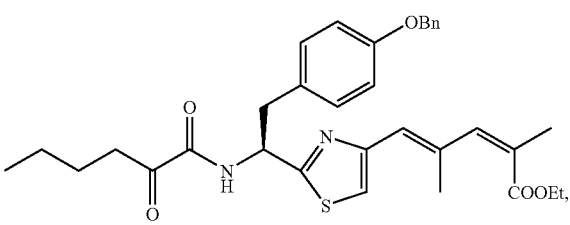

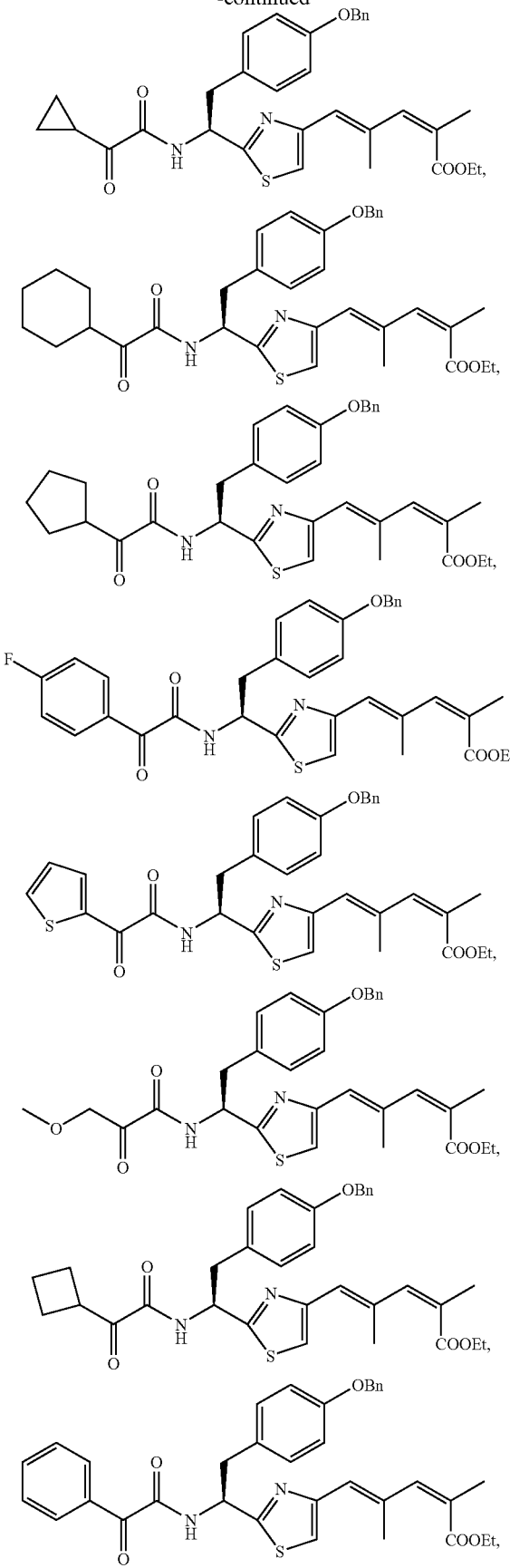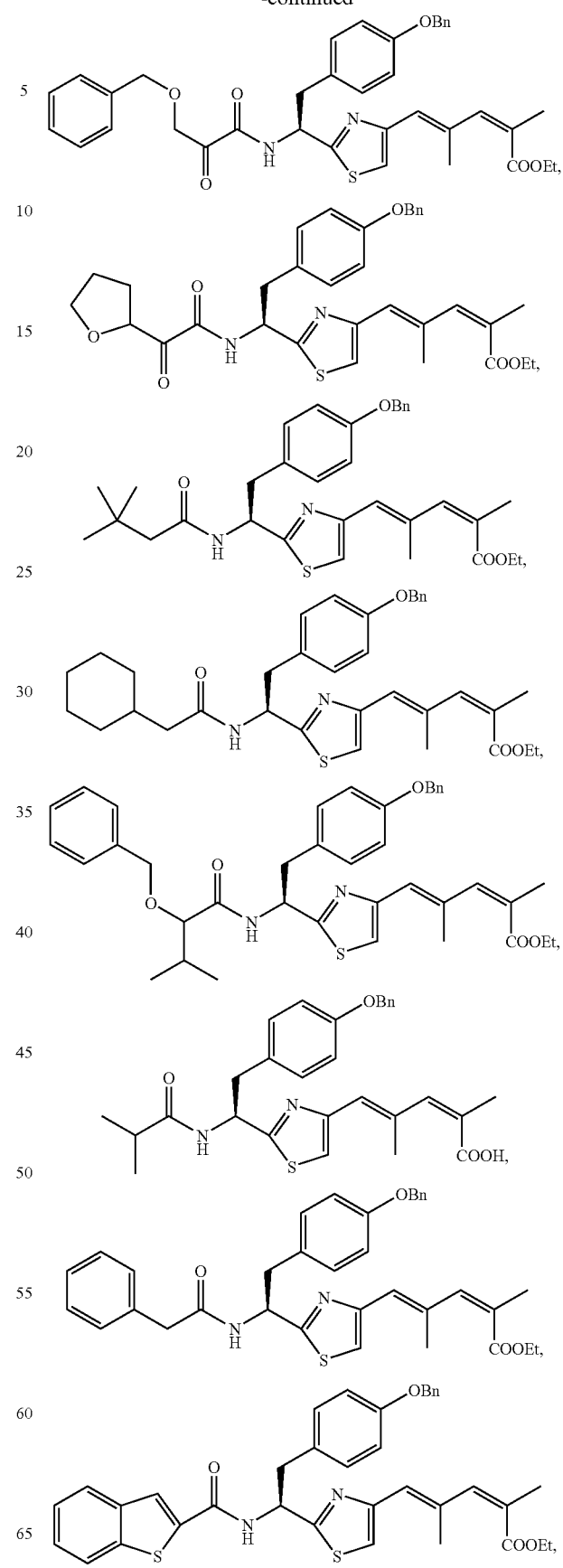

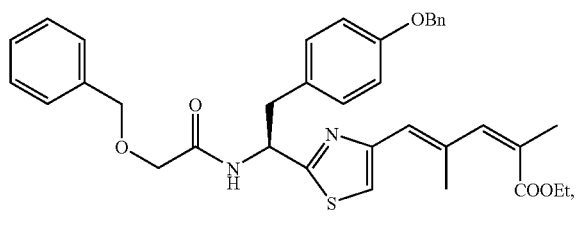
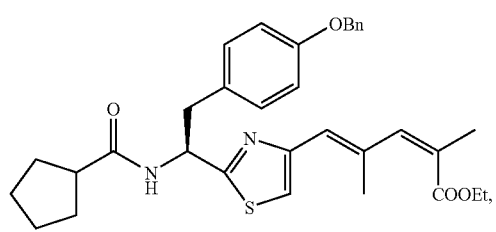
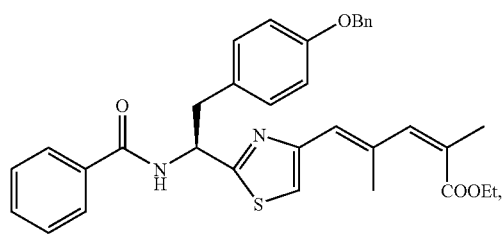
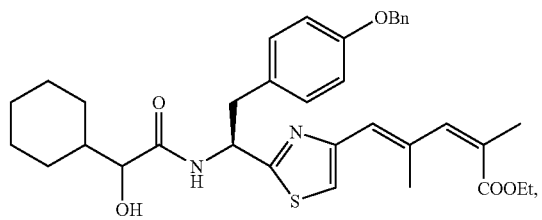
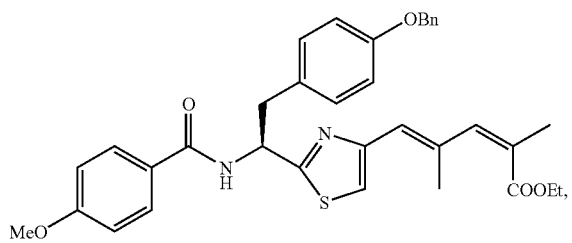
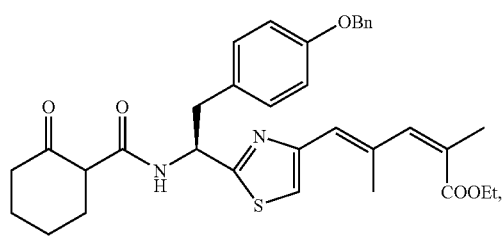
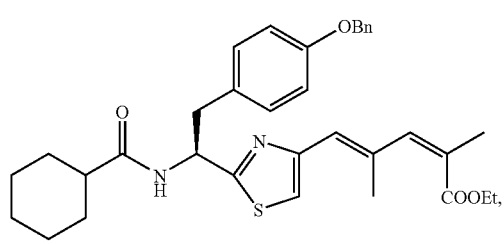
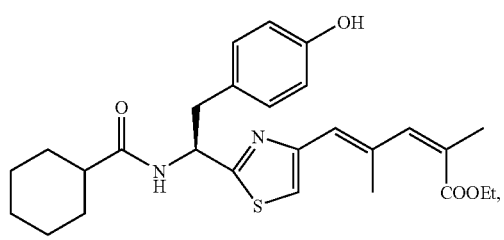
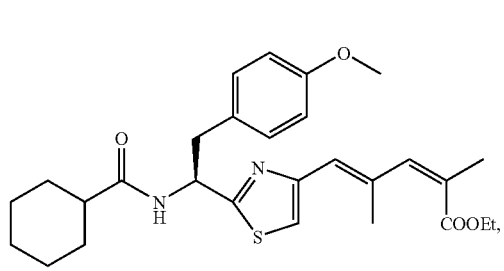
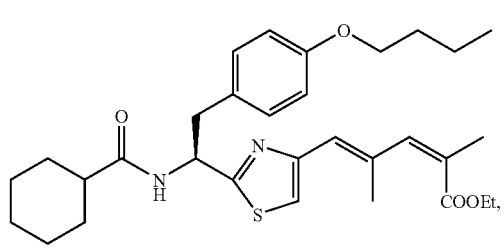
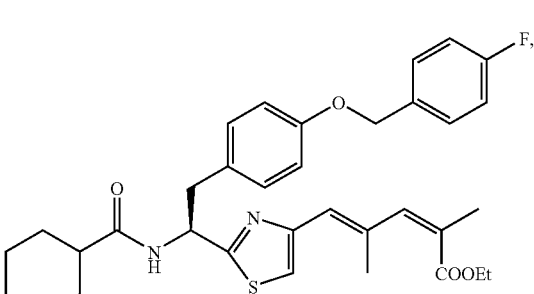
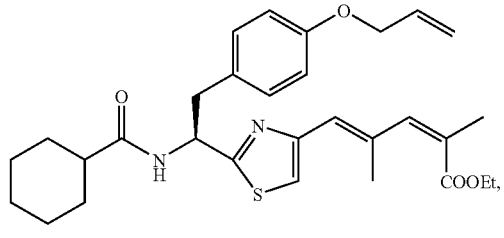
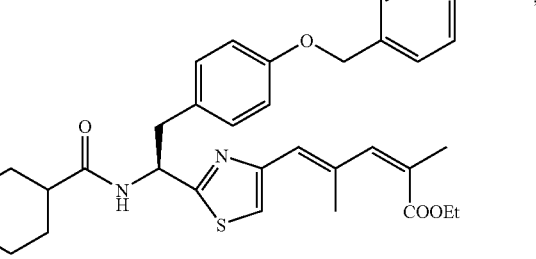

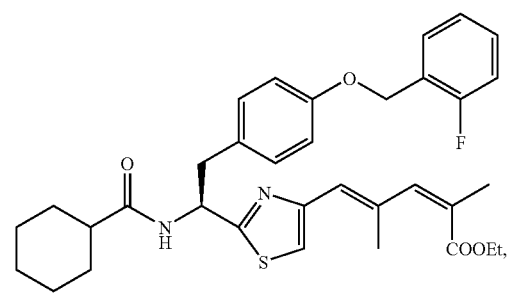
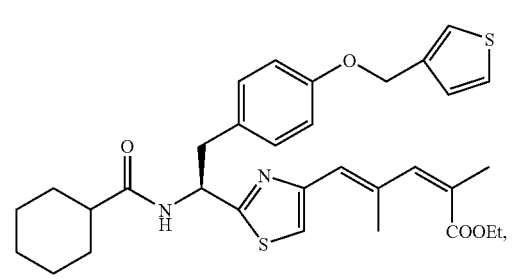
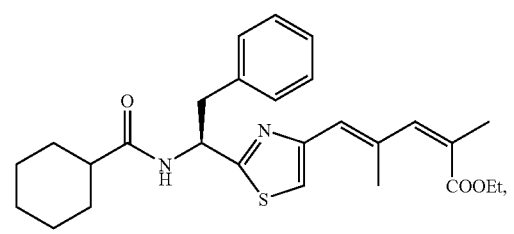
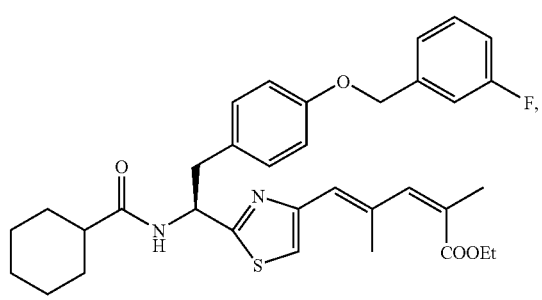
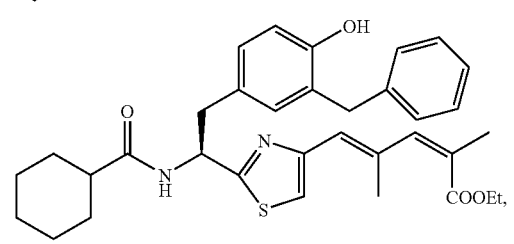
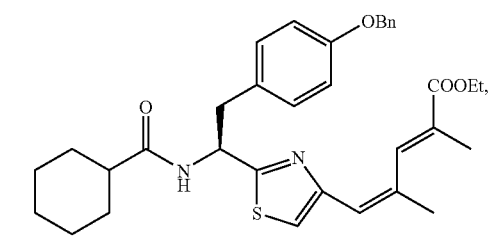
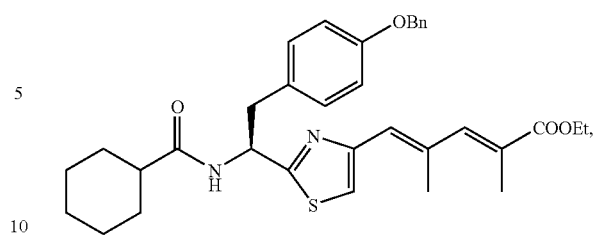
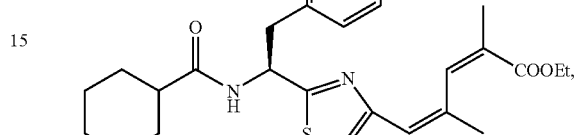
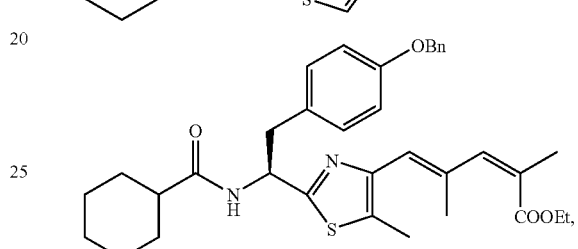
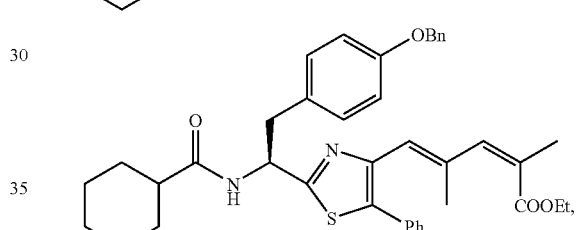
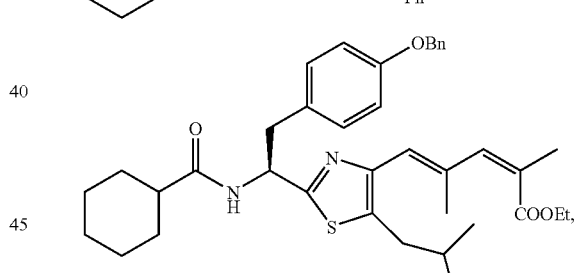
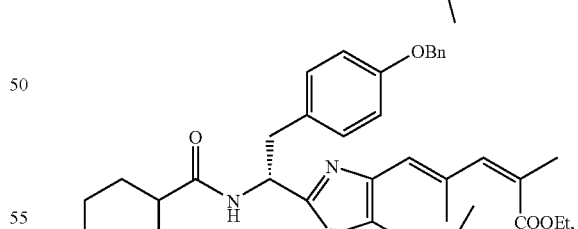
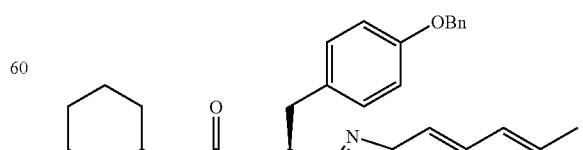
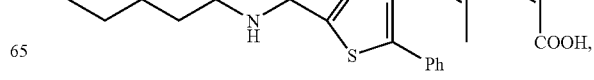

-continued
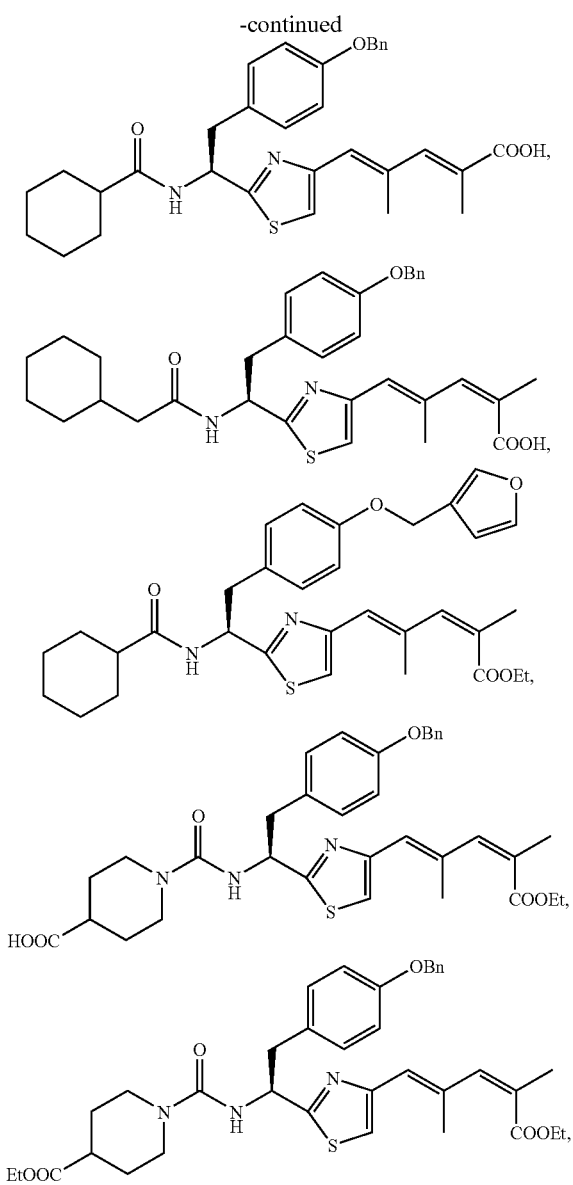
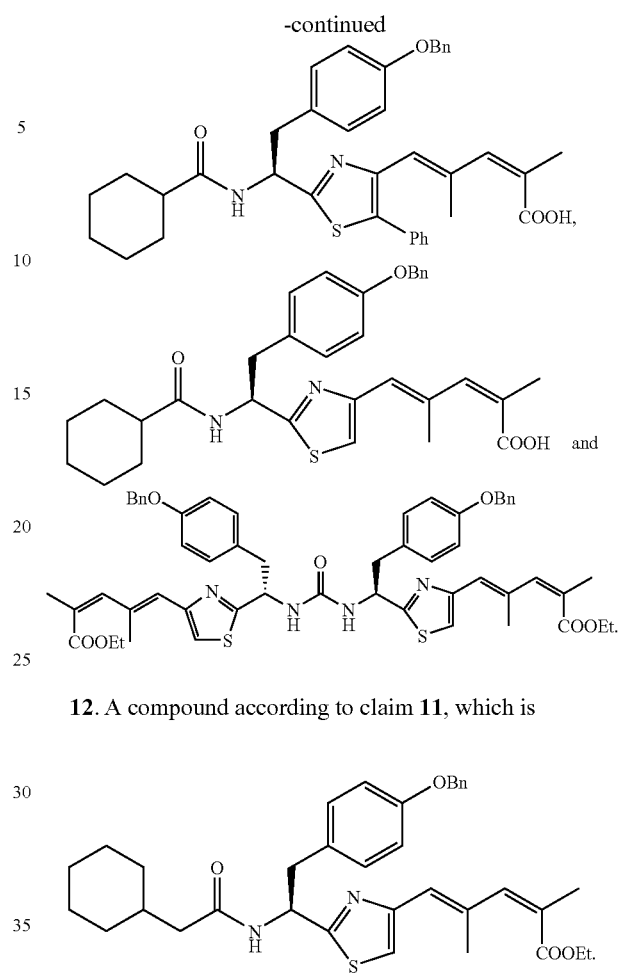
12. A compound according to claim 11, which is
13. A method of treating diseases mediated by PTP1B comprising administering the compound according to claim 1 to a patient, wherein the diseases selected from the group consisting of type II diabetes and obesity.
* * * * *